(12) United States Patent
Che et al.

(10) Patent No.: US 11,135,310 B2
(45) Date of Patent: Oct. 5, 2021

(54) GOLD PORPHYRIN-PEG CONJUGATES AND METHODS OF USE

(71) Applicant: The University of Hong Kong, Hong Kong (HK)

(72) Inventors: Chi Ming Che, Hong Kong (HK); Yik Sham Clive Chung, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 15/367,505

(22) Filed: Dec. 2, 2016

(65) Prior Publication Data

US 2017/0157261 A1 Jun. 8, 2017

Related U.S. Application Data

(60) Provisional application No. 62/264,525, filed on Dec. 8, 2015.

(51) Int. Cl.
| | |
|---|---|
| *A61K 47/69* | (2017.01) |
| *A61K 45/06* | (2006.01) |
| *A61K 31/555* | (2006.01) |
| *A61K 31/704* | (2006.01) |

(52) U.S. Cl.
CPC ........ *A61K 47/6935* (2017.08); *A61K 31/555* (2013.01); *A61K 31/704* (2013.01); *A61K 45/06* (2013.01)

(58) Field of Classification Search
CPC .............. A61K 47/6935; A61K 31/555; A61K 31/704; A61K 45/06
See application file for complete search history.

(56) References Cited

PUBLICATIONS

Sun et al. Synthesis and cancer cell cytotoxicity of water-soluble gold(III) substituted tetraarylporphyrin. Journal of Inorganic Biochemistry 108 (2012) 47-52. (Year: 2012).*
Preib et al. Gold(III) tetraarylporphyrin amino acid derivatives: ligand or metal centred redox chemistry? Chem. Sci., 2016, 7, 596-610. (Year: 2016).*
Kim et al. Water-Soluble Porphyrin-Polyethylene Glycol Conjugates with Enhanced Cellular Uptake for Photodynamic Therapy. Journal of Nanoscience and Nanotechnology vol. 9, 7130-7135, 2009. (Year: 2009).*
Lv et al. Thermosensitive porphyrin-incorporated hydrogel with four-arm PEG-PCL copolymer: Preparation, characterization and fluorescence imaging in vivo. Materials Science and Engineering C 43 (2014) 221-230. (Year: 2014).*
Tu et al. Gold (III) porphyrin complexes induce apoptosis and cell cycle arrest and inhibit tumor growth in colon cancer. Cancer. Oct. 1, 2009 ;115(19):4459-69. (Year: 2009).*
Kim et al. Water-Soluble Porphyrin-Polyethylene Glycol Conjugates with Enhanced Cellular Uptake for Photodynamic Therapy. J. Nanosci. Nanotechnol. 9, 7130-7135, 2009. (Year: 2009).*
Chung et al. A multi-functional PEGylated gold(III) compound: potent anti-cancer properties and self-assembly into nanostructures for drug co-delivery. Chem. Sci., 2017, 8, 1942-1953. (Year: 2017).*
A guidebook to particle size analysis. Ed. Horiba Instruments, Inc. 2017, 32 pages. (Year: 2017).*
Carvalho, et al., "Formulations for pulmonary administration of anticancer agents to treat lung malignancies", J Aerosol Med Pulm Drug Del., 24(2):61-80 (2011).
Chou, et al., "Theoretical basis, experimental design, and computerized simulation of synergism and antagonism in drug combination studies" Pharmacol. Rev., 58:621-81 (2006).
Davis, et al., "Nanoparticle therapeutics: an emerging treatment modality for cancer" Nat. Rev. Drug Discov., 7:771-82 (2008).
Dhar, et al., "Targeted delivery of cisplatin to prostate cancer cells by aptamer functionalized Pt(IV) prodrug-PLGA-PEG nanoparticles" PNAS, 105:17356-61 (2008).
Harris and Chess, "Effect of pegylation on pharmaceuticals" Nature Rev. Drug Discov., 2:214-21 (2003).
Wang, et al., "Nanoparticle delivery of cancer drugs" Annu. Rev. Med., 63:185-98 (2012).

\* cited by examiner

*Primary Examiner* — Robert A Wax
*Assistant Examiner* — Olga V. Tcherkasskaya
(74) *Attorney, Agent, or Firm* — Pabst Patent Group LLP

(57) ABSTRACT

Disclosed are conjugates, compositions, and methods that include or use one or more gold(III) porphyrin complexes. Preferred conjugates are gold(III) porphyrin-poly(ethylene glycol) (PEG) conjugates. Preferred compositions and methods include or use such gold(III) porphyrin-PEG conjugates. Disclosed is a method for treatment of cancer comprising administering to a human in need of such treatment a composition containing a therapeutically effective amount of gold(III) porphyrin-poly(ethylene glycol) (PEG) conjugates. The gold(III) porphyrin-PEG conjugates can be in the form of nanostructures formed by self-assembly of the gold(III) porphyrin-PEG conjugates; or nanocomposites formed by encapsulation of other therapeutic agents by the nanostructures of gold(III) porphyrin-PEG conjugates.

25 Claims, 16 Drawing Sheets

GOLD PORPHYRIN-PEG CONJUGATES AND METHODS OF USE

CROSS-REFERENCE TO RELATED APPLICATIONS

The present application claims priority to U.S. Application No. 62/264,525, filed on Dec. 8, 2015, the disclosures of which are incorporated herein by reference in their entirety.

FIELD OF THE INVENTION

The subject matter herein relates in general gold(III) porphyrin-PEG conjugates which can undergo self-assembly into nanostructures in aqueous media, methods for encapsulation of therapeutic agents, and methods for treatment of cancer using the nanostructures and nanocomposites of gold(III) porphyrin-PEG conjugates.

BACKGROUND OF THE INVENTION

Cisplatin and its derivatives are used as chemotherapeutic agents against various forms of cancer including testicular, bladder, head and neck, ovarian, breast, lung, prostate, and refractory non-Hodgkin's lymphomas. However, toxic side effects and the emergence of drug resistance found in the clinical application of these platinum-based compounds have prompted the scientific community to develop new generations of chemotherapeutic agents [Sadler, et al. *Curr. Opin. Chem. Biol.* 2008, 12, 197]. Unlike cisplatin and many other platinum-based drugs which primarily target DNA, gold(I) and/or gold(III) complexes have demonstrated a variety of actions, including inhibition of thioredoxin reductase, direct DNA damage, alteration of cell cycle, proteasome inhibition and modulation of specific kinases [Che, et al. *Chem. Soc. Rev.* 2015, in press]. These multi-modes of actions are important for the gold complexes to display potent cytotoxicity toward cancer cells, particularly toward cisplatin- and multidrug-resistant cell lines. For example, gold(III) tetraphenylporphyrin complexes were found to cause depletion of mitochondrial potential and induction of apoptosis by both the caspase-dependent and caspase-independent mitochondrial death pathways. Together with their excellent stability under physiological conditions which were significantly different from the readiness of decomposition of other gold complexes in biological media, the gold(III) tetraphenylporphyrin complexes displayed promising in vivo anti-cancer activities against different types of carcinoma, including those showing cisplatin-resistance [Che, et al. *Chem. Commun.* 2011, 47, 9554]. However, the gold(III) tetraphenylporphyrin complexes exhibit poor bioavailability and high toxicity toward normal cells and tissues, which are also commonly found in the studies of other metallodrugs, thereby hindering the translation of the complexes for clinical studies.

Advances in nanotechnology can help to overcome challenges found in the in vivo experiments of anti-cancer metal complexes [Farokhzad, O. C.; Lippard, et al. *Proc. Natl. Acad. Sci. U.S.A.* 2008, 105, 17356]. Due to the presence of leaky tumor vasculatures and impaired lymphatic system in solid tumors, nanostructures of around 100 nm were found to show accumulation in tumor vicinity by the enhanced permeability and retention (EPR) effect [Davis, et al. *Nat. Rev. Drug Discov.* 2008, 7, 771.] Therefore, nano-formulations would allow significant improvement in biodistribution, and more importantly, reduction of toxic side effects which is commonly observed in traditional therapeutic agents. Conventional strategy for nano-formulations includes encapsulation of drug molecules by nanoscale carriers and covalent linkage of drug molecules to pre-formed nanostructures (e.g. gold nanoparticles and magnetic iron oxide nanoparticles).

Although encapsulation of drug molecules by nanoscale carriers and covalent linkage of drug molecules to pre-formed nanostructures has been shown to have in vitro and/or in vivo anti-cancer efficacy, toxicity of the components in nanocarriers as well as preformed nanostructures raises significant concerns. An example is the product Doxil sold under the trade name DOXIL®, which is a clinically approved formulation of doxorubicin by poly(ethylene glycol) (PEG)-nano liposome. DOXIL® administration causes skin toxicity (associated with the PEG-liposome carrier) which does not occur in the administration of doxorubicin alone. Thus, the development of nanostructures with minimal content of the components for nano-assembly would be beneficial for chemotherapy.

It is an object of the present invention to provide gold (III)-porphyrin conjugates for use in cancer therapy.

It is also an object of the present invention to provide a method of making drug loaded nano- or microstructures without the aid of nanocarriers or preformed nanostructures.

It is still an object of the present invention to provide nano- or microstructure chemotherapeutic carriers which minimal nanocarriers or preformed nanostructures.

It is also an object of the present invention to provide a method of selectively targeting cancer in a subject in need thereof.

It is still an object of the present invention to provide a method of selectively delivering a chemotherapeutic to tumor cells in a subject.

It is a further object of the present invention to provide a method of treating chemotherapy resistant cancers.

BRIEF SUMMARY OF THE INVENTION

The compositions and methods described herein are based on the discovery that supramolecular self-assembly of amphiphilic metal complexes through non-covalent interactions can lead to the formation of nano- or microstructures without the aid of nanocarriers or preformed nanostructures. This offers an attractive strategy for nano-formulation of gold(III) porphyrin complexes which are rather hydrophobic in nature. An introduction of hydrophilic components onto the hydrophobic gold(III) porphyrin complexes can in some instances render the complexes amphiphilic properties, thus facilitating their formation of nanostructures for targeting tumor vicinity in vivo by the EPR effect.

Provided herein are self-assembled amphiphilic gold(III) porphyrin (GP) conjugates and salts thereof for use in cancer therapy. In a preferred embodiment, the gold(III) porphyrin conjugate is a gold(III) porphyrin-poly(ethylene glycol) (PEG) conjugate having the structural formula of Formula I:

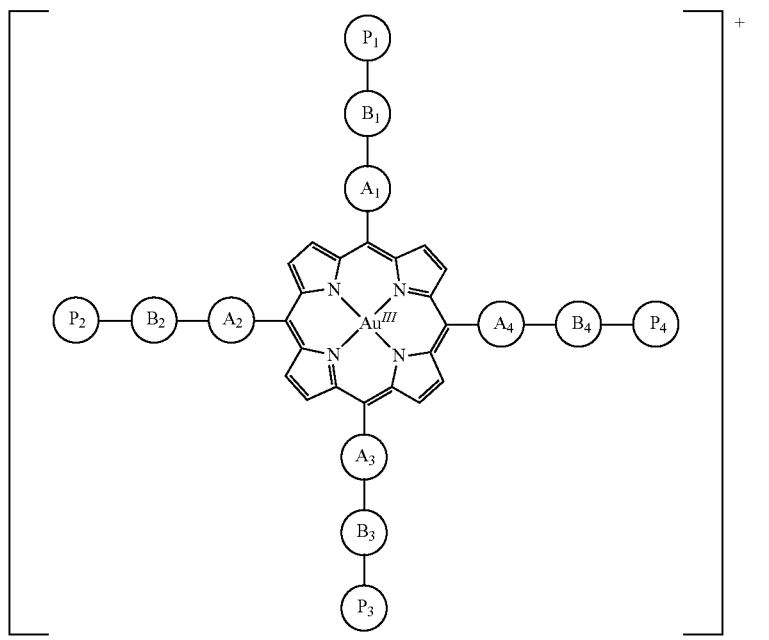

or a pharmaceutically acceptable salt thereof, wherein: X is independently a pharmaceutically acceptable counter-ion; $A_1$, $A_2$, $A_3$ and $A_4$ are independently aryl or aryl substituted with a halogen, hydroxy, alkoxy, amino, amido, carboxyl, ester, carbonyl, formyl, thio, alkythio, sulfonyl, sulfonic acid, azidyl, nitro, isocyanate-yl, alkenyl, alkynyl, phosphoryl, phosphonyl group; and where optionally and independently at least one of the $A_n$ forms covalent linkage with $B_n$ (if $B_n$ is not $C_0$) or $P_n$ (if $B_n$ is $C_0$); $B_1$, $B_2$, $B_3$ and $B_4$ are independently $C_0$ or spacer molecules of $C_1$-$C_8$ alkyl groups with two end groups, forming covalent linkages with $A_n$ and $P_n$; $P_1$, $P_2$, $P_3$ and $P_4$ are independently hydrogen or poly (ethylene glycol) (PEG) forming covalent linkages with $A_n$ (if $B_n$ is $C_0$) or $B_n$ (if $B_n$ is not $C_0$); and where optionally and independently at least one of the $P_n$ are PEG forming covalent linkage with $A_n$ (if $B_n$ is $C_0$) or $B_n$ (if $B_n$ is not $C_0$).

The nano/microstructure formed from the GP conjugates or salts therein can be included in a pharmaceutical formulation in a therapeutically effective amount to induce cancer cell death. The GP conjugates can be used alone or in combination with one or more chemotherapeutic agents in a formulation for cancer therapy. In this embodiment, the nano/microstructure formed from the GP conjugate or salt thereof is preferably used to encapsulate/as a carrier for the one or more therapeutic agents to achieve co-delivery.

Also disclosed herein are methods for the treatment of cancer comprising administering to a subject in need of such treatment a composition containing an effective amount of a GP conjugate or salt thereof to induce cancer cell death, alone, or in combination with one or more chemotherapeutic agents.

Also disclosed herein are methods for reducing efflux pump-mediated drug resistance in a subject in need of such treatment comprising administering to the subject a composition containing an effective amount of a GP conjugate or salt thereof to induce cancer cell death, alone, or in combination with one or more chemotherapeutic agents.

Also disclosed herein are methods for selectively delivering a chemotherapeutic agent to a site in need thereof, comprising encapsulating the chemotherapeutic agent in a nano-microstructure comprising GP-PEG (GPP) conjugates and administering the encapsulated chemotherapeutic agent to o a site in need of such treatment.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 3C shows the bar chart of the ratio of cellular uptake of the complexes (2 μM) into cancer and non-tumorigenic cells after incubation for 2 h at 37° C. In each grouping of bars, the bars are in the same left-to-right order: A2780 versus MIHA, A2780 versus NCM460, A2780adr versus MIHA, A2780adr versus NCM640, HCT116 versus MIHA, HCT116 versus NCM460.

DETAILED DESCRIPTION OF THE INVENTION

Figure 1:
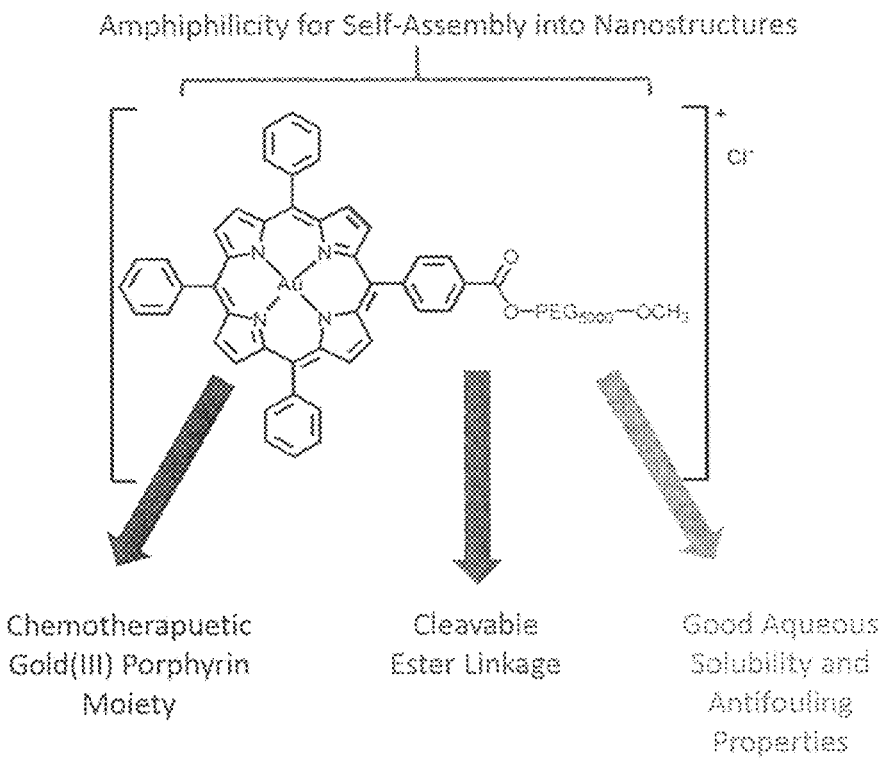
FIG. 1 shows the multi-functional properties of conjugate 1 which are important for its unique self-assembly properties and potent anti-cancer properties.

The disclosed method and compositions may be understood more readily by reference to the following detailed description of particular embodiments and the Example included therein and to the Figures and their previous and following description.

Described herein are gold(III) porphyrin-PEG (GPP) conjugates as well as the use of the nanocomposites of gold(III) porphyrin-PEG conjugates as anti-cancer agents, alone, or in combination with other therapeutic agents. The GPP conjugates or salts thereof can be used to selectively target cancer cells by virtue of their selective uptake by cancer cells when compared to non-cancer cells. The GPP conjugates or salts thereof can be used to treat efflux pump-mediated drug resistance by co-administering the drug with a GPP conjugate as disclosed herein.

Disclosed are conjugates, compositions, and methods that include or use one or more gold(III) porphyrin complexes. Preferred conjugates are gold(III) porphyrin-poly(ethylene glycol) (PEG) conjugates. Preferred compositions and methods include or use such gold(III) porphyrin-PEG conjugates.

In some forms, the gold(III) porphyrin-PEG conjugate can have the structure:

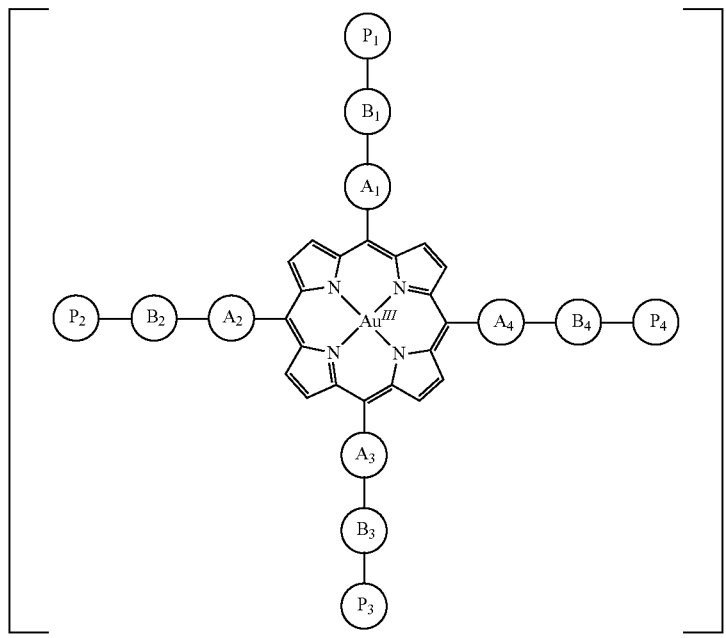

including pharmaceutically acceptable salt thereof. In some forms of this gold(III) porphyrin-PEG conjugate:

X can be independently a pharmaceutically acceptable counter-ion;

$A_1$, $A_2$, $A_3$ and $A_4$ can be independently aryl or aryl substituted with a halogen, hydroxy, alkoxy, amino, amido, carboxyl, ester, carbonyl, formyl, thio, alkythio, sulfonyl, sulfonic acid, azidyl, nitro, isocyanate-yl, alkenyl, alkynyl, phosphoryl, or phosphonyl group, where, optionally and independently, at least one of the $A_n$ can form a covalent linkage with $B_n$ (if $B_n$ is not $C_0$) or $P_n$ (if $B_n$ is $C_0$);

$B_1$, $B_2$, $B_3$ and $B_4$ can be independently $C_0$ or spacer molecules of $C_1$-$C_8$ alkyl groups with two end groups that form covalent linkages with $A_n$ and $P_n$; and $P_1$, $P_2$, $P_3$ and $P_4$ can be independently hydrogen or poly(ethylene glycol) (PEG) that forms covalent linkages with $A_n$ (if $B_n$ is $C_0$) or $B_n$ (if $B_n$ is not $C_0$), where, optionally and independently, at least one of the $P_n$ is PEG that forms a covalent linkage with $A_n$ (if $B_n$ is $C_0$) or $B_n$ (if $B_n$ is not $C_0$).

In some forms of the gold(III) porphyrin-PEG conjugate, $A_1$ is —$C_6H_4C(=O)$— or —$C_6H_4O$—; $B_1$ is $C_0$ or —$C(=O)(CH_2)_8C(=O)$—; and $P_1$ is —O-PEG—$OCH_3$ or —NH-PEG—$OCH_3$.

In some forms of the gold(III) porphyrin-PEG conjugate, $P_1$ is —O-PEG$_{\sim 5000}$—$OCH_3$ or —NH-PEG$_{\sim 5000}$—$OCH_3$. In some forms of the gold(III) porphyrin-PEG conjugate, $A_2$, $A_3$ and $A_4$ are each aryl; $B_2$, $B_3$ and $B_4$ are each $C_0$; $P_2$, $P_3$ and $P_4$ are each hydrogen; and optionally, X is chloride.

In some forms, the gold(III) porphyrin-PEG conjugate undergo self-assembly into nanostructures in aqueous media. In some forms, the gold(III) porphyrin-PEG conjugate can undergo self-assembly into nanostructures in aqueous media, thereby forming nanocomposites. If a therapeutic agent or other compound or composition of interest is present, the gold(III) porphyrin-PEG conjugate can undergo self-assembly into nanostructures in aqueous media to forming nanocomposites comprising the therapeutic agent and the gold(III) porphyrin-PEG conjugate. In some forms, the gold(III) porphyrin-PEG conjugates can encapsulate one or more anti-cancer chemotherapeutic agents, thereby forming nanocomposites for co-delivery.

In some forms, the nanostructures or microstructures of gold(III) porphyrin-PEG conjugates can induce apoptosis in cancer cells when administered to a subject having cancer cells. Such a subject can be said to be in need of induction of cancer cell death.

Also disclosed are anti-cancer chemotherapeutic agents. In some forms, the anti-cancer chemotherapeutic agents is doxorubicin or is a $d^8$ metal complex with an N-heterocyclic carbene (NHC) ligand having the structural formula of:

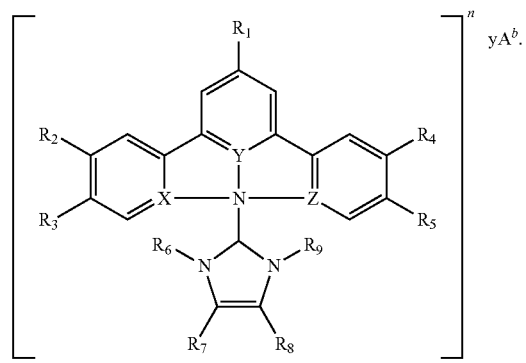

In some form of this NHC ligand: M can be Au, Pt, or Pd; $R_1$ can be hydrogen or phenyl; $R_2$ and $R_3$ can each be hydrogen or together can be —CH=CH—CH=CH—; $R_4$, $R_5$, $R_7$, and $R_8$ can each be hydrogen; $R_6$ and $R_9$ can each independently be selected from —$CH_3$, —$C_2H_5$, —$C_3H_7$, —$C_4H_9$, —$O_5H_{11}$, —$C_6H_{13}$, benzyl, (2-hydroxy) ethyl, phenyl, naphthalen-2-ylmethyl, and (2-phenyl) ethyl; n can be +1 or +2; y can be +1 or +2; A can be a counter-ion or a pharmaceutically acceptable anion; b can be −1 or −2; and X, Y, and Z can each independently be carbon or nitrogen. In some forms, of this NHC ligand: M can be Pt; $R_1$, $R_2$, $R_3$, $R_4$, $R_5$, $R_7$, and $R_8$ can each be hydrogen; $R_6$ and $R_9$ can be —$C_4H_9$; n can be +1; $yA^b$ can be $CF_3SO_4^-$; X can be carbon; and Y and Z can each be nitrogen.

Disclosed are methods of inducing cancer cell death in a subject in need thereof. In some forms of the method, a composition comprising an effective amount of one or more of the disclosed gold(III) porphyrin-PEG conjugates is administering to the subject. In some forms of the method, the composition induces apoptosis in cancer cells in the subject.

Also disclosed are methods of targeting delivery of a therapeutic agent to cancer cells in a subject. In some forms of the method, the therapeutic agent is encapsulated in nanostructures or microstructures comprising one or more of the disclosed gold(III) porphyrin-PEG conjugates. In some forms of the method, the gold(III) porphyrin-PEG conjugates undergo self-assembly into nanostructures in aqueous media, thereby forming nanocomposites comprising the therapeutic agent and the gold(III) porphyrin-PEG conjugate.

In some forms, the subject can have a cancer selected from the group consisting of colorectal, colon, ovarian, lung, breast carcinoma and multiple myeloma, cisplatin-resistant cancer, and adriamycin-resistant cancer.

A. DEFINITIONS

As used herein, the phrase "pharmaceutically acceptable salt," as used herein, includes salts formed from an atom, compound, conjugate, or complex (e.g., charged gold(III) complex) and a counter-ion. Generally, the pharmaceutically acceptable salt will be a salt approved or accepted by a regulatory agency of the Federal or a state government or listed in the US. Pharmacopoeia or other generally recognized pharmacopoeia for use in animals, mammals, and more particularly in humans.

As used herein, the term "porphyrin" refers to a molecule having structure I:

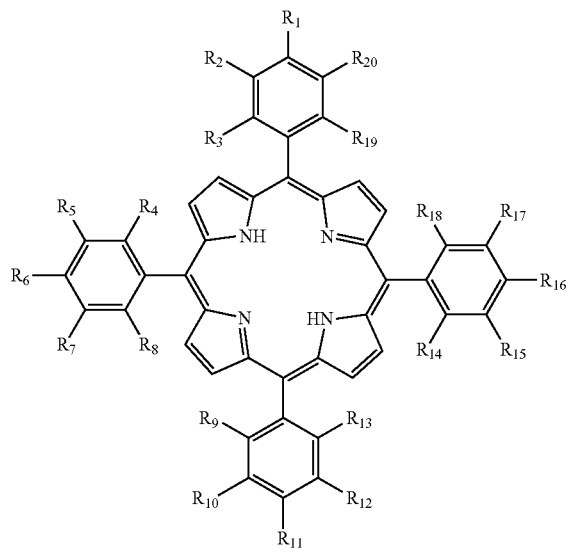

$R_1$-$R_{20}$ are independently selected from hydrogen and a halogen, hydroxy, alkoxy, amino, amido, carboxyl, ester, carbonyl, formyl, thio, alkythio, sulfonyl, sulfonic acid, azidyl, nitro, isocyanate-yl, alkyl, cycloalkyl, heterocycloalkyl, aryl, alkenyl, alkynyl, phosphoryl, phosphonyl, and substituted $C_1$-$C_8$ alkoxy, substituted amino group or substituted carbonyl, where, optionally and independently, at least one of the $R_1$-$R_{20}$ is hydroxy, unsubstituted or substituted amino, carboxyl, carbonyl, formyl, azidyl, alkenyl, alkynyl, thio or isocyanate-yl for forming covalent linkage with spacer(s) or PEG.

The terms "substituent" and "substitute" as used herein refers to all permissible substituents of the compounds or functional groups described herein. The term "substituted" refers to a compound that has one group (usually a hydrogen or carbon) substituted with a substituent. The term "substituted with" in connection with a compound, structure, R group, etc., refers to substituents of the referenced compound, structure, R group, etc. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$—$C_{20}$ cyclic, substituted $C_3$—$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$—$C_{20}$ cyclic, substituted $C_3$—$C_{20}$ cyclic, heterocyclic, substituted heterocyclic, amino acid, poly(lactic-co-glycolic acid), peptide, and polypeptide groups can be further substituted.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. The term "ethyl" as used herein is an alkyl having two carbons.

The term "alkenyl" as used herein is a hydrocarbon group of 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl" as used herein is a hydrocarbon group of 2 to 24 carbon atoms and a structural formula containing at least one carbon-carbon triple bond.

The terms "amino" and "amine" as used herein are art-recognized and refer to both substituted and unsubstituted amines, e.g., a moiety that can be represented by the general formula:

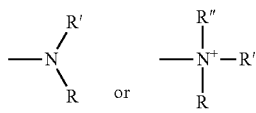

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'''. Thus, the term 'alkylamine' as used herein refers to an amine group, as defined above, having a substituted or unsubstituted alkyl attached thereto (i.e. at least one of R, R', or R" is an alkyl group).

The term "aryl" as used herein is any carbon-based aromatic group including, but not limited to, benzene, naphthalene, etc. The term "aromatic" also includes "heteroaryl", which is defined as an aromatic group that has at least one heteroatom incorporated within the ring of the aromatic group. Examples of heteroatoms include, but are not limited to, nitrogen, oxygen, sulfur, and phosphorus.

The term "phenyl" as used herein is art recognized, and refers to the aromatic moiety —$C_6H_5$, i.e., a benzene ring without one hydrogen atom.

The term "substituted phenyl" as used herein refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof. The term "benzyl" as used herein is a special form of substituted phenyl having a —CH2-group replacing one of the hydrogen atoms on one of the carbons of the phenyl ring.

The term "alkoxy" as used herein is an alkyl group bound through a single, terminal ether linkage; that is, an "alkoxy" group may be defined as —OR where R is alkyl as defined above.

The term "substituted alkoxy" as used herein is represented by the formula —O—R—X, where R is alkyl as defined above and X can be independently a halogen, hydroxy, alkoxy, amino, amido, carboxyl, ester, carbonyl, formyl, thio, alkythio, sulfonyl, sulfonic acid, azidyl, nitro, isocyanate-yl, alkenyl, alkynyl, phosphoryl, or phosphonyl group.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "carbonyl" as used herein is art-recognized and includes such moieties as can be represented by the general formula:

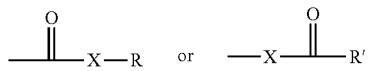

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

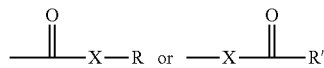

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

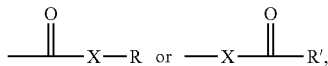

and is defined more specifically by the formula —R'COOH, wherein R' is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$—$C_{30}$ for straight chain alkyl, $C_3$—$C_{30}$ for branched chain alkyl, $C_2$—$C_{30}$ for straight chain alkenyl and alkynyl, $C_3$—$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure. The term "carboxylic acid" as used herein is a special form of carboxyl represented by the formula —C(O)OH.

The term "substituted carboxyl" refers to a carboxyl, as defined above, wherein one or more hydrogen atoms in R' are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "aldehyde" as used herein is represented by the formula —C(O)H.

The term "keto" as used herein is represented by the formula —C(O)R, where R is an alkyl, alkenyl, alkynyl, aryl, aralkyl, cycloalkyl, halogenated alkyl, or heterocycloalkyl group described above.

The term "carbonyl" as used herein is represented by the formula C═O.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "amido" as used herein is represented by the formula —C(O)NR—, where R is an alkyl, alkenyl, alkynyl, aryl, aralkyl, cycloalkyl, halogenated alkyl, or heterocycloalkyl group described above.

The term "isocyanate-yl" as used herein is represented by the formula —N═C═O.

"Halogen," as used herein, refers to fluorine, chlorine, bromine, or iodine. The terms "hydroxyl" and "hydroxy" as used herein are used interchangeably and are represented by —OH.

The term "nitro" as used herein refers to —$NO_2$.

The term "phosphonyl" as used herein is represented by the formula —P(O)RR', where R and R' can be independently alkyl, halogenated alkyl, alkenyl, alkynyl, aryl, heteroaryl, cycloalkyl, cycloalkenyl, heterocycloalkyl, or heterocycloalkenyl group described above.

The term "phosphoryl" as used herein is represented by the formula —$PO_3^-$.

The term "sulfonyl" as used herein is represented by the formula —$SO_2R$, where R is an alkyl, halogenated alkyl, alkenyl, alkynyl, aryl, heteroaryl, cycloalkyl, cycloalkenyl, heterocycloalkyl, or heterocycloalkenyl group described above.

The term "sulfonic acid" as used herein is represented by the formula —$SO_3H$.

The term "sulfonyl" as used herein is represented by the formula

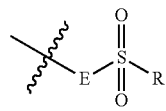

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "azidyl" as used herein is represented by the formula —$N_3$.

The term "formyl" as used herein is represented by the formula —C(O)H.

The term "thio" as used herein is represented by the formula —SH.

The term "alkylthio" as used herein is represented by the formula —SR, where R is an alkyl, alkenyl, alkynyl, aryl, aralkyl, cycloalkyl, halogenated alkyl, or heterocycloalkyl group described above.

As used herein, the phrase "PEG" refers to poly(ethylene glycol) with molecular weight ranging from 500 to 10,000. The molecular weight or average molecular weight of PRG can be designated by a subscript of the eight in daltons (e.g., $PEG_{2000}$ and $PEG_{\sim 5000}$ for PEG of molecular weight 2000 daltons and PEG of approximate molecular weight of 500 daltons, respectively). Unless otherwise stated clearly to the contrary, reference to PEG of a particular molecular weight refers to the average molecular weight of the PEG composition. The two end groups of PEG are independently hydroxyl, methoxy, amino, amido, carboxyl, thio, carbonyl, alkynyl, azidyl, biotinyl, phosphoryl, phosphonyl, phosphonyl, sulfonyl, sulfonic acid, silanyl, N-hydroxysuccinimide ester or maleimide.

As used herein, the term "conjugates" refers to the compounds with covalent bonding between gold(III) porphyrin complexes and PEG, either directly or through a spacer.

The term "spacer" as used herein by the formula X—Y—Z, where X and Z can be ester, carbonate, carbamate, amide, benzoic-imine. hydrazone, 1,2,3-triazole or thioether forming covalent linkages with gold(III) porphyrin moiety and PEG. Y is a hydrocarbon group of 1 to 8 carbon atoms.

The term "carbonate" as used herein is represented by the formula —OC(O)O—.

The term "carbamate" as used herein is represented by the formula —OC(O)NR—, where R can be hydrogen, or an alkyl, alkenyl, alkynyl, aryl, aralkyl, cycloalkyl, halogenated alkyl, or heterocycloalkyl group generally as described elsewhere herein.

The term "benzoic-imine" as used herein is represented by the formula-PhCH=N—, where Ph can be aryl, aralkyl or heteroaryl.

The term "hydrazone" as used herein is represented by the formula —RC=NNH$_2$, where R can be hydrogen, an alkyl, alkenyl, alkynyl, aryl, aralkyl, cycloalkyl, halogenated alkyl, or heterocycloalkyl group described elsewhere herein.

The term "1,2,3-triazole" as used herein is represented by the following formula:

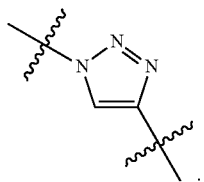 [SMILES: *c1cn(*)nn1]

The term "thioether" as used herein is represented by the formula —S—.

The term unsubstituted "$C_x$" in reference to a compound, substituent, moiety, etc., refers to a compound, substituent, moiety, etc., having x carbon atoms.

The term unsubstituted "$C_y$—$C_x$" in reference to a compound, substituent, moiety, etc., refers to a compound, substituent, moiety, etc., having from y to x carbon atoms, inclusive. For example, $C_1$-$C_8$ alkyl is an alkyl having from 1 to 8 carbon atoms, inclusive.

The term unsubstituted "$C_0$" in reference to a compound, substituent, moiety, etc., refers to a compound, substituent, moiety, etc., having zero carbon atoms. Examples of $C_0$ compounds, substituents, moieties, etc., include sulfonyl, sulfonic acid, sulfamoyl, phosphoryl, and phosphonyl.

As used herein, the phrase "counter-ion" refers to an ion associated with an oppositely charged conjugate or complex. Examples of counter-ions include counter-anions and counter-cations.

As used herein, the phrase "counter-anion" refers to an anion associated with a positively charged conjugate or complex (e.g., a charged gold(III) complex). Non-limiting examples of counter-anions include halogens such as fluoride, chloride, bromide, and iodide, sulfate, phosphate, trifluoromethanesulfonate, acetate, nitrate, perchlorate, acetylacetonate, hexafluoroacetylacetonate and hexafluorophosphate.

As used herein, the term "self-assembly" refers to the formation of ordered structures from conjugates or complexes (e.g., the gold(III) porphyrin complexes) through non-covalent supramolecular interactions. Non-limiting examples of non-covalent supramolecular interactions include hydrophobic interactions, 7C-7C interactions, hydrogen bonding, metal-metal interactions, C-H—O interactions and C-H-X (where X is F or Cl) interactions.

As used herein, the phrase "nanostructures" refers to ordered structures of any possible geometry with at least one of the dimensions in the range of 10-1000 nm. Non-limiting examples of the geometry of order structures include spherical, cylindrical, disk-like, wheel-like and fibrous structure.

As used herein, the phrase "microstructures" refers to ordered structures of any possible geometry with at least one of the dimensions in the range of 1-1000 μm. Non-limiting examples of the geometry of order structures include spherical, cylindrical, disk-like, wheel-like and fibrous structure.

As used herein, the phrases "nano/microstructures," "nanostructures and microstructures," "nano- and microstructures," and the like refer to ordered structures of any possible geometry with at least one of the dimensions in the range of 10 nm-1000 μm. Non-limiting examples of the geometry of order structures include spherical, cylindrical, disk-like, wheel-like and fibrous structure.

As used herein, the phrase "nanocomposites" refers to multi-component structures formed by encapsulation of one or more than one therapeutic agents by the nanostructures of gold(III) porphyrin-PEG conjugates.

As used herein, the term "encapsulation" refers to the holding of one or more than one compounds by an ordered structure through non-covalent interactions. Non-limiting examples of non-covalent supramolecular interactions include hydrophobic interactions, π-π interactions, hydrogen bonding, metal• • •metal interactions, C—H• • •O interactions and C—H• • •X (where X is F or Cl) interactions. The compounds can be located at any part of the ordered structure, such as central cavity, shell or surface.

As used herein, the phrases "pharmaceutically acceptable ion," "pharmaceutically acceptable anion," "pharmaceutically acceptable cation," "pharmaceutically acceptable counter-ion," "pharmaceutically acceptable counter-anion," "pharmaceutically acceptable counter-cation," means an ion, anion, cation, counter-ion, counter-anion, or counter-cation, respectively, approved or accepted by a regulatory agency of the Federal or a state government or listed in the US. Pharmacopoeia or other generally recognized pharmacopoeia for use in animals, mammals, and more particularly in humans.

The term "subject" as used herein includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The terms "administering," "administer," and the like as used herein refer to contacting a substance or product to the body of a subject. For example, administering a substance or a product includes contacting the skin of a subject and injecting or implanting a substance or product into the subject.

The terms "treatment" and "treating" as used herein refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount. Treatment includes administration of a compound, conjugate, complex, compositions, etc. as a treatment as defined above.

The term "effective amount" as used herein generally refers to the amount of compound, complex, conjugate, composition, etc., in order to provide a desired result, such as one or more clinically measurable endpoints. The exact amount required may vary from subject to subject, depending on the species, age, and general condition of the subject; the severity of the disease that is being treated; the particular cell, capsule, product, device, material, composition, or compound used; its mode of administration; and other routine variables. An appropriate effective amount can be determined by one of ordinary skill in the art using only routine experimentation.

The term "anti-cancer agent" as used herein refers to any compound, conjugate, complex, composition, substance, etc., that has a negative effect on cancer or any of its symptoms or effects. Anti-cancer agents can be defined and referred to in relation to specific or particular effects of classes of effects. For example, an anti-cancer agent can be an agent that induces cancer cell death (i.e., apoptosis). Examples of anti-cancer agents include anti-cancer chemotherapeutic agents, anti-cancer therapeutic agents, anti-cancer compounds, anti-cancer complexes, anti-cancer metal complexes, anti-cancer conjugates, anti-cancer nanostructures, anti-cancer microstructures, and anti-cancer nanocomposites.

The term "pharmaceutically acceptable carrier" as used herein means a carrier combination of carrier ingredients approved by a regulatory agency of the Federal or a state government or listed in the US. Pharmacopoeia or other generally recognized pharmacopoeia for use in animals, mammals, and more particularly in humans.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a conjugate is disclosed and discussed and a number of modifications that can be made to a number of molecules including the conjugate are discussed, each and every combination and permutation of conjugate and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

B. COMPOSITIONS

The pharmaceutical compositions contain different synthetic gold(III) porphyrin-PEG conjugates in amounts effective to induce cancer cell death. The gold(III) porphyrin-PEG conjugates also provides a method to inhibit the growth of tumor cells in a subject, preferably a human afflicted with cancer that involves administering to such human an effective tumor cell growth inhibiting amount of a gold(III) porphyrin-PEG conjugates. Evidence reported herein indicates that the gold(III) porphyrin-PEG conjugates form nanostructures in aqueous media, and the nanostructures revealed potent anti-cancer properties with significant reduction of toxicity toward non-tumorigenic cells which are substantially different from the gold(III) porphyrin complexes without PEG conjugation. Specifically, data reported herein indicates that the nanostructures of gold(III) porphyrin-PEG conjugates show controlled release properties and faster cellular uptake into cancer cells than that into non-tumorigenic cells, thus resulting in effective killing of cancer cells over non-tumorigenic cells. Also, data reported herein indicates the encapsulation of other therapeutic agents by the nanostructures of gold(III) porphyrin-PEG conjugates, and the nanocomposites demonstrated synergism on killing cancer cells with reduction of toxicity toward non-tumorigenic cells, as well as the ability to overcome efflux pump-mediated drug resistance of ovarian cancer cells.

1. Gold (III) Porphyrin Complexes, Conjugates, Nanostructures, and Nanocomposites i. Gold (III) Porphyrin Complexes A series of gold(III) porphyrin complexes that show anti-proliferative activities against a panel of human cancer cells including those derived from nasopharyngeal and hepatocellular carcinoma are known. However, these complexes are toxic toward non-tumorigenic cells. For example, the effective dose of [Au(TPP)]Cl (Au1a; TPP=5,10,15,20-tetraphenylporphyrin) to combat tumor growth was close to the lethal dose of the complex, as revealed by acute toxicological study [Che, C. M. et al. *Chem. Commun.* 2011, 47, 9554]. In addition, gold(III) porphyrin complexes, examples of which are provided below, generally show poor solubility in aqueous media.

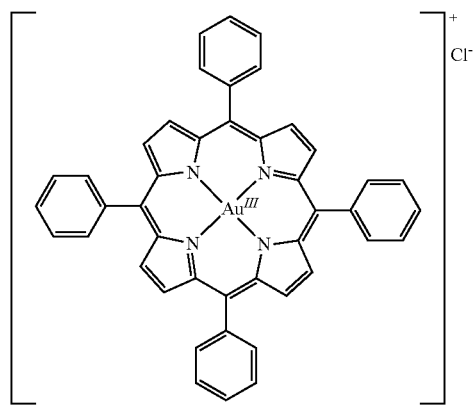

Au1a

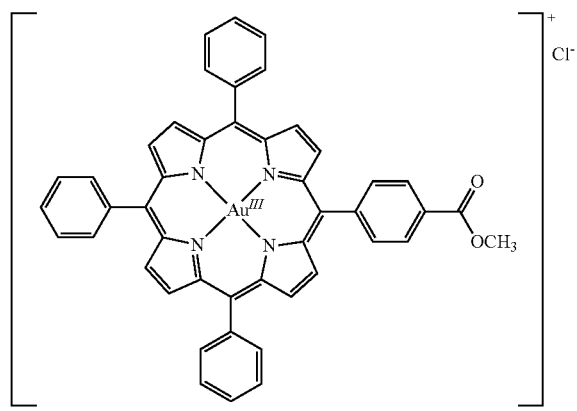

A1

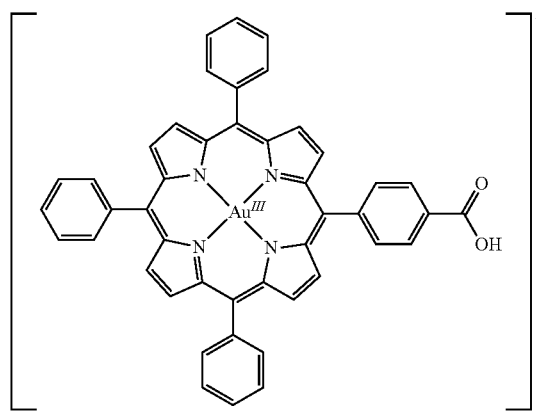

A2

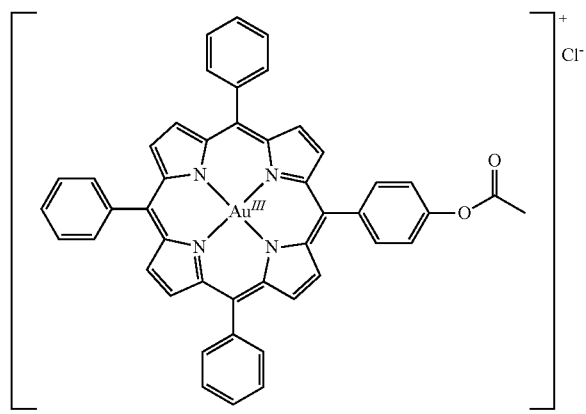

A3

-continued
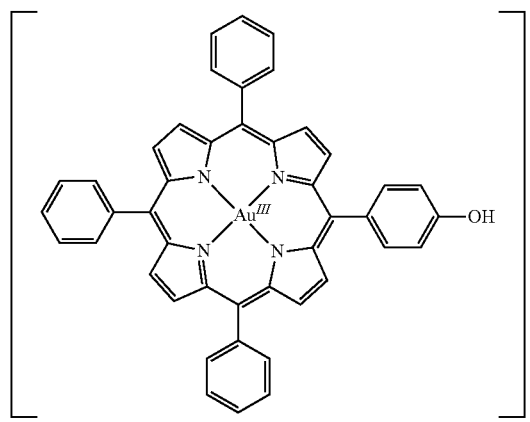
A4
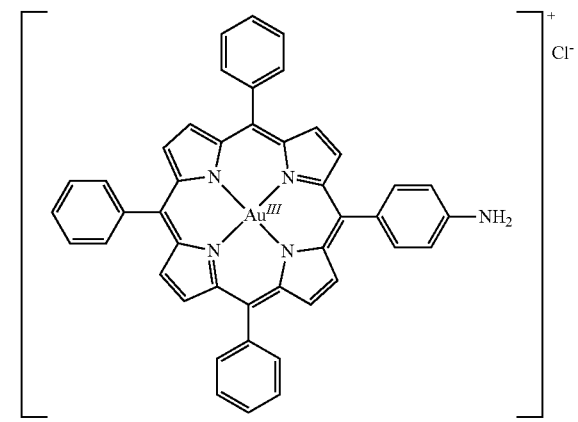
A5
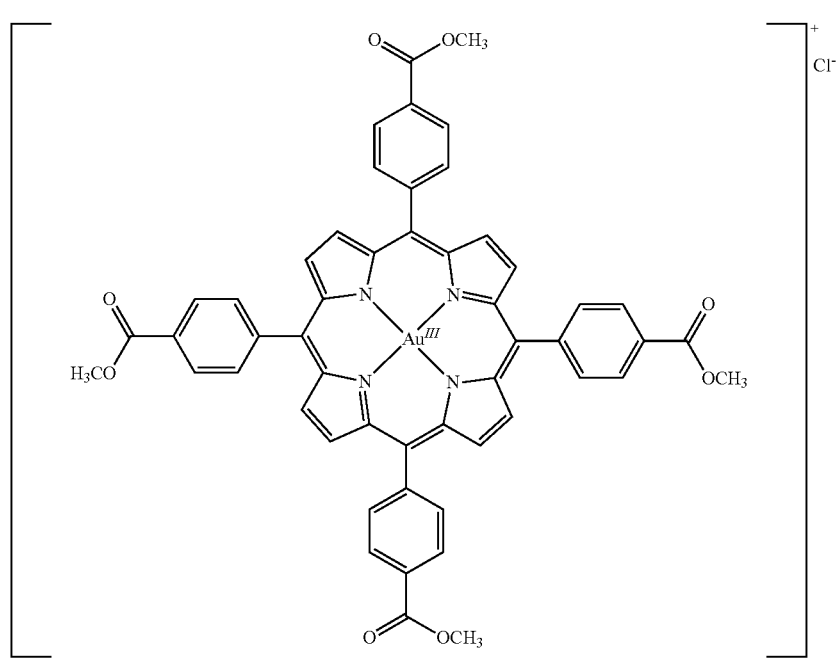
A6

-continued
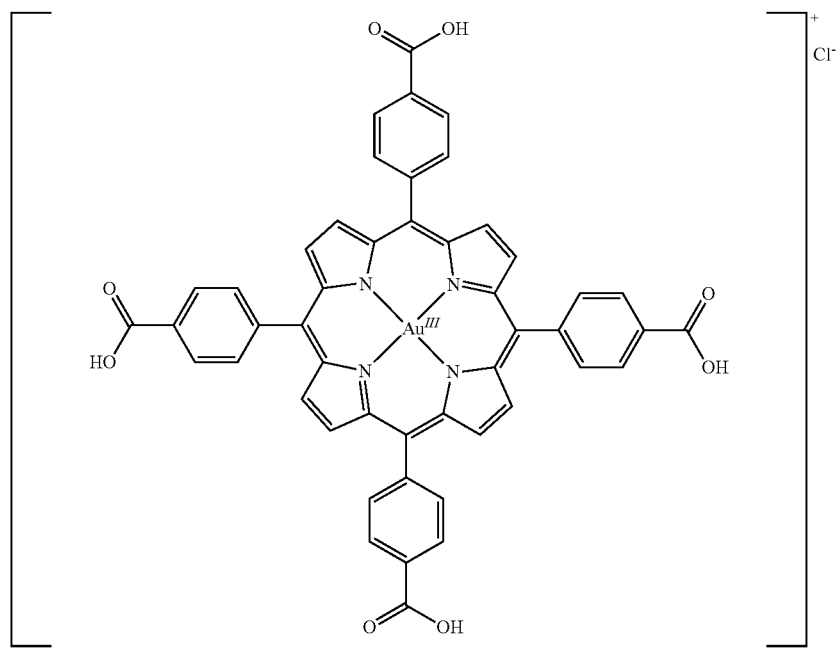
A7
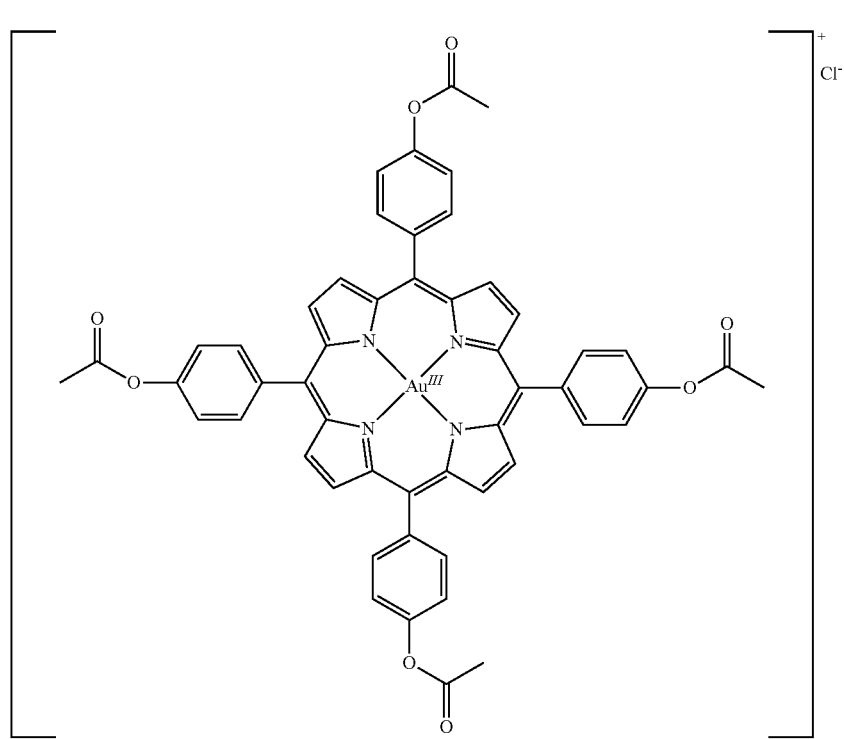
A8

-continued
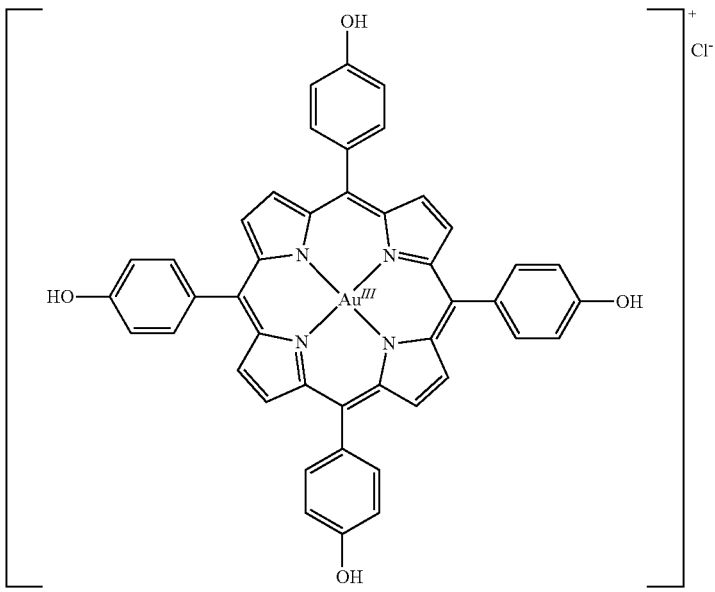
A9
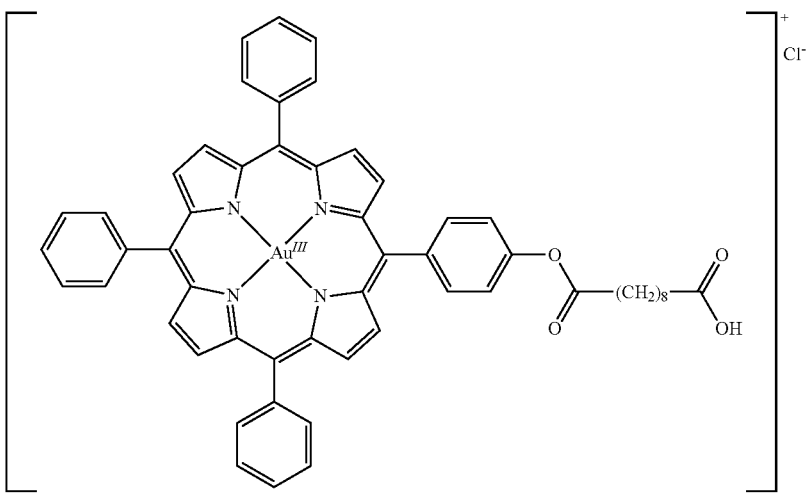
A10
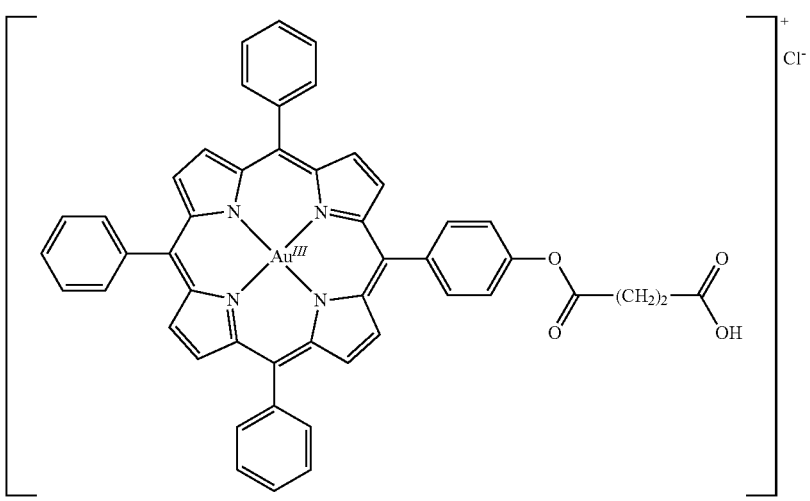
A11

However, gold porphyrin complexes disclosed herein can be used as precursor materials to synthesize GPC with improved therapeutic (for example anti-cancer) and chemical properties.

ii. Gold Porphyrin (GP) Conjugates and Salts Thereof

The GP conjugates are preferably gold(III) porphyrin-PEG (GPP) conjugates. As used herein, the term "gold(III) porphyrin-PEG conjugate" refer to complex of gold(III) metal bound to any porphyrin molecule with structure I shown above, and the complex forms covalent linkage with PEG either directly or through a spacer. In general, the disclosed complexes are gold(III) porphyrin structures without or without reference to the PEG or other conjugated group. In general, the disclosed conjugates are conjugates of gold(III) porphyrin structures conjugated to PEG or another group. The covalent linkages are independently ester, carbonate, carbamate, amide, benzoic-imine, hydrazone, 1,2,3-triazole or thioether.

The disclosed GPP conjugates are decorated with multiple functionalities that provide them with anti-cancer properties (FIG. 1). GPP conjugates show improved chemical properties, for example, improved solubility in aqueous media, as compared to the gold(III) porphyrin complexes without PEG conjugation, antifouling properties, and more importantly amphiphilic character. These properties are important for improving efficacy for anti-cancer treatment with reduced toxic side effects which are the main problem of metal complexes as anti-cancer agents. Also, the linkers for PEG conjugation allow fine-tuning of the release of anti-cancer gold(III) porphyrin moiety from the conjugates and hence the cytotoxicity of the metal complexes. The cytotoxicity of the gold(III) porphyrin-PEG conjugates can be fine-tuned by changing the chemical structures of the linkage. For example, GPP conjugates containing ester linkage show effective killing of the cancer cells without the formation of any toxic side products. This is because PEG pendant can provide steric bulk [Harris, J. M. et al. Nature Rev. Drug Discov. 2003, 2, 214] to inhibit the interactions of gold(III) porphyrin moiety with its molecular target(s). Therefore, to achieve high cytotoxicity toward cancer cells, ester linkage, which can be hydrolyzed readily by intracellular esterase and/or acidic condition in tumor vicinity, can be employed for the conjugation of PEG and gold(III) porphyrin moiety. For example, gold(III) porphyrin-PEG conjugates can be made which include only anti-cancer gold(III) porphyrin moieties, FDA approved PEG pendant and spacer such as sebacic acid. Hydrolysis of the gold(III) porphyrin-PEG conjugates should not form any toxic side product, i.e. no additional toxicity would be found in the conjugates compared to that in gold(III) porphyrin complexes, which is an essence for successful nano-formulations. The chemical structures of exemplary gold(III) porphyrin-PEG conjugates (conjugates 1-6) are shown below, which were synthesized from the precursor gold(III) porphyrin complexes (A1-A11 shown above).

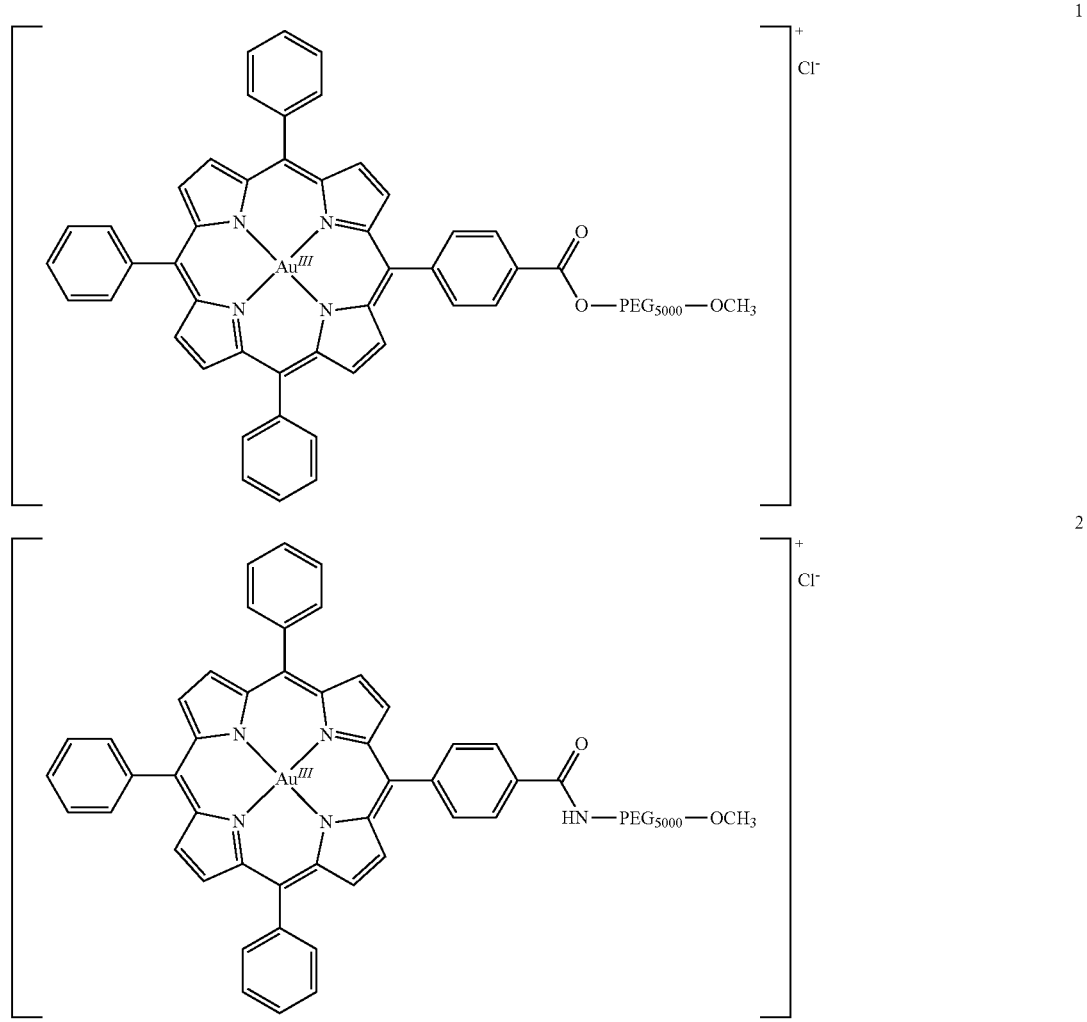

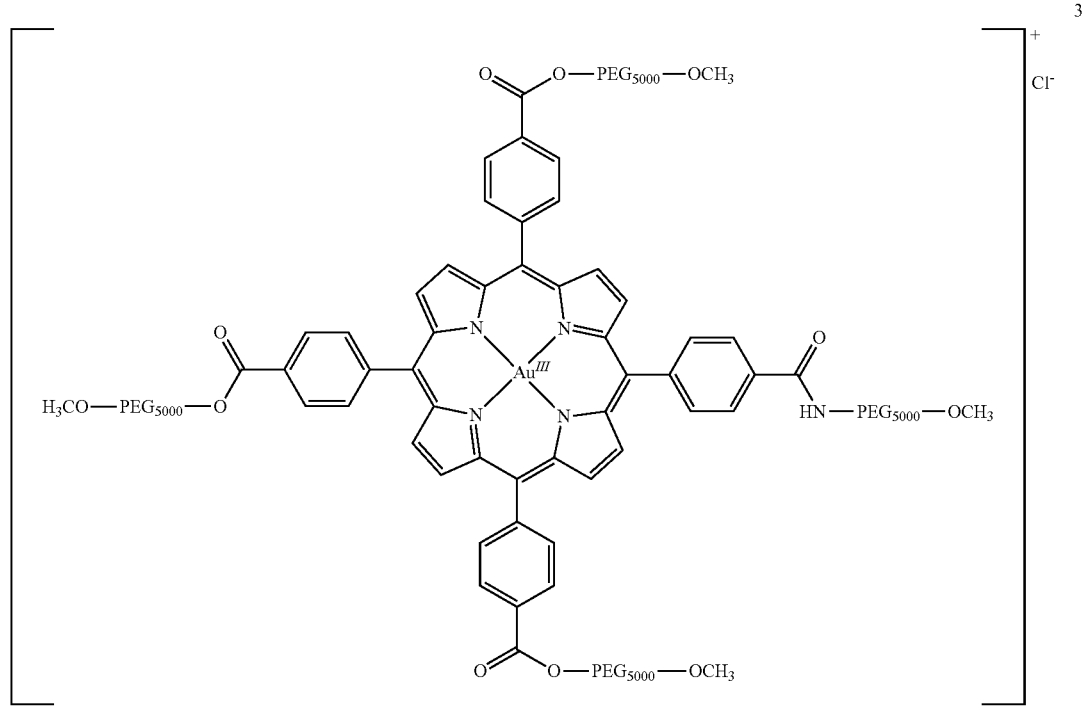
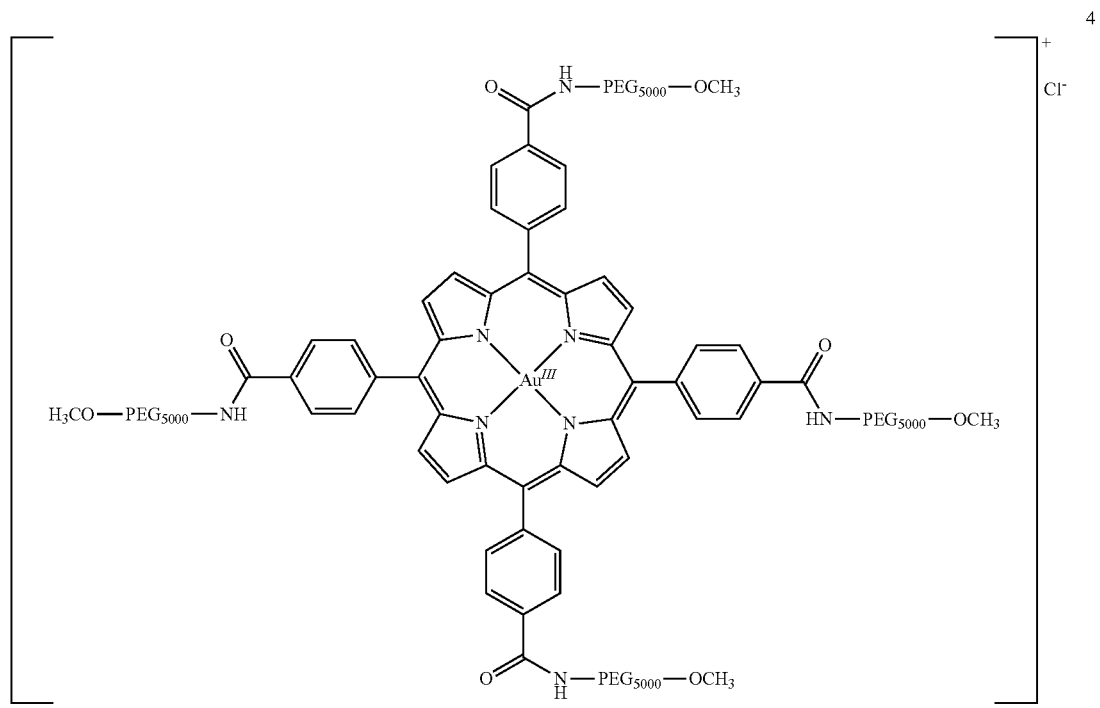

-continued

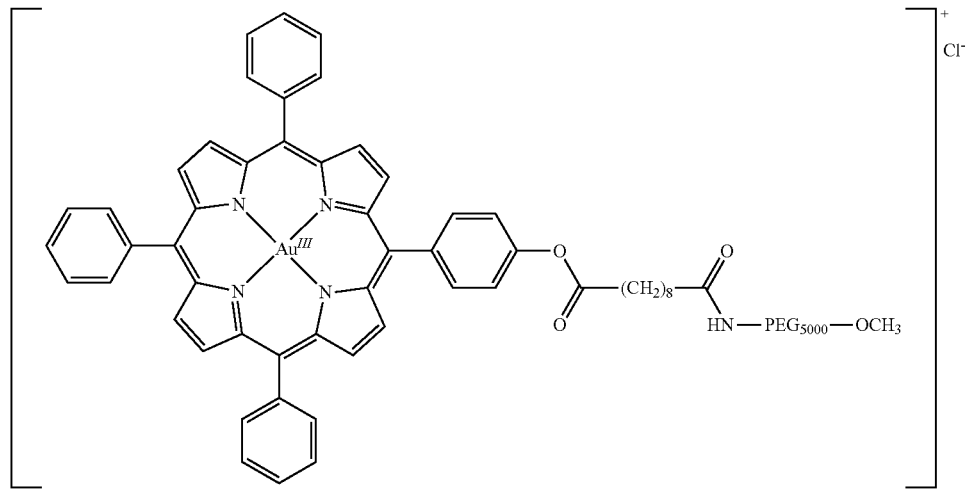

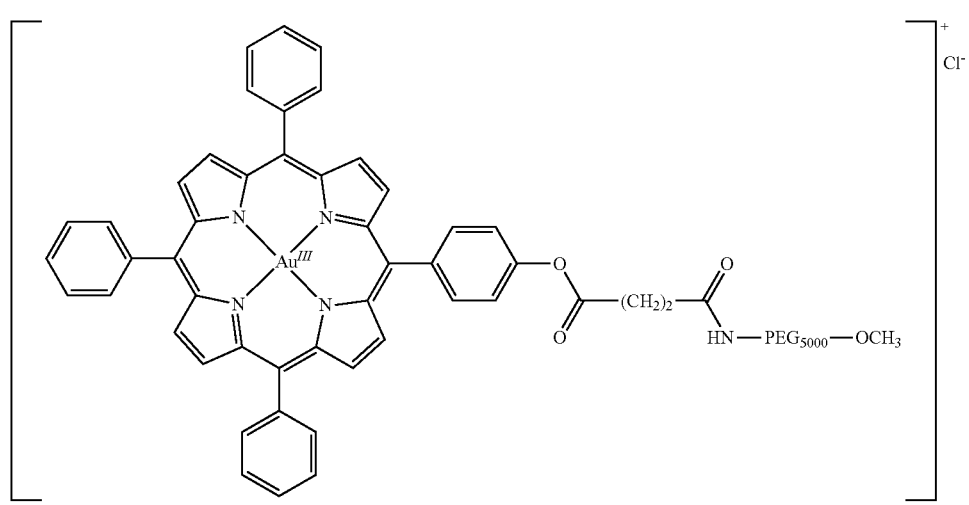

In one embodiment, the gold(III) porphyrin-PEG conjugate is not neutral in charge. For instance, the net positive charge on the gold(III) center can be larger than the absolute net negative charge of the porphyrin-PEG conjugate. In these embodiments, there can be a counter-anion coordinated to the gold(III) complex for charge neutralization. In other embodiments, the GP conjugate is neutral in charge.

2. Pharmaceutically Acceptable Salts

Also disclosed are pharmaceutically acceptable salts of GP conjugates. Examples of pharmaceutically acceptable salts include, but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the GPP conjugates can be synthesized from the parent compound, which contains a basic or acidic moiety, by conventional chemical methods. Generally, such salts can be prepared by reacting the free acid or base forms of these GPP conjugates with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

3. Nano/Microstructures of Gold Porphyrin (GP) Conjugates

The PEG pendant can render gold(III) porphyrin complexes amphiphilic character so that the gold(III) porphyrin-PEG conjugates can undergo self-assembly into nanostructures or microstructures in aqueous media. Through judicious choice of the chemical structures of the porphyrin ligands, the GPP conjugates can form interesting nanostructures in aqueous media without the aid of other components, and this minimizes and/or reduces undesired side effects of anti-cancer treatment.

The nanostructures of GPP conjugates show superior in vitro cytotoxicity toward a panel of cancer cells, including those showing cisplatin- and adriamycin-resistance, when compared to gold(III) porphyrin complexes from which they are made i.e., the precursor gold(III) porphyrin complex 5 which is not conjugated to PEG ("the un-pegylated gold(III) porphyrin complex). Advantageously, they were relatively less toxic toward non-tumorigenic cells, in contrast to the previous studies using gold(III) porphyrin complexes. The selective killing of cancer cells over non-tumorigenic cells has been demonstrated to be based at least on the controlled release properties and the faster cellular uptake of the complexes into cancer cells than that into non-tumorigenic cells, as revealed by inductively coupled plasma mass spectrometry (ICP-MS) and ultra-performance liquid chromatography coupled quadrupole-time-of-flight mass spectrometry (UPLC-QTOF-MS).

4. Nanocomposites of Gold Porphyrin (GP) Conjugates

The disclosed nano/microstructures of GPP conjugates can be used as nanoscale drug carriers for other chemotherapeutics to achieve strong effects on killing cancer cells by the co-delivery, while minimizing toxic side effects. The nano/microstructures of GPP conjugates can also be used to reduce drug resistance to chemotherapeutics, commonly found with administration of the chemotherapeutic alone. Encapsulation of therapeutic agents is exemplified herein with doxorubicin and cytotoxic platinum(II) complexes with N-heterocyclic carbene (NHC) ligands to form nanocomposites. The nanocomposites of 1 and doxorubicin demonstrated synergism in killing cancer cells and could overcome efflux pump-mediated drug-resistance in A2780adr cells which was found in the incubation with doxorubicin alone. Also, the nanocomposites showed slower uptake by non-tumorigenic cells, resulting in a lower toxicity of the nanocomposites toward non-tumorigenic cells. One of ordinary skill in the art would readily expect that the results exemplified herein with doxorubicin and cytotoxic platinum(II) complexes with N-heterocyclic arbine (NHC) can be extrapolated to other chemotherapeutic agents.

Exemplary conventional cancer therapeutics include chemotherapeutic agents, cytokines, and chemokines. The majority of chemotherapeutic drugs can be divided in to: alkylating agents, antimetabolites, anthracyclines, plant alkaloids, topoisomerase inhibitors, and other antitumor agents. All of these drugs affect cell division or DNA synthesis and function in some way. Additional therapeutics include monoclonal antibodies and the new tyrosine kinase inhibitors e.g. the product imatinib mesylate sold under the trade name GLEEVEC® or GLIVEC®, which directly targets a molecular abnormality in certain types of cancer (chronic myelogenous leukemia, gastrointestinal stromal tumors).

Representative chemotherapeutic agents include, but are not limited to doxorubicin, cisplatin, Adriamycin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, the product trastuzumab sold under the trade name HERCEPTIN®, cetuximab, and the product rituximab sold under the trade name RITUXAN® or MABTHERA®, bevacizumab sold under the trade name AVASTIN®, and combinations thereof. Other useful agents include doxil, paclitaxel, camptothecin, irinotecan, berberine chloride, oxaliplatin, carboplatin, auranofin, platinum(II) complexes with N-heterocyclic carbene (NHC) ligands, gold(I) phosphine complexes, gold(I) NHC complexes, cyclometalated gold(III) complexes with NHC ligands and cyclometalated gold(III) complexes with phosphine ligands.

C. FORMULATIONS

The nano/microstructures of the GPP conjugates described herein can be formulated for enteral, parenteral, topical, or pulmonary administration. The GPP conjugates, alone or in combination with one or more therapeutic agents can be combined with one or more pharmaceutically acceptable carriers and/or excipients that are considered safe and effective and may be administered to an individual without causing undesirable biological side effects or unwanted interactions. In a preferred embodiment, the GPP conjugate nano/microstructure is the only nano/microcarrier present in the pharmaceutical formulation in addition with than the active ingredient or ingredient and excipients and or a delivery vehicle, i.e., the formulation does not include nanocarriers or preformed nanostructures, as a result of the auto assembly of GPP conjugates as disclosed herein. Nanocarriers are nanostructures that have the ability to carry and deliver therapeutics to disease sites [Wang, A. Z. et al. *Annu. Rev. Med.* 2012, 63, 185]. With the amphiphilic character, GPP conjugates can undergo self-assembly into nanostructures and this did not require the presence of other surfactants or components for nano-assembly, unlike most conventional drug nano-formulations.

Non-limiting examples of pharmaceutically acceptable carriers that can be used as delivery vehicles include liquids, such as water and oils, including those of petroleum, animal, vegetable, or synthetic origin. Water is a frequently used vehicle when the compound of the invention is administered intravenously. Saline solutions and aqueous dextrose and glycerol solutions can also be employed as liquid vehicles, particularly for injectable solutions.

1. Parenteral Formulations

The GPP conjugates and salts thereof described herein can be formulated for parenteral administration, optionally including one or more therapeutic agents. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the GPP conjugates or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the GPP conjugates or salts thereof, optionally including one or more therapeutic agents, in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

i. Controlled Release Formulations

The parenteral formulations described herein can be formulated for controlled release including immediate release, delayed release, extended release, pulsatile release, and combinations thereof. For parenteral administration, nano/microstructures of the GPP conjugates or the nano/microstructures encapsulating the one or more additional therapeutically active agents can be used to provide controlled release of the GPP conjugate and/or one or more additional active agents as described in the examples. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, one or more additional active agents can be incorporated into nanostructures/nanocomposites of GP conjugates, which provide controlled release of the drug(s). Release of the drug(s) is controlled by diffusion of the drug(s) out of the nanostructures and/or degradation of the polymeric particles by hydrolysis and/or enzymatic degradation.

ii. Injectable/Implantable Formulations

The GPP conjugates, salts thereof and optional one or therapeutic agents (collectively, compounds) and salts thereof described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Enteral Formulations

Oral dosage forms, such as capsules, tablets, solutions, and suspensions, can for formulated for controlled release. For example, the one or more compounds can be formulated into nanoparticles, microparticles, and combinations thereof, and encapsulated in a soft or hard gelatin or non-gelatin capsule or dispersed in a dispersing medium to form an oral suspension or syrup.

In some embodiments, the one or more compounds are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, GPP conjugates, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

a. Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and CARBOPOL® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT T®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT T® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

b. Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

D. METHODS OF MAKING AND USING

1. Methods of Making

Generally, the gold(III) porphyrin-PEG conjugates are synthesized from the precursor gold(III) porphyrin complexes, which can be prepared by the reaction of porphyrin molecules with gold compounds at elevated temperatures, such as 100° C., under acidic conditions [Che, C. M. et al. Chem. Commun. 2011, 47, 9554]. Examples of gold compounds include potassium chloroaurate, sodium chloroaurate, and the like. Examples of porphyrin molecules include 5-(p-methyl carboxyphenyl)-10,15,20-triphenylporphyrin, 5-carboxyphenyl-10,15,20-triphenylporphyrin, 5-hydroxyphenyl-10,15,20-triphenylporphyrin, 5-acetoxyphenyl-10, 15,20-triphenylporphyrin, 5-aminophenyl-10,15,20-triphenylporphyrin, 5,10,15,20-tetra(p-methyl carboxyphenyl)-porphyrin and 5,10,15,20-tetraacetoxyphenylporphyrin.

In one embodiment, the precursor complex is reacted with $H_3CO$-$PEG_{\sim 5000}$—$NH_2 \cdot HCL$ in the presence of N,N'-dicyclohexylcarbodiimide (DCC), 1-hydroxybenzotriazole (HOBt) and diisopropylethylamine (DIPEA) in dichloromethane to form the gold(III) porphyrin conjugate 1 (also referred to simply as 1, herein).

In another embodiment, the precursor complex is reacted with $H_3CO$-$PEG_{\sim 5000}$—$NH_2 \cdot HCL$ in the presence of DCC, HOBt and diisopropylethylamine (DIPEA) in dichloromethane to form the gold(III) porphyrin conjugate 2 (also referred to simply as 2, herein).

In another embodiment, the precursor complex A4 is reacted with sebacic acid, which is a spacer molecule, in the presence of N-(3-dimethylaminopropyl)-N'-ethylcarbodiimide hydrochloride (EDC.HCl), 4-dimethylaminopyridine (DMAP) and trimethylamine in dichloromethane to form an intermediate complex A10.

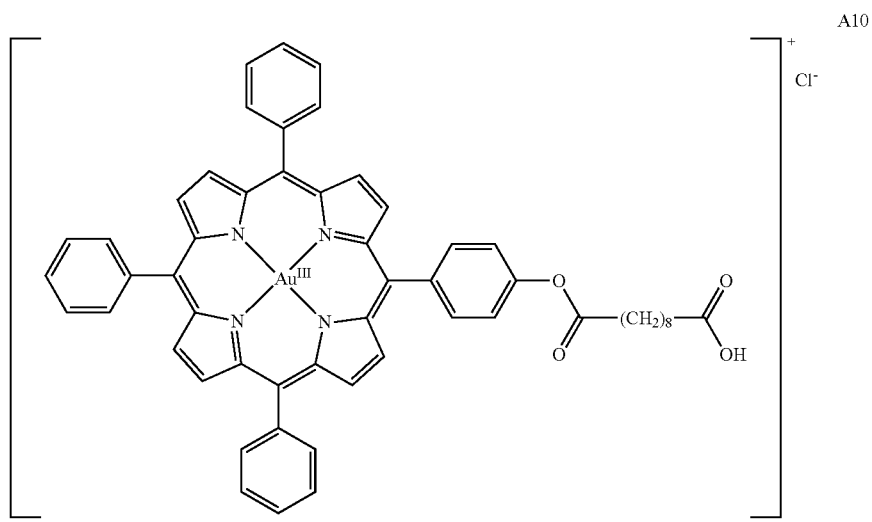

The intermediate complex A10 is then reacted with $H_3CO$-$PEG_{\sim 5000}$—$NH_2 \cdot HCL$ in the presence of DCC, HOBt and diisopropylethylamine (DIPEA) in dichloromethane to form the gold(III) porphyrin conjugate 5 (also referred to simply as 5, herein).

2. Methods of Using

The GP conjugates disclosed herein can be used to induce cancer cell death and hence have applications in cancer therapy. Non limiting examples of subjects who can benefit from the formulations disclosed herein include patients with melanoma, leukemia, colorectal, ovarian carcinoma, nasopharyngeal, hepatocellular, and lung carcinoma. The conjugates can be used alone or in combination with other anticancer therapeutic agents as described herein. The formulations disclosed herein can be used in patients with efflux pump-mediated drug resistance, for example cisplatin- and Adriamycin resistant cancers. The examples show better uptake of test GPP conjugates by an exemplary drug-resistant cell lines (A2780adr), when compared to the gold(III) complexes without PEG conjugation, i.e., the unpegylated gold(III) porphyrin complex. Additionally, GPP nanocomposites incorporating doxorubicin showed synergism with significant reduction of effective dosage for killing A2780adr cells.

The GPP conjugates, alone, or in combination with a second cancer therapeutic can be used for selective targeting of cancer cells, by virtue of the selective uptake of nanostructures of GPP conjugates into cancer cells, when compared to non-cancer cells. The examples show lower uptake of GPP conjugates into non-tumorigenic tissue, exemplified herein by colon and liver cells when compared to the un-pegylated gold(III) porphyrin complex, resulting in significant higher uptake into cancer cells compared to that into non-tumorigenic cells.

When used in combination with one more chemotherapeutic agents, co-delivery of the GPP conjugate can be accomplished in the form of a nanocomposite as described herein. Alternatively, co-delivery can be accomplished by associating/mixing one or more agents to be co-delivered with nano/microstructures of GPP conjugates.

The method for induction of cancer cell death (including but not limited to apoptosis) of cancer cells includes administering to a patient afflicted with a responsive form of cancer a composition comprising an effective amount of one or more gold(III) porphyrin-PEG conjugates. The gold(III) porphyrin-PEG conjugates can be represented by the following structural formula, or a pharmaceutically acceptable salt thereof:

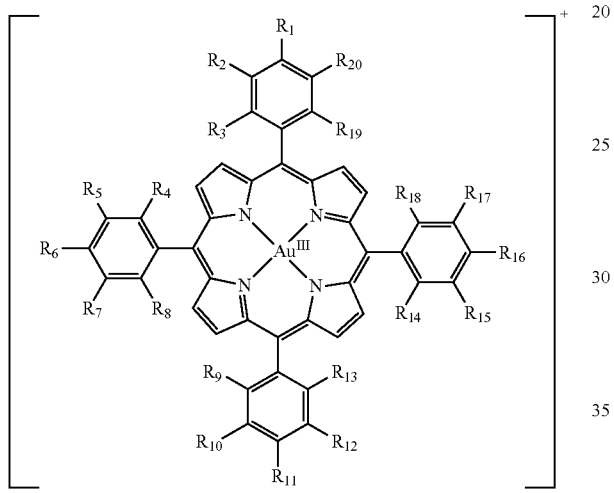

wherein $R_1$-$R_{20}$ are described as above.

In this embodiment, preferred conjugates include conjugates in which $R_1$ is C(O)O-PEG$_{\sim 5000}$—OCH$_3$ and $R_2$-$R_{20}$ are hydrogen (conjugate 1);

C(O)NH-PEG$_{\sim 5000}$—OCH$_3$ and $R_2$-$R_{20}$ are hydrogen (conjugate 2); or OC(O)(CH$_2$)$_8$C(O)NH-PEG$_{\sim 5000}$—OCH$_3$ and $R_2$-$R_{20}$ are hydrogen (conjugate 5).

A combination therapy using the GP conjugates disclosed herein and one or more therapeutic agents in a method for induction of cancer cell death (including but not limited to apoptosis) of cancer cells includes administering to a patient afflicted with a responsive form of cancer a composition comprising an effective amount of nanocomposites formed by encapsulation of one or more therapeutic agents using nanostructures of gold(III) porphyrin-PEG conjugates described herein.

In another preferred embodiment, the method for the induction of cancer cell death includes administering to a patient in need thereof a composition comprising an effective amount of nanocomposites of doxorubicin and gold(III) porphyrin-PEG conjugate (NC1) or a pharmaceutically acceptable salt thereof, wherein $R_1$ is C(O)O-PEG$_{\sim 5000}$—OCH$_3$ and $R_2$-$R_{20}$ are hydrogen.

In another embodiment, a method for the induction of cancer cell death is provided, comprising administering to a patient in need thereof a composition comprising an effective amount of nanocomposites of gold(III) porphyrin-PEG conjugate (NC4) or a pharmaceutically acceptable salt thereof, wherein $R_1$ is C(O)O-PEG$_{\sim 5000}$—OCH$_3$ and $R_2$-$R_{20}$ are hydrogen, and chemotherapeutic platinum(II) complexes with NHC ligand (Pt-1a) with the following structure formula:

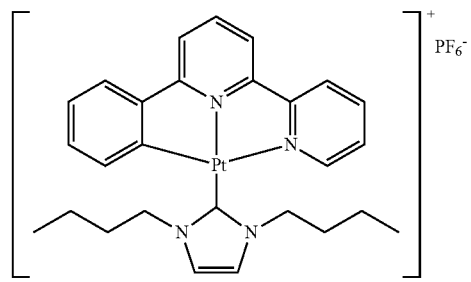

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

EXAMPLES

Example 1: Preparation and Characterization of Gold(III) Porphyrin-PEG Conjugates In general, the syntheses of gold(III) porphyrin precursor complexes and gold(III) porphyrin-PEG conjugates were conducted under an inert atmosphere of nitrogen using Standard Schlenk technique. $^1$H NMR spectra were recorded with a Bruker AVANCE 400 (400 MHz) or DPX-300 (300 MHz) Fourier transform NMR spectrometer at ambient temperature with tetramethylsilane (Me$_4$Si) as an internal reference. MALDI-TOF MS were recorded on a ABI4800 MALDI TOF/TOF™ Analyzer using α-cyano-4-hydroxycinnamic acid with sodium trifluoroacetate as the matrix.

Synthesis and Characterization of Gold(III) Porphyrin-PEG Conjugate 1

Complex A2 (22 mg, 0.026 mmol), HOBt (2.4 mg, 0.018 mmol) and PEG$_{5000}$—OCH$_3$ (124 mg, 0.025 mmol) were dissolved in anhydrous dichloromethane. With stirring at 0° C., DCC (5.1 mg, 0.025 mmol) in dichloromethane was added to the solution mixture, followed by the addition of triethylamine (7.2 µL, 0.052 mmol). The solution mixture was then stirred at 0° C. for 2 h, and allowed to warm to room temperature and reacted for 5 days. After evaporation of volatile solvent under reduced pressure, the crude product was dissolved in deionized water, and undissolved solid was filtered. The aqueous solution was extracted with dichloromethane twice, and the combined organic layers were washed with dilute HCl$_{(aq)}$ solution twice followed by saturated NaCl$_{(aq)}$ solution. The organic layer was then dried over anhydrous sodium sulfate, filtered, and evaporated under reduced pressure. The crude product was dissolved in minimum amount of dichloromethane, and precipitated as a red solid by dropwise addition of the dichloromethane solution to diethyl ether. The red solid obtained after precipitation for totally three times was further purified by column chromatography on neutral alumina, using dichloromethane and methanol (50:1, v/v) as eluent. The product was obtained as red solid. Yield=115 mg (78%). $^1$H NMR (400 MHz, CDCl$_3$, 298 K: δ=3.36 (s, 3H, —CH$_2$CH$_2$OCH$_3$), 3.44-3.89 (br, —CH$_2$CH$_2$O—), 3.98 (t, J=4.8 Hz, 2H, —COOCH$_2$CH$_2$O—), 4.67 (t, J=4.8 Hz, 2H, —COOCH$_2$CH$_2$O—), 7.83-7.92 (m, 9H, phenyl H), 8.22-8.24 (m, 6H, phenyl H), 8.34 (d, J=8.0 Hz, 2H, —C$_6$H$_4$COO—), 8.54 (d, J=8.0 Hz, 2H, —C$_6$H$_4$COO—), 9.20, (d, J=5.2 Hz, 2H, pyrrolic H), 9.27-9.29 (m, 6H, pyrrolic MALDI-TOF MS: M$_n$=5897 g mol$^{-1}$, M$_w$=5971 g mol$^{-1}$, PDI=1.01.

Synthesis and Characterization of Gold(III) Porphyrin-PEG Conjugate 2

The procedure was similar to that of conjugate 1, except that H$_3$CO-PEG$_{~5000}$—NH$_2$·HCl (124 mg, 0.025 mmol) was used instead of HO-PEG$_{~5000}$—OCH$_3$. The red solid obtained after precipitation was further purified by column chromatography on neutral alumina, using dichloromethane and methanol (50:1, v/v) as eluent. The product was obtained as red solid. Yield=88 mg (60%). $^1$H NMR (400 MHz, CDCl$_3$, 298 K): δ=3.38 (s, 3H, —CH$_2$CH$_2$OCH$_3$), 3.50-3.82 (br, —CH$_2$CH$_2$O—), 3.88 (br, 4H, —CONHCH$_2$CH$_2$O—), 7.83-8.00 (m, 9H, phenyl 11), 8.19-8.28 (m, 6H, phenyl 11), 8.30 (d, J=8.2 Hz, 2H, —C$_6$H$_4$CONH—), 8.39 (s, 1H, —CONHCH$_2$CH$_2$O—), 8.53, (d, J=8.2 Hz, 2H, —C$_6$H$_4$CONH—), 9.24-9.38 (m, 8H, pyrrolic MALDI-TOF MS: M$_n$=6020 g mol$^{-1}$.

Synthesis and Characterization of Gold(III) Porphyrin-PEG Conjugate 5

The gold(III) porphyrin precursor complex A4 (50 mg, 0.058 mmol), DMAP (0.89 mg, 7.26 μmol) and sebacic acid (58.6 mg, 0.290 mmol) were dissolved in anhydrous dimethylformamide-dichloromethane solution mixture (10:1, v/v; 20 mL). With stirring at 0° C., EDC.HCl (55.7 mg, 0.290 mmol) in dimethylformamide-dichloromethane solution mixture was added to the solution mixture, followed by the addition of triethylamine (40.2 μL, 0.290 mmol). The solution mixture was then stirred at 0° C. for 2 h, and allowed to warm to room temperature and reacted overnight. After evaporation of volatile solvent under vacuum, the crude product was dissolved in dichloromethane and washed with dilute HCl$_{(aq)}$ solution twice followed by saturated NaCl$_{(aq)}$ solution. The organic layer was then dried over anhydrous sodium sulfate, filtered, and evaporated under reduced pressure. The crude product was purified by column chromatography on silica gel, using dichloromethane and methanol (50:3, v/v) as eluent. The product A10 was obtained as dark purple solid with a yield of 70%. $^1$H NMR (300 MHz, CDCl$_3$, 298 K): δ=1.30-1.65 (br, 10H, —CH$_2$—), 1.90 (m, 2H, —C$_6$H$_4$OC(═O)CH$_2$CH$_2$—), 2.33 (t, J=7.3 Hz, 2H, —CH$_2$CH$_2$COOH), 2.77 (t, J=7.0 Hz, 2H, —C$_6$H$_4$OC(═O)CH$_2$CH$_2$—), 7.62 (d, J=8.3 Hz, 2H, phenyl H), 7.75-7.95 (m, 9H, phenyl 11), 8.18-8.26 (m, 6H, phenyl 11), 8.29 (d, J=8.3 Hz, 2H, phenyl H), 9.26-9.33 (m, 6H, pyrrolic 11), 9.36 (d, J=6.2 Hz, 2H, pyrrolic 11).

The gold(III) porphyrin-PEG conjugate 5 was synthesized by the reaction between the precursor complex A10 and H$_3$CO-PEG$_{~5000}$—NH$_2$·HCl. The procedure was similar to that of conjugate 2, except that A10 (27.2 mg, 0.026 mmol) was used instead of A2. The product was obtained as a red solid, with a yield of 74%. $^1$H NMR (400 MHz, CDCl$_3$, 298 K): δ=1.20-2.21 (br, 12H, —CH$_2$—), 2.40 (br, 2H, —CH$_2$CH$_2$CONH—), 2.77 (br, 2H, —C$_6$H$_4$OC(═O) CH$_2$CH$_2$—), 3.38 (s, 3H, —CH$_2$CH$_2$OCH$_3$), 3.40-4.00 (br, —CH$_2$CH$_2$O—), 7.43-7.46 (br, 2H, phenyl H), 7.87-7.90 (br, 9H, phenyl H), 8.20-8.32 (br, 8H, phenyl H), 9.29-9.32 (br, 8H, pyrrolic H).

Example 2: Self-Assembly of Gold(III) Porphyrin-PEG Conjugates

The PEG pendant renders the gold(III) porphyrin-PEG conjugates amphiphilic character (FIG. 3). Therefore, they can undergo self-assembly in aqueous media, through non-covalent interactions, to form interesting nanostructures. Representative examples are conjugates 1 and 2. They were found to form core-shell micelles with diameters of ca. 120 and 200 nm, respectively, as revealed by images of transmission electron microscopy, by adding their respective acetonitrile solutions into phosphate buffered saline (PBS) followed by evaporation of the volatile solvent. Intensity-averaged signals from dynamic light scattering (DLS) experiments of 1 and 2 were found to be 120.8±7.2 nm and 177.1±81.2 nm respectively, while the zeta potentials of the nanostructures of 1 and 2 were −0.1±1.6 mV and −0.7±4.2 mV. The good agreement of the intensity-averaged signals from the DLS experiments with the diameters of the nanostructures observed in TEM images suggested the signals corresponding to the hydrodynamic diameters of the nanostructures of 1 and 2. On the other hand, the almost neutral zeta potentials of the nanostructures of 1 and 2 validated the presence of the PEG pendant in the shell of the nanostructures. The identity of gold species in the core of the nanostructures was supported by the good contrast of the core in the TEM images and energy-dispersive X-ray (EDX) spectra of nanostructures of 1.

Example 3: Gold(III) Porphyrin-PEG Conjugates Exhibit Controlled Release Properties To achieve promising anti-cancer activities, the conjugates should undergo hydrolysis in cancer cells to release chemotherapeutic gold(III) porphyrin moieties, so that PEG pendant would not prohibit the binding of gold(III) porphyrin moieties with their therapeutic target(s). Therefore, the rate of release of gold(III) porphyrin moiety from the conjugates in aqueous buffer solutions at different pH values was investigated. 1 and 2 were dissolved in PBS solution (pH 7.4) or sodium acetate buffer solution (pH 4.0) and dialyzed against a large volume of the PBS or sodium acetate buffer solution in dark at 37° C. using a 1,000 Da cut-off membrane. The quantity of the released gold(III) porphyrin moiety at different time points was determined by inductively coupled plasma mass spectrometry (ICP-MS). In PBS solution, 31% and 60% of 1 were hydrolyzed at 6 and 24 h respectively, while only 2% and 3% of hydrolyzed product of 2 were found at the corresponding time interval, and more than 89% of 2 remained unhydrolyzed at 96 h. On the other hand, the release of gold(III) porphyrin moiety from 1 was found to be faster in more acidic sodium acetate buffer solution (pH 4), with 60% and 96% of hydrolyzed product found at 6 and 24 h respectively. As the only difference of 1 from 2 is the chemical structure of the linkage for conjugation, the faster release of gold(III) porphyrin moiety from 1 in PBS solution than that from 2 should be attributed to the higher tendency of the ester bond in 1 to undergo hydrolytic cleavage than the amide bond in 2. For the faster release from 1 in more acidic sodium acetate buffer solution than that in PBS solution, this should be ascribed to the acid-catalyzed hydrolysis of the ester bond in 1, resulting in almost complete cleavage of the PEG pendant from the conjugate after 24 h.

Figure 2:
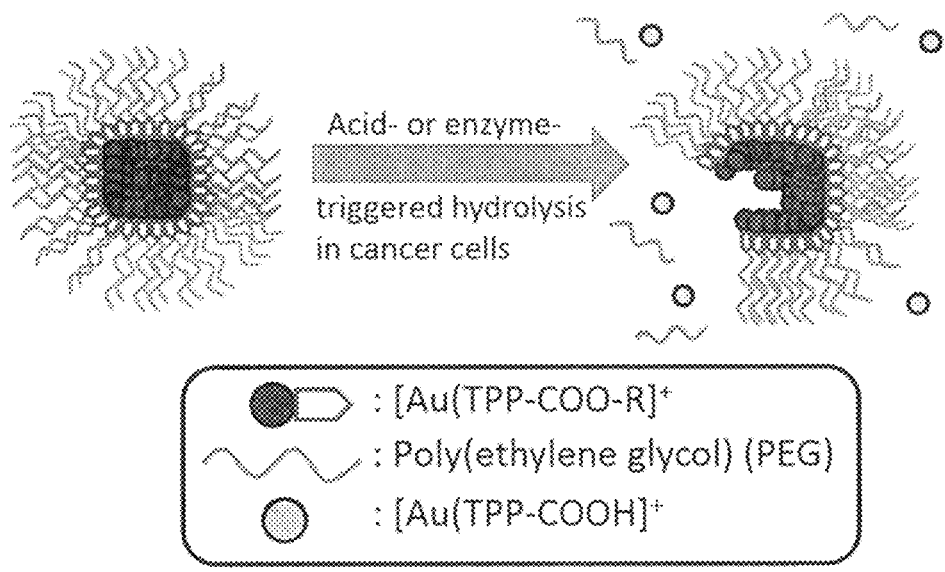
FIG. 2 is a schematic cartoon showing the release of chemotherapeutic gold(III) porphyrin moiety from the conjugate upon hydrolysis of the ester linkage.

Hydrolysis of the gold(III) complexes in live cells has been studied by ultra-performance liquid chromatography coupled quadrupole-time-of-flight mass spectrometry (UPLC-QTOF-MS). Colon cancer cells, HCT116, were treated with 1 and A1 (2 μM) for 24 h, harvested and lysed by acetonitrile-water solution mixture (3:1, v/v) prior to UPLC-QTOF-MS analysis. The total-ion chromatogram of cell lysates of HCT116 treated with 1 showed a peak with retention time of 6.44 min, in addition to the peaks found in the chromatogram of untreated cells. It is noteworthy that this peak was not found in the total-ion chromatogram of 1 in acetonitrile solution, while A2 in acetonitrile solution showed a peak with almost the same retention time ($R_t$=6.39 min) in its total-ion chromatogram. Selected-ion chromatogram of cell lysates of HCT116 treated with 1 at m/z=853 revealed a peak with same retention time ($R_t$=6.44 min) as the total-ion chromatogram, and the mass spectra of the peak showed the same isotopic pattern as that of [Au(TPP—COOH)]$^+$. For cell lysates of HCT116 treated with A1, peaks with retention time of 6.42 and 9.94 min were found in its total-ion chromatogram, with m/z of 853 and 867 respectively as revealed by the selected-ion chromatograms. The MS of the peaks at 6.42 and 9.94 min were found to have the same isotopic patterns as those of [Au(TPP—COOH)]$^+$ and [Au(TPP—COOCH$_3$)]$^+$ respectively. In view of the fact that the peak with retention time of 6.44 min in the total-ion chromatogram of cell lysates of HCT116 treated with 1 was absence in the total-ion chromatogram of 1 in acetonitrile solution, this peak should be owing to the metabolite of 1 formed in HCT116 cells. As this peak showed almost the same retention time of the peak of A2 in acetonitrile solution and its mass spectrum revealed the same isotopic pattern as that of [Au(TPP—COOH)]$^+$, this peak should originate from the chemical species of [Au(TPP—COOH)]$^+$, suggesting the hydrolysis of ester bond of 1 in HCT116 cells with the formation of [Au(TPP—COOH)]$^+$ (FIG. 2). The hydrolysis of ester bond of ester derivative of gold(III) porphyrin complex in HCT116 cells was further confirmed by the study of A1, which showed the emergence of the peak with retention time of 6.42 min in the total-ion chromatogram and good agreement of the mass spectrum of the peak with the isotopic pattern of [Au(TPP—COOH)]$^+$.

Figure 3A:
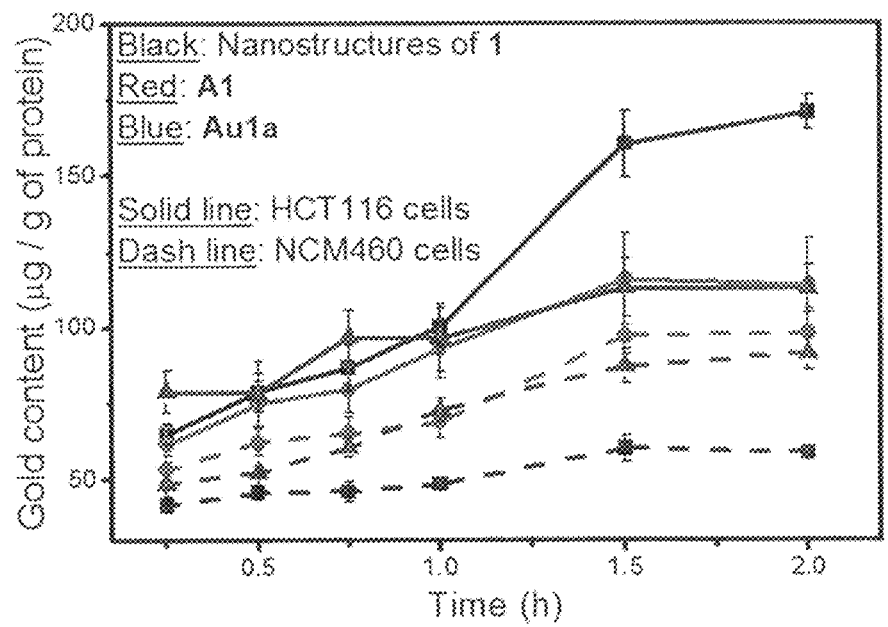
FIG. 3A shows the cellular uptake of 1 (squares), A1 (circles) and Au1a (triangles) (2 μM) into HCT116 cells (solid lines) and NCM460 cells (dashed lines), respectively, after incubation at 37° C. for indicated time intervals.
Figure 3B:
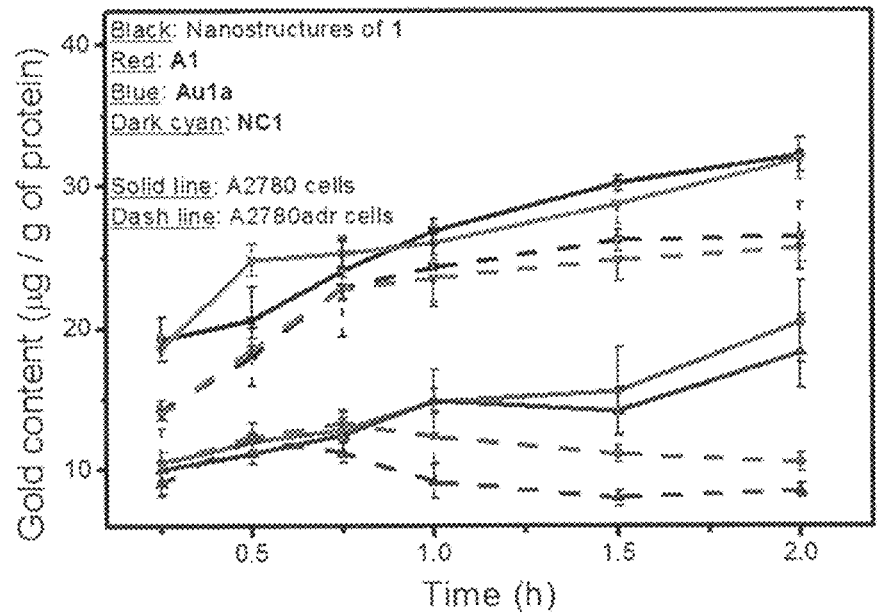
FIG. 3B shows the cellular uptake of the complexes 1 (squares), A1 (circles) and Au1a (triangles) and NC1 (upside-down triangles) (2 μM) into A2780 cells (solid lines) and A2780adr cells (dashed lines), respectively, after incubation at 37° C. for indicated time intervals.
Figure 3C:
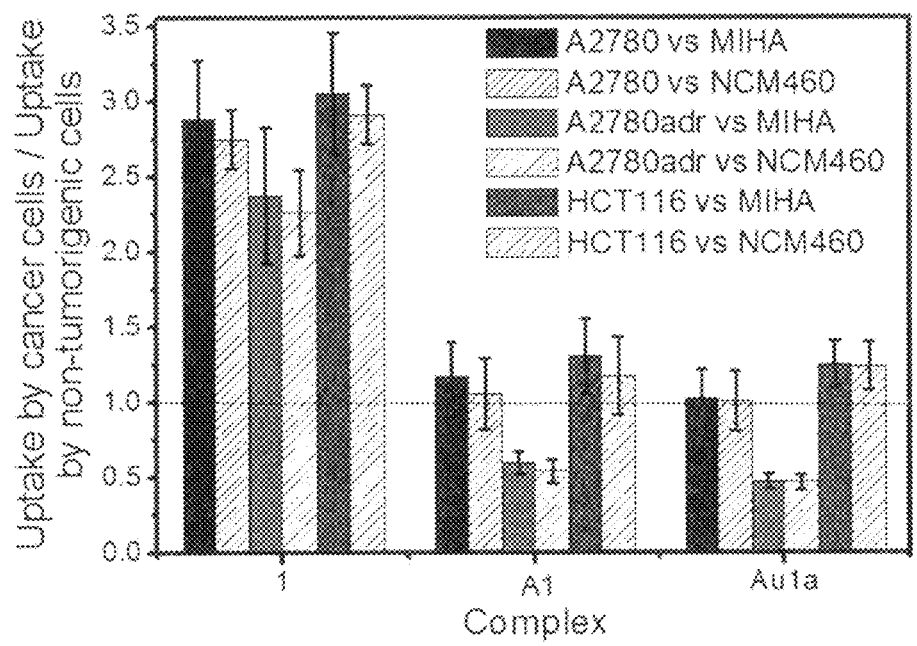
Figure 3D:
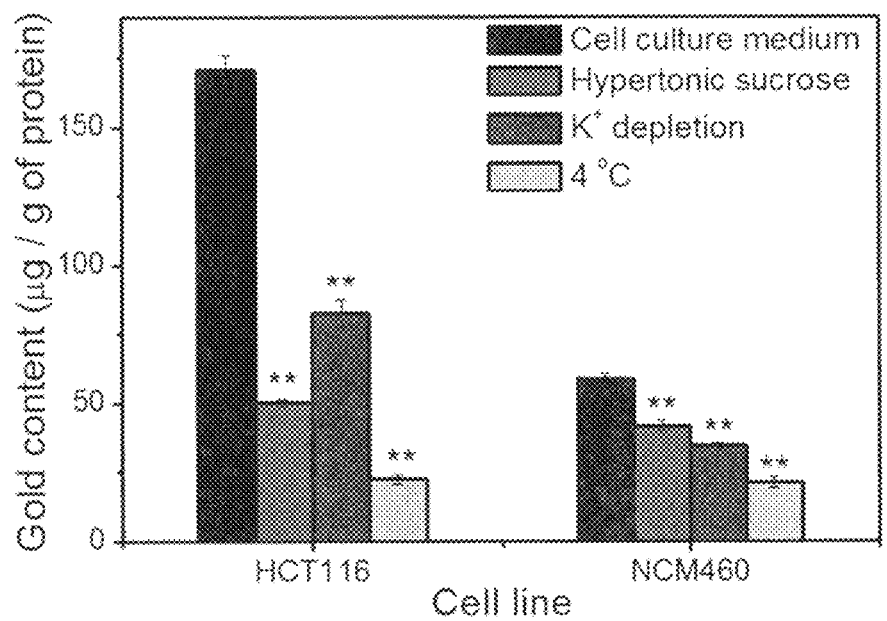
FIG. 3D shows the cellular uptake of 1 into HCT116 and NCM460 cells after incubation for 2 h in cell culture medium with 10 vol % fetal bovine serum at 37° C. (first bar in both series), cell culture medium with 10 vol % fetal bovine serum and 0.45 M sucrose at 37° C. (second bar in both series), aqueous buffer solution (140 mM NaCl, 20 mM HEPES, 1 mM $CaCl_2$, 1 mM $MgCl_2$ and 1 g/L D-glucose, pH 7.4) at 37° C. (third bar in both series), and cell culture medium with 10 vol % fetal bovine serum at 4° C. (fourth bar in both series), respectively. All the data are shown as mean±SEM from three independent experiments.

Example 4: Gold(III) Porphyrin-PEG Conjugates Show Faster Cellular Uptake into Human Cancer Cells than Non-Tumorigenic Cells The uptake of conjugate 1, precursor complex A1, and Au1a by cancer cells and non-tumorigenic cells was studied by the analysis of cell lysates of treated cells using ICP-MS. 1 was found to show faster cellular uptake into a variety of cancer cells, such as the colorectal carcinoma (HCT116), human ovarian carcinoma (A2780) and the drug-resistant derivatives (A2780adr), than the gold(III) complexes without PEG conjugation, i.e. A1 and Au1a (FIG. 3a-c). Interestingly, the uptake of 1 into non-tumorigenic colon and liver cells (NCM460 and MIHA respectively) was found to be lower than that of A1 and Au1a (FIGS. 3a and 4), resulting in significant higher uptake into cancer cells compared to that into non-tumorigenic cells (FIG. 3c). On the other hand, the uptake of 1 into cancer cells showed a large dependence on temperature, compared to the uptake of A1 (FIGS. 3d and 5). Based on the results of previous study on cellular uptake of nanostructures [Davis, M. E. et al. *Nat. Rev. Drug Discov.* 2008, 7, 771] and the strong dependence of the uptake mechanism of 1 on temperature, K$^+$ concentration and hypertonic condition (FIG. 3d), nanostructures of 1 likely entered live cells by clathrin-mediated endocytosis. Due to the generally higher metabolic rate of cancer cells than normal cells, 1 showed faster accumulation in cancer cells than non-tumorigenic cells (FIG. 3a-c). It is worth noting that 1 showed increasing concentration in A2780adr cells with time, while A1 and Au1a revealed decreases in amount after incubation for 0.75 and 0.5 h respectively (FIG. 3b). The decreases in content of A1 and Au1a in A2780adr cells were likely due to the P-glycoprotein-mediated drug-resistance of A2780adr cells, and the accumulation of 1 in A2780adr cells suggested that the nanostructures of 1 could help to overcome the efflux pump-mediated drug-resistance of A2780adr cells.

Figure 6A:
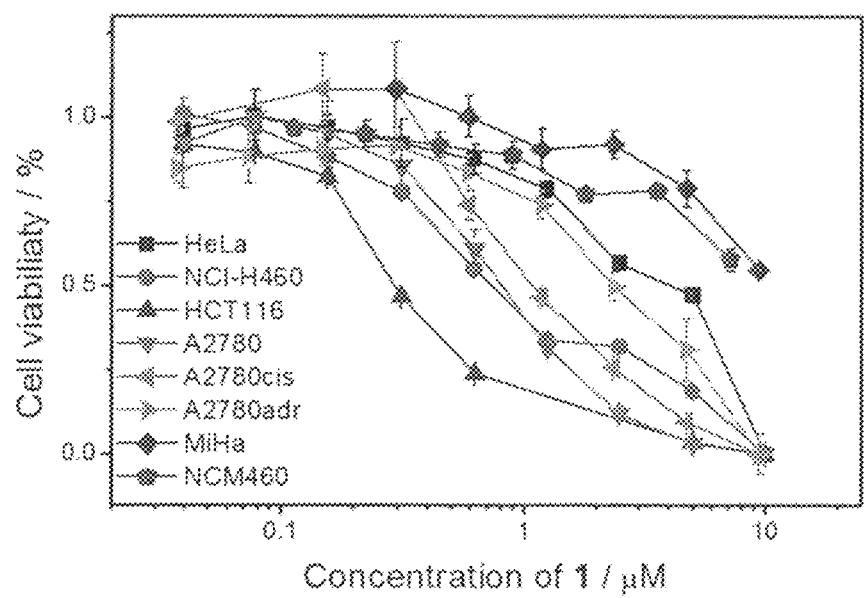
FIGS. 6A and 6B show the cell viability upon treatment with different concentrations of (6A) nanostructures of 1 and (6B) NC1 for 72 h.

Example 5: Gold(III) Porphyrin-PEG Conjugates Exert Potent In Vitro Cytotoxicity Against Human Cancer Cells with Lower Toxicities Toward Non-Tumorigenic Cells The in vitro cytotoxicity of 1, 2 and 5 toward human cancer cell lines (HeLa, NCI-H460, HCT116, A2780) and the cisplatin- and adriamycin-resistant cancer cell lines (A2780cis and A2780adr), as well as normal human colon mucosal epithelial cell line (NCM460), non-tumorigenic immortalized liver cells (MIHA) and normal lung fibroblast cells (CCD-19Lu) was evaluated by 3-(4,5-dimethyl-2-thiazolyl)-2,5-diphenyltetrazolium bromide (MTT) assay (Table 1; FIG. 6a). The in vitro cytotoxicity of gold(III) porphyrin complex Au1a and the precursor complexes A1, A4 and A10 as well as clinically approved chemotherapeutic agents (cisplatin and doxorubicin (DOX)) were also studied for comparison (Table 1). The conjugates with ester linkage 1 and 5, Au1a, and precursor complexes A1, A4 and A10 both demonstrated superior in vitro cytotoxicity toward cancer cells, compared to that of cisplatin (1 is 5.1-76.9 times more cytotoxic than cisplatin). It is worth noting that 1 and A1 retained most of its activity in killing drug-resistant cancer cells, A2780cis and A2780adr, while Au1a, DOX and cisplatin were found to show lower cytotoxicity toward A2780adr compared to the non-resistant A2780 cells (Table 2). For non-tumorigenic cells, A1, A4, A10 and Au1a showed IC$_{50}$ in submicromolar range, in consistent with the reported high toxicity of gold(III) porphyrin complexes toward normal cells. Interestingly, 1 and 5 were found to be relatively non-toxic toward non-tumorigenic MIHA and NCM460 cells (Table 1), as revealed by the much larger values of the ratio of IC$_{50}$ toward non-tumorigenic cells to that toward cancer cells (Table 3 and 4). On the other hand, the conjugate with amide linkage, 2, was found to be less cytotoxic toward both cancer and non-tumorigenic cells in vitro.

Figure 5:
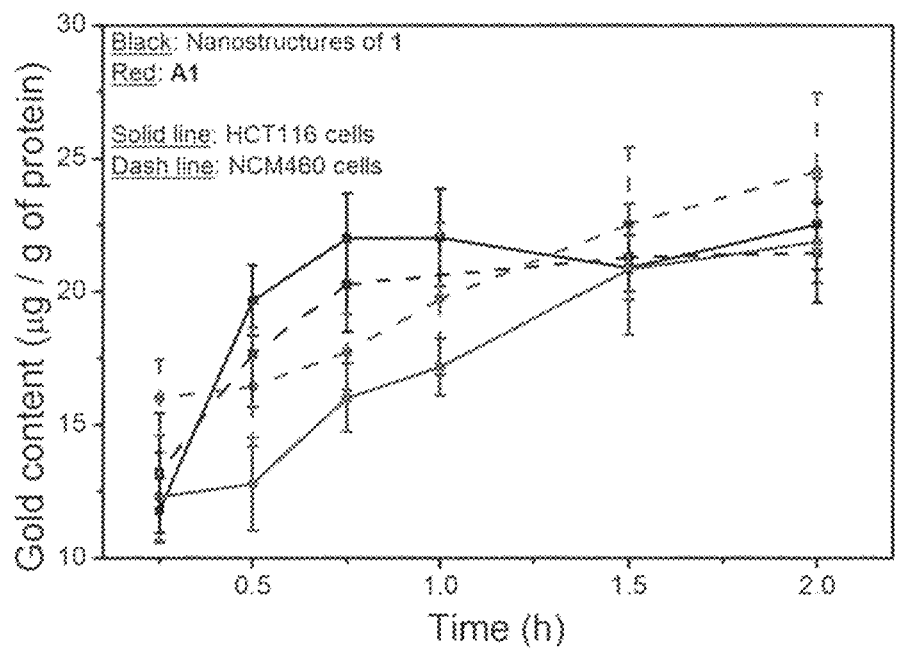
FIG. 5 shows the cellular uptake of 1 (squares) and A1 (circles) (2 μM) into HCT116 cells (solid lines) and NCM460 cells (dashed lines), respectively, after incubation at 4° C. for indicated time intervals.
Figure 6B:
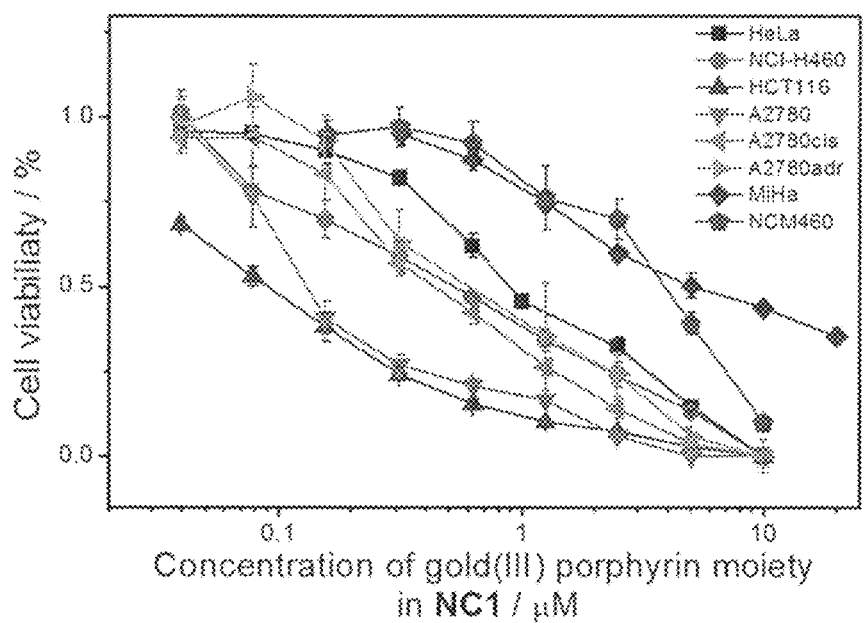

The controlled release property of 1 and its higher cellular uptake by cancer cells (FIG. 3-5) would probably account for the observed higher in vitro cytotoxicity of 1 toward cancer cells than that toward non-tumorigenic cells (Table 3 and 4). Based on the generally higher metabolic rate of cancer cells, the nanostructures of 1 showed faster accumulation in cancer cells than non-tumorigenic cells. The higher metabolic rate, together with the acidic character of cancer cells, would favor the hydrolysis of 1, leading to a higher rate of release of anti-cancer gold(III) porphyrin moiety in cancer cells. On the other hand, 1 in non-tumorigenic cells would be hydrolyzed less readily, and the unhydrolyzed gold(III) porphyrin-PEG conjugates should show low toxicity, as supported by the MTT assays of 2 which has a less cleavable amide linkage. This would be attributed to the steric bulk of PEG pendant inhibiting interactions of gold (III) porphyrin moiety with its molecular target(s), resulting in a much lower in vitro cytotoxicity of the conjugate than the hydrolyzed product. As a result, the higher uptake into cancer cells and likely faster hydrolytic cleavage of the PEG pendant should account for the more effective killing of cancer cells than non-tumorigenic cells by 1 (FIGS. 6a and 6b; Table 1, 3 and 4).

For the gold(III) porphyrin complexes without PEG conjugation, i.e. A1 and Au1a, they demonstrated high in vitro cytotoxicity toward both cancer and non-tumorigenic cells (Table 1, 3 and 4). This can be explained by their similar cellular uptake into cancer and non-tumorigenic cells (FIGS. 3a-c and 4), resulting in non-selective killing of cancer and non-tumorigenic cells.

TABLE 3-continued

Relative toxicity of 1, 2, A1 and Au1a toward cancer cells and NCM460 cells

| Compounds/ nanostructures | Toxicity toward cancer cells compared to that toward NCM460 cells[a] | | | | | |
|---|---|---|---|---|---|---|
| | HeLa | NCI-H460 | HCT-116 | A2780 | A2780cis | A2780adr |
| 2 | 1.5 | 2.9 | 8.6 | 5.3 | 1.5 | <0.6 |
| A1 | 0.2 | 1.3 | 1.4 | 0.7 | 0.7 | 0.2 |
| Au1a | 0.1 | 0.3 | 0.8 | 0.6 | 0.4 | 0.06 |

[a]Determined by $IC_{50}$ of non-tumorigenic NCM460 cells/$IC_{50}$ of cancer cells

TABLE 1

In vitro cytotoxicity of 1, 2, 5, A1, A4, A10, Au1a, DOX, nanocomposites of 1 and DOX (NC1), and cisplatin.

| Compound | $IC_{50}$[a]/μM | | | | | | | | |
|---|---|---|---|---|---|---|---|---|---|
| | HeLa | NCI-H460 | HCT116 | A2780 | A2780cis | A2780adr | MIHA | NCM460 | CCD-19Lu |
| Nanostructure of 1 | 1.9 ± 0.4 | 0.85 ± 0.07 | 0.39 ± 0.03 | 0.51 ± 0.09 | 0.64 ± 0.03 | 1.5 ± 0.4 | 14.5 ± 2.6 | 16.4 ± 2.5 | 15.2 ± 1.9 |
| 2 | 46.4 ± 4.4 | 24.6 ± 4.6 | 8.2 ± 0.2 | 13.4 ± 0.2 | 47.2 ± 8.6 | >120 | 114.6 ± 17.1 | 70.9 ± 6.4 | >100 |
| 5 | 0.52 ± 0.04 | 0.40 ± 0.02 | —[b] | —[b] | —[b] | 1.35 ± 0.10 | 10.3 ± 1.7 | —[b] | —[b] |
| A1 | 0.8 ± 0.1 | 0.1 ± 0.01 | 0.09 ± 0.01 | 0.2 ± 0.02 | 0.2 ± 0.03 | 0.65 ± 0.06 | 0.7 ± 0.1 | 0.13 ± 0.01 | 0.73 ± 0.04 |
| A4 | 0.38 ± 0.07 | 0.15 ± 0.003 | —[b] | —[b] | —[b] | 0.53 ± 0.14 | 0.57 ± 0.04 | —[b] | —[b] |
| A10 | 0.41 ± 0.05 | 0.18 ± 0.004 | —[b] | —[b] | —[b] | 0.52 ± 0.06 | 0.61 ± 0.05 | —[b] | —[b] |
| Au1a | 0.66 ± 0.04 | 0.23 ± 0.01 | 0.09 ± 0.02 | 0.12 ± 0.02 | 0.18 ± 0.01 | 1.1 ± 0.1 | 0.40 ± 0.07 | 0.07 ± 0.01 | 0.23 ± 0.04 |
| NC1 | 0.70 ± 0.15 | 0.41 ± 0.03 | 0.09 ± 0.01 | 0.20 ± 0.02 | 0.47 ± 0.07 | 0.53 ± 0.11 | 3.3 ± 0.5 | 4.5 ± 1.0 | —[b] |
| DOX | 0.57 ± 0.06 | 0.036 ± 0.01 | 0.14 ± 0.02 | 0.045 ± 0.007 | 0.054 ± 0.005 | 0.68 ± 0.05 | 0.10 ± 0.01 | 1.0 ± 0.1 | —[b] |
| Cisplatin | 19.8 ± 1.4 | 65.4 ± 5.0 | 15.7 ± 2.2 | 2.6 ± 0.3 | 8.4 ± 0.05 | 12.7 ± 1.9 | 17.6 ± 1.3 | 12.3 ± 0.9 | 49.1 ± 5.4 |

[a]In vitro cytotoxicity was determined by MTT assay upon incubation of the live cells with the compounds for 72 h.
[b]Not determined.

TABLE 2

Difference in in vitro cytotoxicity toward A2780 cells and the drug-resistant A2780cis and A2780adr cells

| Compounds | Resistance found in A2780cis[a] | Resistance found in A2780adr[b] |
|---|---|---|
| 1 | 0.79 | 0.34 |
| 2 | 0.28 | <0.11 |
| A1 | 1.0 | 0.31 |
| Au1a | 0.67 | 0.11 |
| Cisplatin | 0.31 | 0.20 |

[a]Determined by $IC_{50}$ of A2780cis cells/$IC_{50}$ of A2780 cells.
[b]Determined by $IC_{50}$ of A2780adr cells/$IC_{50}$ of A2780 cells.

TABLE 3

Relative toxicity of 1, 2, A1 and Au1a toward cancer cells and NCM460 cells

| Compounds/ nanostructures | Toxicity toward cancer cells compared to that toward NCM460 cells[a] | | | | | |
|---|---|---|---|---|---|---|
| | HeLa | NCI-H460 | HCT-116 | A2780 | A2780cis | A2780adr |
| Nanostructures of 1 | 8.6 | 19.3 | 42.1 | 32.2 | 25.6 | 10.9 |

TABLE 4

Relative toxicity of 1, 2, A1 and Au1a toward cancer cells and MIHA cells

| Compounds/ nanostructures | Toxicity toward cancer cells compared to that toward MIHA cells[a] | | | | | |
|---|---|---|---|---|---|---|
| | HeLa | NCI-H460 | HCT-116 | A2780 | A2780cis | A2780adr |
| Nanostructures of 1 | 7.6 | 17.1 | 37.2 | 28.4 | 22.7 | 9.1 |
| 2 | 2.5 | 4.7 | 14.0 | 8.6 | 2.4 | <1.0 |
| A1 | 0.9 | 7.0 | 7.7 | 3.5 | 3.5 | 1.1 |
| Au1a | 0.6 | 1.7 | 4.4 | 3.3 | 3.5 | 0.4 |

[a]Determined by $IC_{50}$ of non-tumorigenic MIHA cells/$IC_{50}$ of cancer cells.

To gain more insight onto the higher cytotoxicity of 1 toward cancer cells, time-dependent assays on the induction of apoptosis of HCT116 and NCM460 cells, which are colon cancer cells and colon normal cells respectively, by 1 and Au1a were conducted using CellEvent Caspase-3/7 Green ReadyProbes Reagent. The CellEvent Caspase-3/7 Green ReadyProbes Reagent is non-luminescent in live cells, but shows strong green fluorescence upon cellular activation of caspase-3/7, which is an early indicator of apoptosis. Fluorescence microscopy images of HCT116 cells incubated with CellEvent Caspase-3/7 Green ReadyProbes Reagent and nanostructures of 1 (2 μM) revealed an induction of apoptosis after 15 h and significant apoptotic events after 48 h, while Au1a (2 µM) induced apoptosis of HCT116 cells after 12 h and a large population of apoptotic HCT116 cells was found after incubation with Au1a for 32 h. On the other hand, an induction of apoptosis of NCM460 cells and a large number of apoptotic events were found after incubation with Au1a (2 µM) for 20 and 32 h respectively. Interestingly, 1 (2 µM) did not lead to significant induction of apoptosis of NCM460 cells, as supported by a few number of cells showing green luminescence and the cell morphology as observed in the bright-field images. Flow cytometric analysis of HCT116 cells treated with 1 for 24 and 36 h revealed that 35.83 and 43.83% (corrected by deduction of the percentage of apoptotic cells found in the negative control) of total population of cells were apoptotic, while 1.96 and 10.6% of total population exhibited late apoptotic events. In contrast, 1 was less toxic to NCM460 cells, with 100.9 and 90.14% viability found after incubation for 24 and 36 h respectively. Au1a (2 µM) induced a large number of apoptotic events in both HCT116 and NCM460 cells. Smaller populations of viable NCM460 cells (61.14 and 56.64% [corrected], after incubation for 24 and 36 h, respectively) were found, as compared to those treated with 1 for the same time intervals.

As 1 was found to show faster cellular uptake into HCT116 cells than Au1a (FIGS. 3a and 3c), the induction of apoptosis by 1 after a longer incubation time indicated a time lag for 1 to induce caspase-3/7 activation of HCT116 cells, compared to Au1a. This can be rationalized by the time required for 1 to undergo hydrolytic cleavage of the ester bond before exhibiting its anti-cancer properties. Nonetheless, both 1 and Au1a (2 µM) could induce apoptosis in a large population of HCT116 cells after 48 h, suggesting the readiness of hydrolysis of 1 in HCT116 cells and the effective killing of these colon cancer cells by 1. For normal colon NCM460 cells, Au1a (2 µM) induced their apoptosis after incubation for 20 h, which was slightly longer than that found in HCT116 cells, partly owing to its slower uptake by NCM460 cells (FIGS. 3a and c). The lack of significant activation of caspase-3/7 in NCM460 cells after incubation of 1 for even 72 h can be rationalized by the low cellular uptake (FIGS. 3a and c), in addition to the slow hydrolytic cleavage of the PEG pendant of 1 due to the low metabolic rate of NCM460 cells. As a result, 1 was found to show potent in vitro cytotoxicity toward colon cancer HCT116 cells, with low toxicity toward the colon normal NCM460 cells.

The selective induction of apoptosis of HCT116 cells over NCM460 cells by 1 was further studied using FITC-Annexin V staining. Phosphatidylserine residues, which are located on the cytoplasmic surface of the cell membrane in normal live cells, will be translocated to outer plasma membrane in apoptotic cells. These externalized phosphatidylserine residues can then bind with FITC-Annexin V, giving rise to the green fluorescence from the FITC-Annexin V stain and hence allow the detection of apoptotic events by fluorescence microscopy and flow cytometry. HCT116 cells incubated with 1 and Au1a (2 µM) for 24 h were found to show green fluorescence from FITC-Annexin V, as well as red fluorescence from propidium iodide which is an indicator of necrotic cells. NCM460 cells treated with Au1a were also found to show green and red fluorescence from FITC-Annexin V and propidium iodide respectively, while only a small population of NCM460 cells revealed green fluorescence after incubation of 1 for the same time interval. The quantity of apoptotic cells stained by FITC-Annexin V after treatment with 1 and Au1a was investigated by flow cytometry. Using green fluorescence from HCT116 and NCM460 cells as negative control, the percentage of apoptotic HCT116 cells after incubation of 1 and Au1a for 24 h was found to be 22.5 and 39.6% respectively, while 2.4 and 39.3% of NCM460 cells were found to undergo apoptosis after treatment with 1 and Au1a respectively. Based on the results of fluorescence microscopy and flow cytometry, Au1a was found to be effective on inducing apoptosis of both HCT116 and NCM460 cells. On the other hand, 1 was found to be almost non-toxic toward colon normal NCM460 cells upon incubation for 24 h, but remained active in inducing apoptotic events in colon cancer HCT116 cells. This further suggests the significant reduction of toxic side effect of gold(III) porphyrin complexes toward normal cells by PEG conjugation and formation of nanostructures, demonstrating the potential of 1 as an anti-cancer therapeutic agent with minimal side effects.

Example 6: Gold(III) Porphyrin-PEG Conjugates Shows Selective Induction of Apoptosis in Human Colon Cancer Cells Over Human Colon Non-Tumorigenic Cells in a Co—Culture Cell Model The ability of gold(III) porphyrin-PEG conjugates to selectively induce apoptosis in HCT116 cells over non-tumorigenic NCM460 cells was further investigated by co-culture cell model of HCT116 and NCM460. In order to differentiate the two different cell lines, NCM460 cells were pre-treated by blue-emissive $CMF_2HC$ dye prior to its co-culture with HCT116 cells. The co-culture model was treated with conjugate 1 for 24 h, and flow cytometric analysis revealed two populations (58.5 and 41.5%) based on the detection from the DAPI channel, indicating the success of differentiation of the two different cell lines even after incubation of the cells with 1. On the other hand, the co-culture model treated with 1 for 24 h was stained by FITC-Annexin V and propidium iodide, and imaged by fluorescence microscopy. Green and red fluorescence were primarily observed in cells without showing blue luminescence, i.e. HCT16 cells. The quantity of apoptotic cells of the co-culture model was also determined by flow cytometry; 29.6 and 6.3% of HCT116 and NCM460 cells, respectively, were found to undergo apoptosis upon incubation with 1 (2 µM) for 24 h. The results of both fluorescence microscopy and flow cytometry support the high selectivity of 1 on killing colon cancer cells in the co-culture model of cancer and normal cells.

Staining of the co-culture of HCT116 and NCM460 cells treated with 1 and Au1a (2 µM), respectively, with the Caspase-3/7 Green Reagent showed similar findings as those of the experiments with FITC-Annexin V staining. Fluorescence microscopy images of the co-culture model treated with 1 and stained with Caspase-3/7 Green Reagent revealed strong green fluorescence from HCT116 cells, while only a small population of cells with blue luminescence, i.e. NCM460 cells, displayed green fluorescence. On the other hand, a larger population of NCM460 cells in the co-culture model showed green fluorescence after incubation with Au1a (2 µM) for 24 and 36 h. The population percentages of apoptotic HCT116 and NCM460 cells in the co-culture model after treatment with 1 and Au1a for 24 h were found to be 25.3 and 4.1%, and 54.6 and 29.3% by flow cytometric analysis (corrected based on a negative control experiment) respectively. Together the data indicate the high cytotoxicity of Au1a to both HCT116 and NCM460 cells, while 1 exerts a selective induction of apoptosis in HCT116 cells over NCM460 cells in the co-culture.

To ensure that the results were not due to the effect of $CMF_2HC$ dye on the co-culture, another co-culture of the two cell lines was prepared, with the HCT116 cells pretreated with $CMF_2HC$ dye and hence they would show blue fluorescence upon excitation at 365 nm. This co-culture model treated with 1 for 24 h had 25.04 and 5.01% of HCT116 and NCM460 cells, respectively, undergoing apoptosis as determined by Caspase-3/7 Green Reagent staining and flow cytometric analysis. This confirms the preferential induction of apoptosis by 1 of HCT116 cells over NCM460 cells in the co-culture model, regardless of the effect, if any, of the blue emissive $CMF_2HC$ dye.

Figure 7:
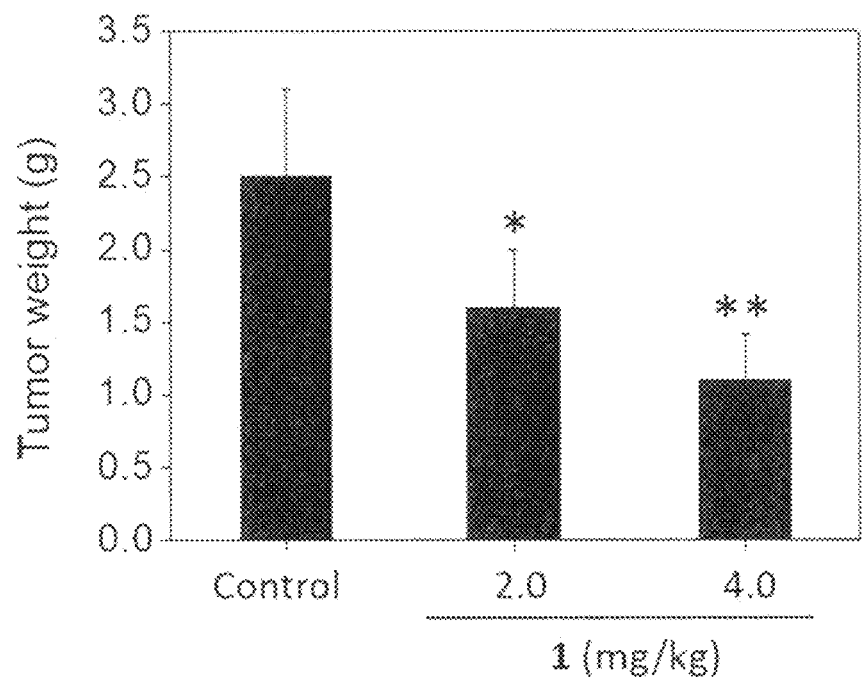
FIG. 7 shows tumor weight of nude mice with A2780 xenografts at 16 days after treatment with 1 or solvent control through intravenous injection. *, p<0.05 compared to solvent control. **, p<0.01 compared to solvent control. All the data are shown as mean±SEM from ten independent experiments.

Example 7: In Vivo Growth Inhibition of Ovarian Tumor Xenografts by Gold(III) Porphyrin-PEG Conjugate Treatment of nude mice bearing A2780 xenografts with 1 for 16 days resulted in a significant reduction of tumor weight, with $p<0.05$ and $<0.01$ for intravenous injections of 2 and 4 mg/kg of 1 respectively (FIG. 7). More importantly, no physiological illness was observed in the mice treated with 1 (4 mg/kg) in 1 week. This suggested the promising in vivo anti-cancer properties of 1 with minimal toxicity.

Figure 8A:
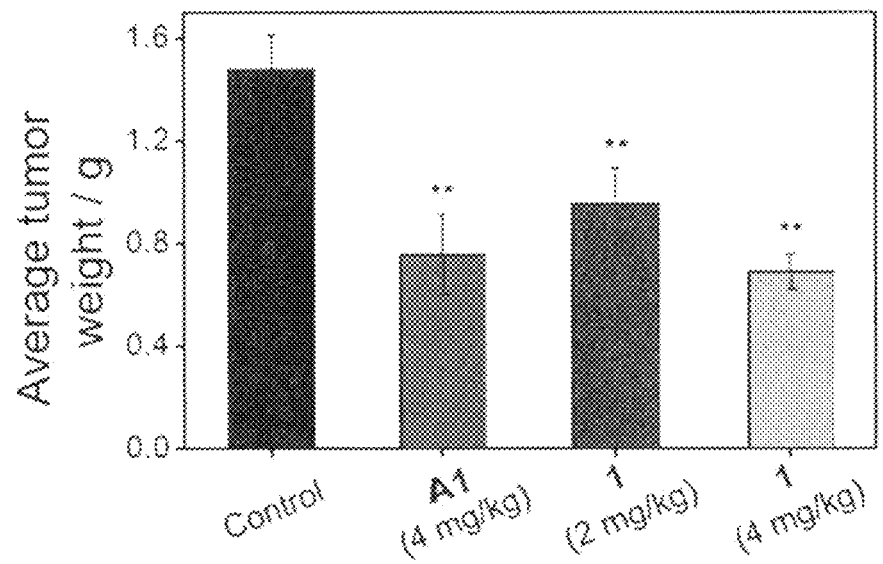
FIG. 8A shows the tumor weight of nude mice with HCT116 xenografts (n=8) treated with different doses of 1 or A1, measured at 24 days post treatment.
Figure 8B:
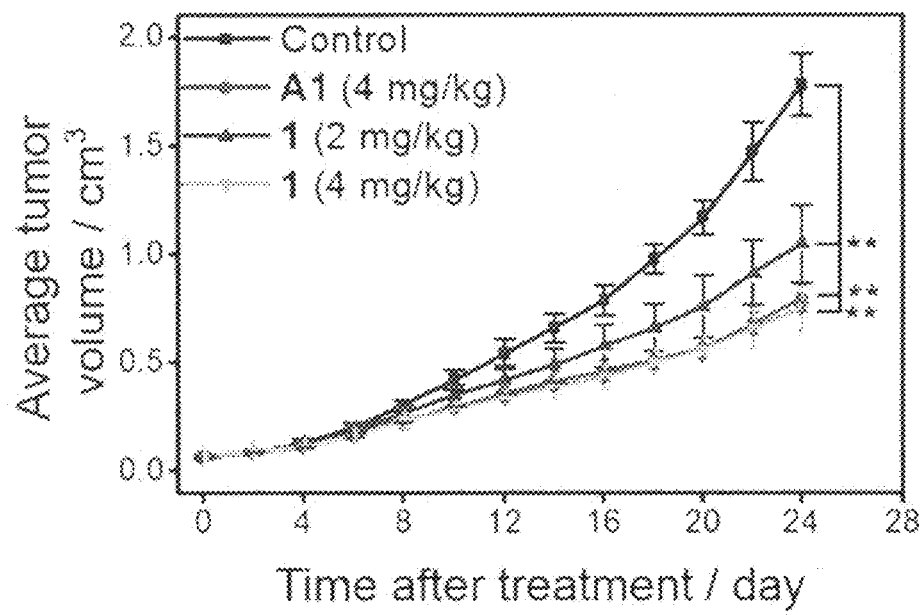
FIGS. 8B and 8C show changes in tumor volume and body weight, respectively, in mice (n=8) after treatment with different doses of 1 or A1. The control group received an equal volume of PBS only. ** denotes p<0.01 vs. control.
Figure 8C:
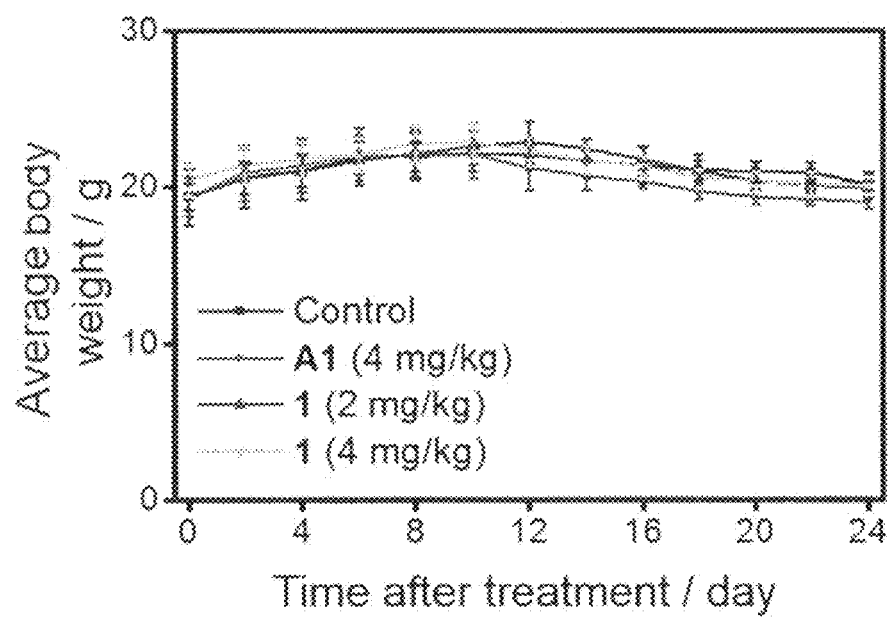
Figure 9A:
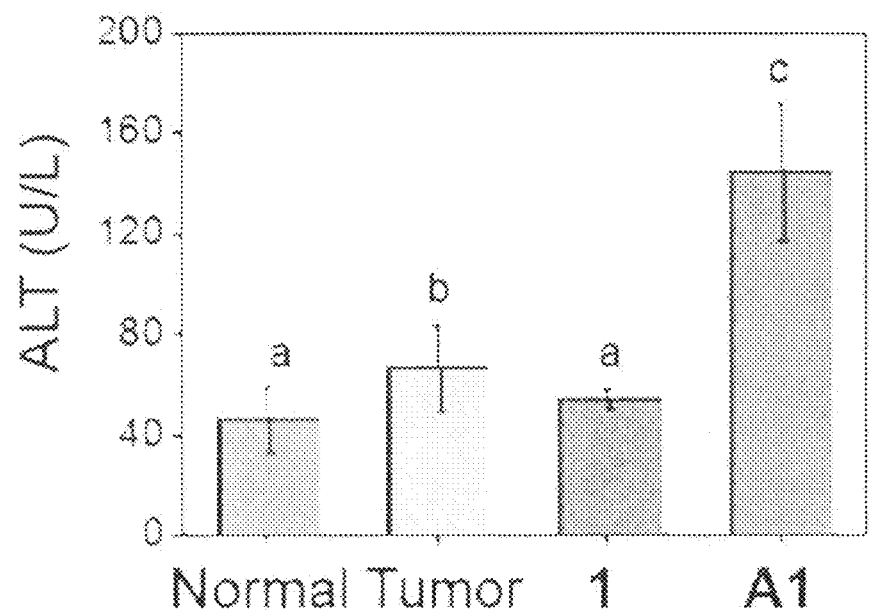
FIGS. 9A-9H show blood biochemistry analysis of ALT, AST, GLB, BUN, CREA, UA, LDH and CK, respectively, in the mice (n=8) at 24 days post-treatment. Bars with different characters were statistically significant at p<0.05 level.
Figure 9B:
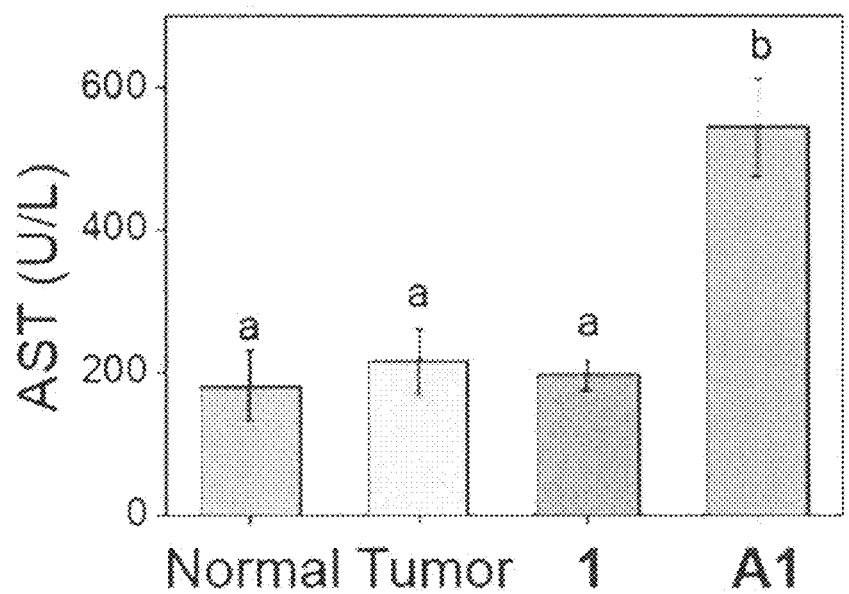
Figure 9C:
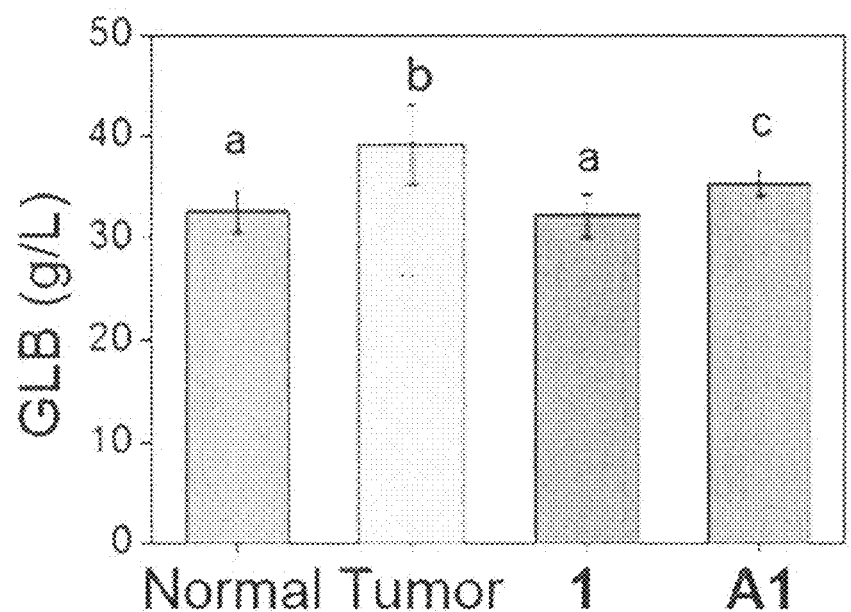
Figure 9D:
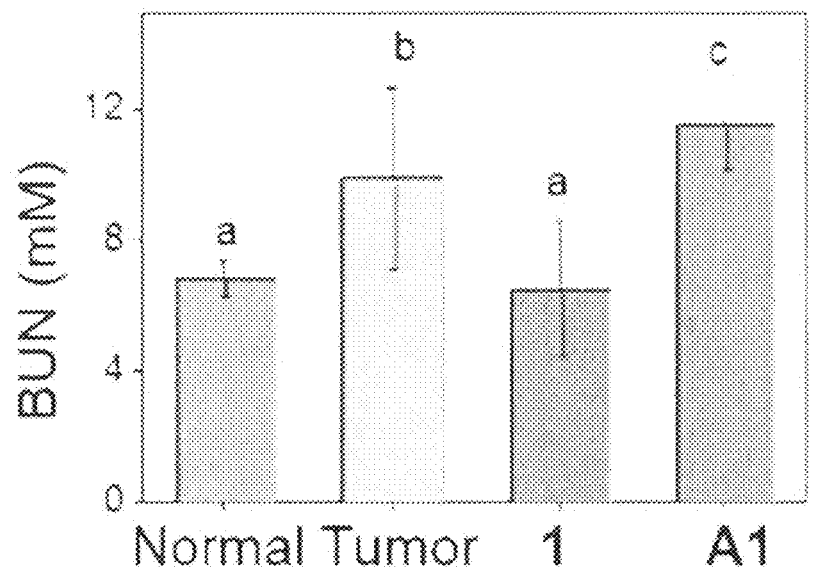
Figure 9E:
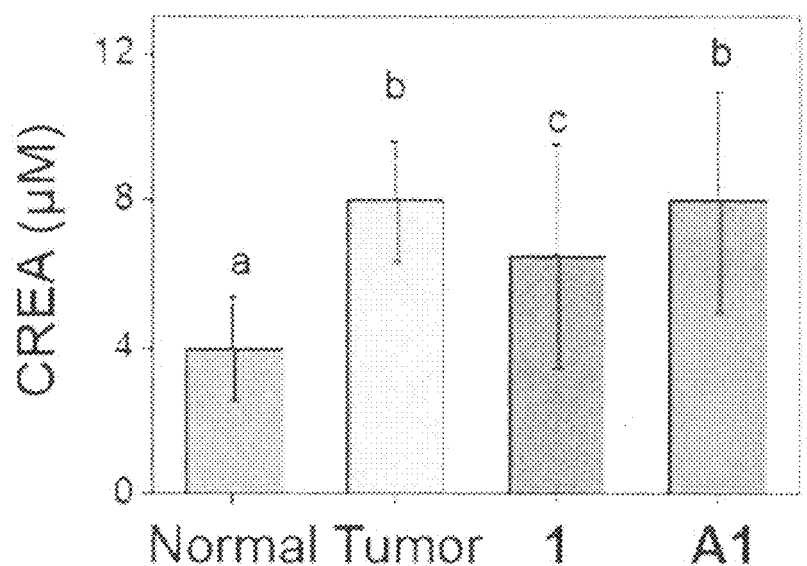
Figure 9F:
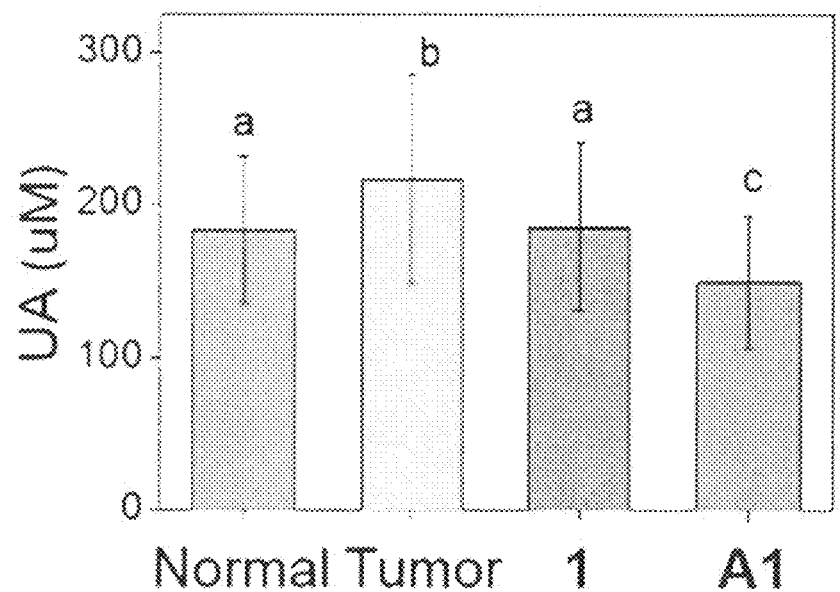
Figure 9G:
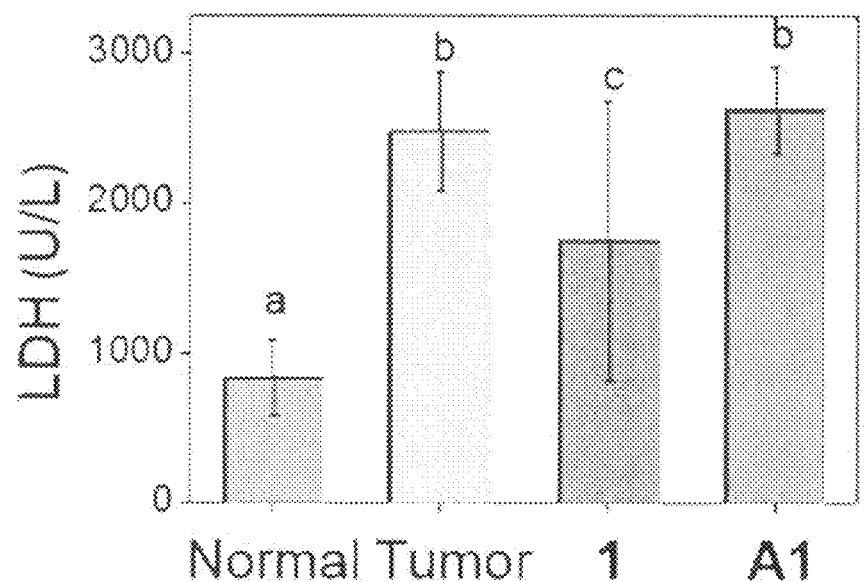
Figure 9H:
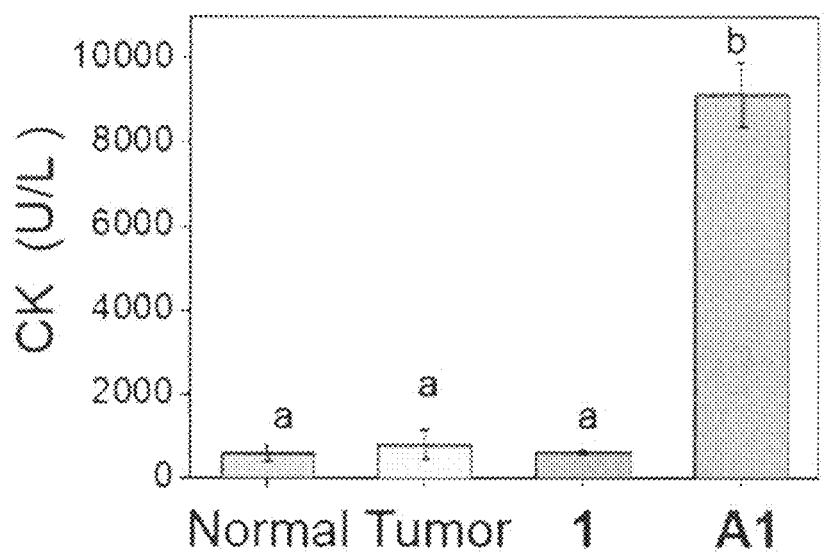

Example 8: In Vivo Growth Inhibition of Colon Tumor Xenografts with Minimal Systemic Toxicity by Gold(III) Porphyrin-PEG Conjugate Treatment of nude mice bearing HCT116 xenografts with 1 (2 or 4 mg/kg) for 24 days through intravenous injection resulted in a significant reduction of tumor weight (35 and 53%, respectively; $p<0.01$, $n=8$; FIG. 8a) and tumor volume (41 and 58% respectively; $p<0.01$, $n=8$; FIG. 8b), with no mouse death or significant loss in body weight (FIG. 8c). Histopathological analysis of the tissues of treated mice revealed that no significant anomaly was observed in lung, liver, kidney, heart and spleen after treatment with 1. The low systemic toxicity of 1 was further supported by the blood biochemistry of nude mice after treatment with 1 (4 mg/kg; FIG. 32a-h); plasma levels of several organ damage indicators including alanine transaminase (ALT), globulin (GLB), blood urea nitrogen (BUN) and creatine kinase (CK) of the treated mice were lower than those of the untreated mice bearing HCT116 xenografts ($p<0.05$; FIG. 32a,c,d,f), and fell within the statistically relevant range of those of mice without the xenograft. In addition, $[Au(TPP—COOH)]^+$ was found in the UPLC-QTOF-MS of tumor tissues of mice treated by 1, supporting the propensity for hydrolysis of 1 in vivo.

Figure 10:
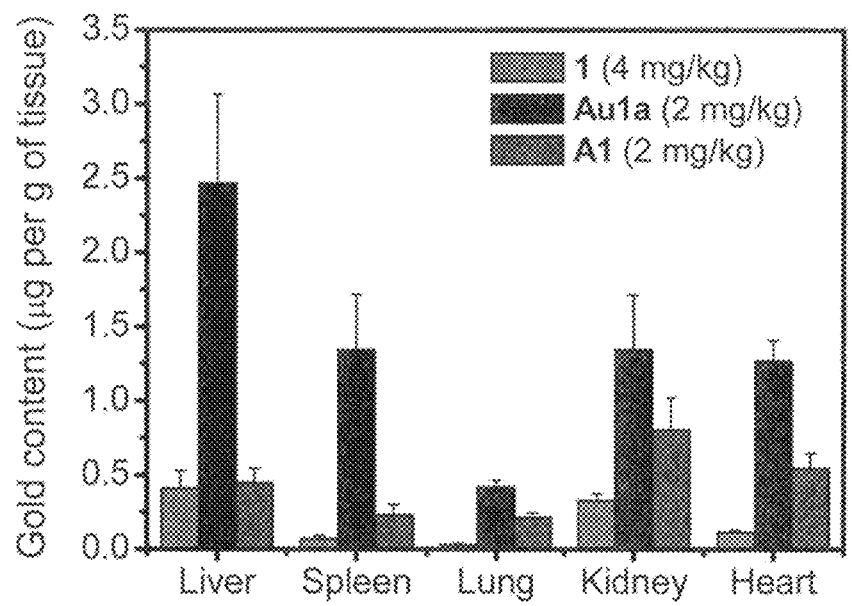
FIG. 10 shows the biodistribution of gold complexes in nude mice bearing HCT116 xenografts after 14 days of treatment with 1 (4 mg/kg), Au1a and A1 (2 mg/kg), respectively, through intravenous injection. In each grouping of bars, the bars are in the same left-to-right order: 1, Au1a, A1. The gold content in homogenized tissues was quantified by ICP-MS. n=5 (for Au1a and A1) and 6 (for 1). Data are shown as mean±SD.

On the other hand, intravenous injection of A1 (4 mg/kg) to nude mice bearing HCT116 xenografts resulted in significant reduction of tumor weight and tumor volume (49 and 56% respectively; $p<0.01$, $n=8$; FIG. 8a,b). Yet, higher concentration of A1 was required to achieve similar inhibition of tumor growth as found in the treatment with 1 (4.43 mmol/kg vs 0.68 mmol/kg), suggesting the more potent anti-tumor effect of 1. Immunohistochemical analyses of tumor sections further supported the superior anti-tumor activities of 1 over that of A1. Effective elimination of nuclear atypia and mitosis were observed after treatment of the mice with 1 (4 mg/kg), but not for the treatment with A1 (4 mg/kg). This, together with the more significant inhibition of the expression of Ki67 and VEGFR2, enhanced expression of p53 and elevated DNA fragmentation (from TUNEL staining) by 1, demonstrates that 1 can effectively decrease cancer cell proliferation and induce cancer cell apoptosis in vivo. More importantly, in contrast to the low systemic toxicity of 1, histopathological analysis showed damage in normal lung, liver and kidney tissues after treatment with A1 (4 mg/kg). Significant pulmonary hemorrhage in the alveoli and a thickening of alveolar walls were found. Also, apoptotic hepatocytes and swollen renal epithelial cells were found, leading to subsequent shrinkage of kidney tubules. The blood biochemistry of mice treated with A1 indicated significant damage in the lung, liver and kidney of the mice (FIG. 32a-h). The lower systemic toxicity of 1 can be explained by the lower accumulation of 1 in the organs of mice treated at its effective dosage, as compared to that of A1 and Au1a (FIG. 10).

Figure 11:
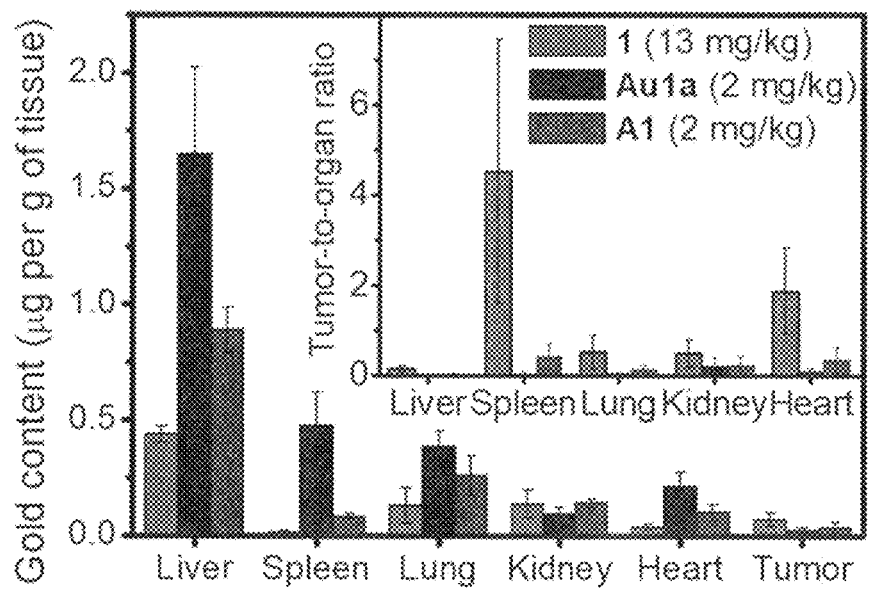
FIG. 11 shows the biodistribution of gold compounds in different organs of nude mice bearing HCT-116 xenografts after single-dose intravenous injection with 1 (13 mg/kg; n=5), Au1a (2 mg/kg; n=4) and A1 (2 mg/kg, n=4) at 24 h post-treatment. The gold contents in homogenized tissues were quantified by ICP-MS. Solvent control was used as background for calculation. Inset shows the ratios of gold content in tumor to that in other organs.

In vivo biodistribution study of HCT116 xenografted nude mice subjected to single-dose intravenous injections of equal molar amount of gold compounds at 24 h post-treatment revealed higher accumulation of 1 (determined by ICP-MS analysis) in tumor compared to mice treated with Au1a (by 3.3-fold) or A1 (by 2.0-fold) (FIG. 11). As lower gold contents were found in liver, spleen, lung, kidney and heart of 1-treated mice, 1 showed significantly higher tumor-to-organ ratio than Au1a or 3 (FIG. 11b). This can be attributable to the nanostructures of 1, which may lead to in vivo tumor accumulation by the EPR effect.

Figure 12A:
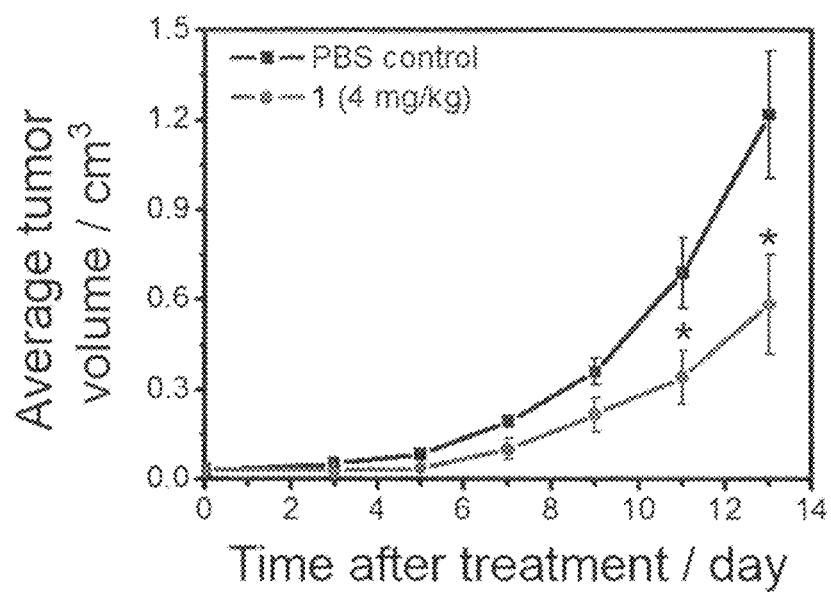
FIG. 12A shows the tumor volume of nude mice with A2780cis xenografts (n=5) treated with 1 (4 mg/kg) or solvent control over time.
Figure 12B:
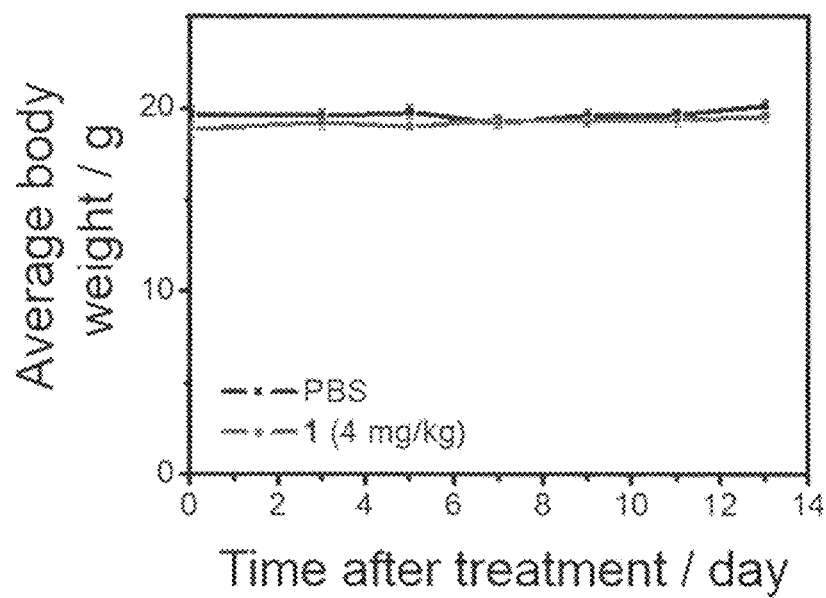
FIG. 12B show changes in body weight of nude mice with A2780cis xenografts (n=5) treated with 1 (4 mg/kg) or solvent control over time. The control group received an equal volume of PBS only. * denotes p<0.05 vs. control.

Example 9: In Vivo Growth Inhibition of Cisplatin-Resistant Ovarian Tumor Xenografts by Gold(III) Porphyrin-PEG Conjugate To further investigate the ability of 1 to treat drug-resistant tumors that should be of great interest in clinical application, in vivo antitumor experiments on nude mice bearing cisplatin-resistant A2780cis xenografts with 1 were conducted. Over 52% reduction ($p<0.05$) of tumor volume was found after treatment of mice with 1 (4 mg/kg, intravenous injections for every 2-3 days for 13 days; $n=5$; FIG. 12a), with no mouse death or significant loss in body weight (FIG. 12b). This suggests that 1 can be useful for development of anticancer agents for treating drug-resistant tumors.

Example 10: Encapsulation of Doxorubicin by Nanostructures of Gold(III) Porphyrin-PEG Conjugates to Form Nanocomposites Co-delivery of therapeutics would be advantageous for anti-cancer treatment, due to the possibility of achieving strong synergistic effect on killing cancer cells and to prevent or minimize the development of drug-resistance, thus improving efficacy of the treatment with reduction of undesired side effects. In view of the interesting nanostructures formed by 1, its ability to overcome efflux pump-mediated drug resistance of A2780adr cells as suggested by the cellular uptake experiments (FIG. 3b) and the relatively low toxicity of the nanostructures toward normal cells than that toward cancer cells, these have prompted us the nanostructures of 1 were used for the encapsulation of other therapeutics for co-delivery. Doxorubicin (DOX), which has been clinically approved for the treatment of ovarian cancer and multiple myeloma, shows severe cardiotoxicity when it is administrated alone. Also, resistance of doxorubicin owing to P-glycoproteins, which were examples of efflux pumps, was developed in some cancer cell lines, such as A2780adr. Therefore, doxorubicin was encapsulated in the nanostructures of 1 and tested for activity against cancer cells.

Encapsulation of DOX by nanostructures of 1 was carried out by nanoprecipitation of acetonitrile solution of 1 (2.5 mg) and DOX (0.18 mg) into PBS solution. Nanostructures of ca. 120 nm were observed in the TEM image of nanocomposites of 1 and DOX (NC1). Profiles of DLS experiments and zeta potential measurements indicated that the nanostructures of NC1 have hydrodynamic radii of 122.1±13.4 nm and zeta potential of −2.5±1.6 mV respectively, similar to those of the nanostructures of 1. The gold content in NC1 was confirmed by EDX. Due to the significant overlapping of the UV-vis absorption spectra of 1 and DOX which hindered the quantification of 1 and DOX in the nanocomposites by their UV-vis absorption properties, the concentration of 1 in NC1 was determined by ICP-MS experiments. On the other hand, DOX concentration in NC1 was measured by UPLC coupled with photodiode array for detection using daunorubicin hydrochloride as an internal standard. From the results of the two experiments, the mole ratio of 1 to DOX in NC1 as well as the encapsulation efficiency of DOX by 1 were found to be 7:1 and 16.5% respectively (Table 5).

TABLE 5

Physiochemical properties of nanocomposites of 1 and DOX

| | Feed ratio ([1]:[DOX]) | Found mole ratio of 1[a] to DOX[b] | Hydrodynamic diameter/nm | Zeta potential/ mV | Encapsulation efficiency, % |
|---|---|---|---|---|---|
| NC1 | 1.41 | 7:1 | 122.1 ± 13.4 | −2.5 ± 1.6 | 16.5 |
| NC2 | 0.56 | 2.2:1 | 139.6 ± 20.9 | −0.8 ± 4.2 | 11.2 |
| NC3 | 0.30 | 1.3:1 | 133.5 ± 19.2 | −1.2 ± 4.2 | 9.4 |

[a]The concentration of 1 in the nanocomposites was determined by ICP-MS.
[b]The concentration of DOX in the nanocomposites was determined by UPLC coupled with photodiode array detector using daunorubicin hydrochloride (3.6 μM) as the internal standard.

Nanocomposites with different feed ratios of 1 and DOX have also been prepared by using the same amount of 1 but different concentrations of DOX. An increase in feed ratio of DOX to 1 was found to increase the loading of DOX into the nanocomposites (Table 5), as supported by the UPLC experiments. However, a decrease in encapsulation efficiency was also found with increasing feed ratio of DOX to 1 (Table 5). For nanocomposites with different DOX loadings, they were found to show similar size and surface charge to each other, as reflected by the DLS and zeta potential measurements (Table 5).

Figure 13A:
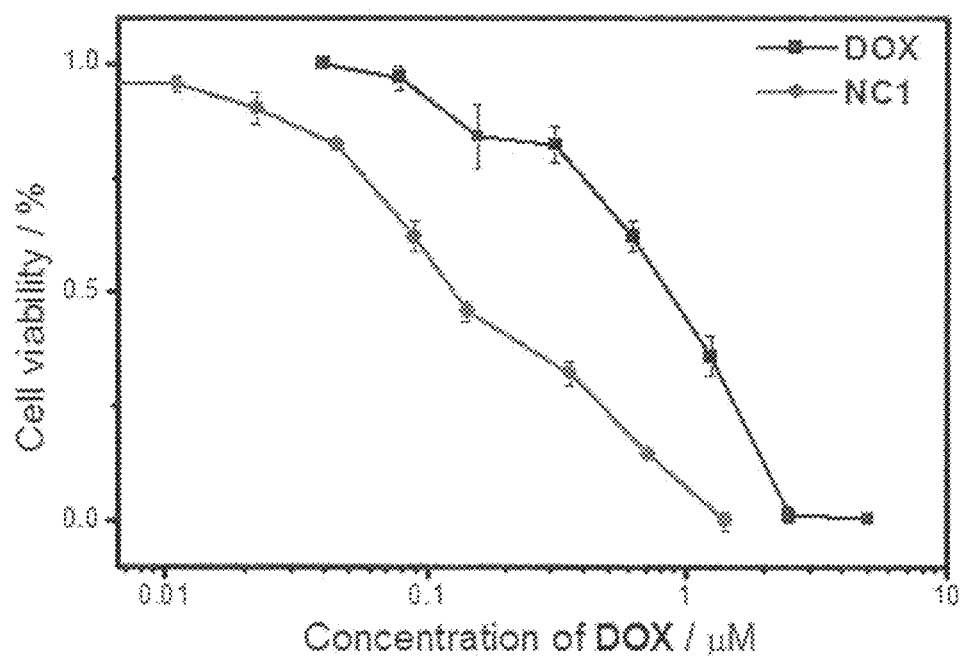
FIGS. 13A and 13B shows the cell viability profiles of (11A) HeLa and (11B) A2780adr cells upon treatment with different concentrations of NC1 and DOX for 72 h. NC1 was composed of 1 and DOX ([1]: [DOX]=7:1) which were both anti-cancer active.
Figure 13B:
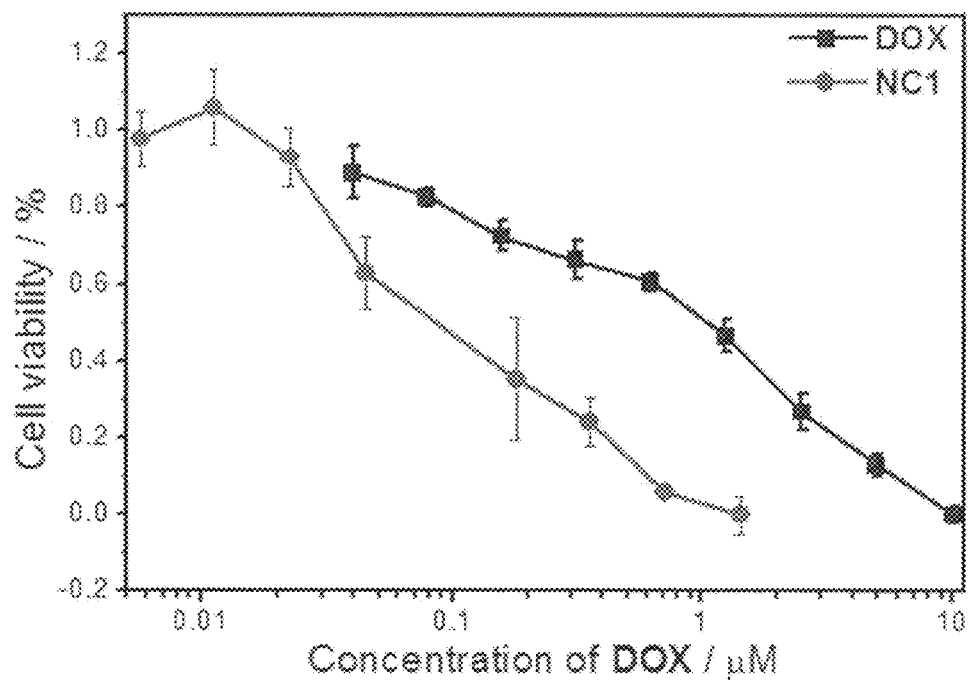
Figure 14A:
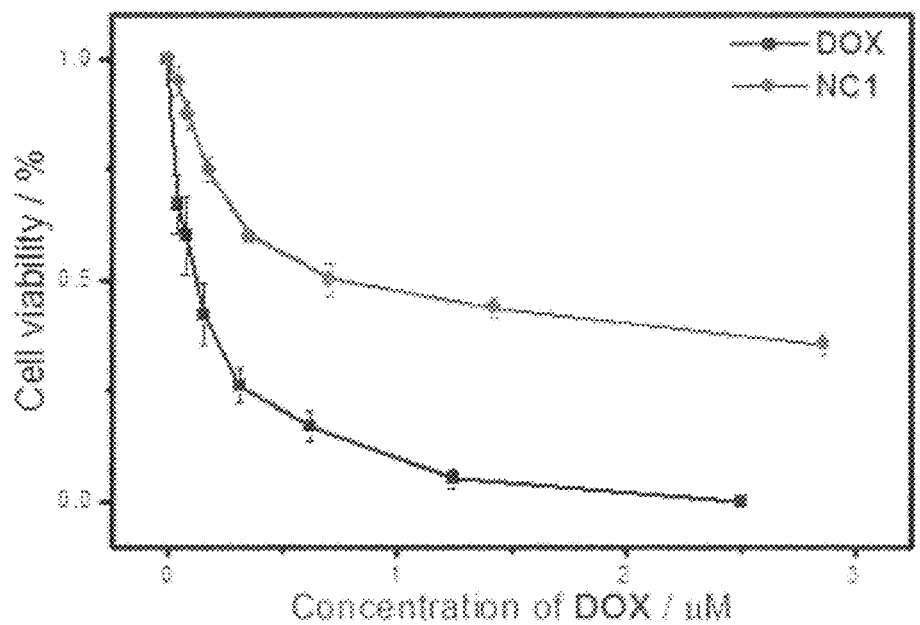
FIG. 14A shows the profile of cell viability of MIHA cells upon treatment with different concentrations of NC1 ([1]: [DOX]=7:1) and DOX for 72 h.
Figure 14B:
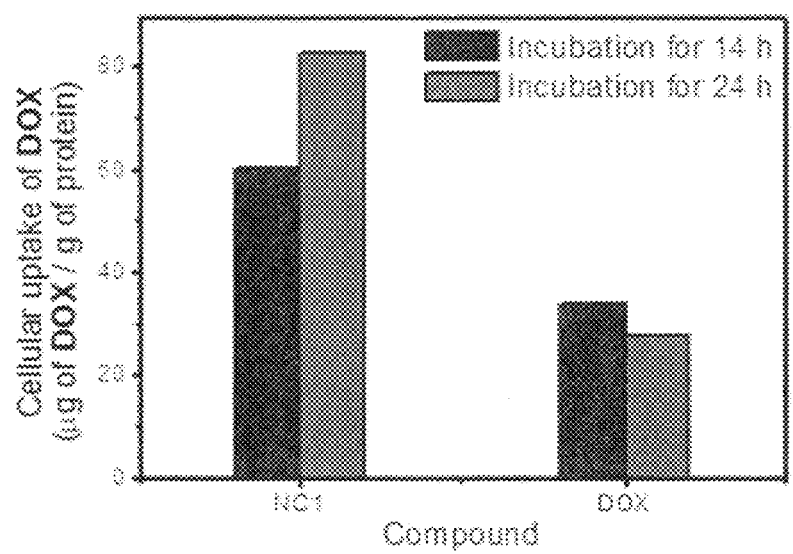
FIG. 14B show the cellular uptake of NC1 ([1]=3.5 μM and [DOX]=0.5 μM) and DOX (0.5 μM) into A2780adr cells, respectively, after incubation at 37° C. for indicated time intervals. In each grouping of bars, the bars are in the same left-to-right order: 14 h, 24 h.

Example 11: Synergistic Effect on Killing Human Cancer Cells by the Nanocomposites of Gold(III) Porphyrin-PEG Conjugates and Doxorubicin DOX was found to be very effective in killing cancer and non-tumorigenic cells based on in vitro MTT assays (Table 1). Therefore, it was anticipated that a not too high loading of DOX into nanostructures of 1 could be used for anticancer purposes in order to maintain low toxicity toward non-tumorigenic cells. Together with the higher encapsulation efficiency of DOX, NC1 was selected for investigations of the in vitro cytotoxicity. NC1 was found to be more potent in killing cancer cells than either nanostructures of 1 alone or DOX alone (Table 1; FIGS. 13A and 13B). For example, as revealed by the green luminescence from CellEvent Caspase-3/7 Green ReadyProbes Reagent, NC1 ([1]=3.5 μM and [DOX]=0.5 μM) could induce apoptosis of HCT116 cells after incubation for 18 h, while 30 h incubation was required for significant induction of apoptosis of HCT116 cells by DOX alone (FIGS. 14A and 14B). Interestingly, NC1 showed lower toxicity toward non-tumorigenic MIHA and NCM460 cells than the administration of DOX alone (Table 1; FIG. 13A). The in vitro cytotoxicity of NC1 was also compared to that of the mixture of nanostructures of 1 and DOX. It was found that the mixture of nanostructures of 1 and DOX displayed higher cytotoxicity toward HeLa cells than any single component, but was found to be relatively less effective compared to NC1 (Table 6). The observed cytotoxicity was further evaluated by the combination index (CI), which can describe the effect of drug combination. The median-effect equation derived from the mass-action law principle at equilibrium-steady state via mathematical induction and deduction for different reaction sequences and mechanisms and different types of inhibition has been shown to be the unified theory for the Michaelis-Menten equation, Hill equation, Henderson-Hasselbalch equation, and Scatchard equation. It is shown that dose and effect are interchangeable via defined parameters. This general equation for the single drug effect has been extended to the multiple drug effect equation for n drugs. These equations provide the theoretical basis for the combination index (CI)-isobologram equation that allows quantitative determination of drug interactions, where CI<1, =1, and >1 indicate synergism, additive effect, and antagonism, respectively. [Chou, et al. *Pharmacol. Rev.* 2006, 58, 621] Based on the calculated CI value at $IC_{50}$ of the drug combinations by CompuSyn, both NC1 and the mixture of nanostructures of 1 and DOX showed synergism on killing HeLa cells, with the former one being more potent. The synergistic effect can originate from different molecular targets and/or mechanism of action of DOX from that of gold(III) porphyrin complexes. DNA should be the primary target of DOX, while gold(III) porphyrin complexes were found to cause depletion of mitochondrial potential and induction of apoptosis by both the caspase-dependent and caspase-independent mitochondrial death pathways. These different modes of action would allow supra-additive effect on killing HeLa cells by the co-delivery. For the observation of stronger synergism in NC1 than the mixture of 1 and DOX, this can be attributed to the synchronized delivery of the two chemotherapeutics to HeLa cells from NC1.

TABLE 6

In vitro cytotoxicity of drug combinations of 1 and DOX upon incubation of HeLa, A2780adr and MIHA cells, respectively, for 72 h

| Cell lines | Compounds/drug combinations | 1 at $IC_{50}$/ μM | DOX at $IC_{50}$/ μM | Total dose at $IC_{50}$/ μM | Combination Index (CI) |
|---|---|---|---|---|---|
| HeLa | Nanostructures of 1 | 1.9 | — | 1.9 | — |
| | DOX alone | — | 0.57 | 0.57 | — |
| | Co-incubation of nanostructures of 1 | 0.74 | 0.11 | 0.85 | 0.57 |

TABLE 6-continued

In vitro cytotoxicity of drug combinations of 1 and DOX upon incubation of HeLa, A2780adr and MIHA cells, respectively, for 72 h

| Cell lines | Compounds/drug combinations | 1 at $IC_{50}$/ μM | DOX at $IC_{50}$/ μM | Total dose at $IC_{50}$/ μM | Combination Index (CI) |
|---|---|---|---|---|---|
| | with DOX ([1]:[DOX] = 7:1) | | | | |
| | NC | 0.62 | 0.09 | 0.71 | 0.48 |
| A2780adr | Nanostructures of 1 | 1.5 | — | 1.5 | — |
| | DOX alone | — | 0.7 | 0.7 | — |
| | Co-incubation of Nanostructures of 1 with DOX ([1]:[DOX] = 7:1) | 0.85 | 0.12 | 0.97 | 0.75 |
| | NC1 | 0.53 | 0.08 | 0.61 | 0.47 |
| MIHA | Nanostructures of 1 | 14.4 | — | 14.4 | — |
| | DOX alone | — | 0.1 | 0.1 | — |
| | Co-incubation of nanostructures of 1 with DOX ([1]:[DOX] = 7:1) | 0.57 | 0.08 | 0.65 | 0.86 |
| | NC1 | 3.3 | 0.5 | 3.8 | 4.9 |

Example 12: Overcoming Efflux Pump-Mediated Drug Resistance of A2780adr Cells by the Nanocomposites of Gold(III) Porphyrin-PEG Conjugates and Doxorubicin Due to the efflux pump in A2780adr cells, DOX showed 15-fold lower cytotoxicity toward A2780adr cells than the non-resistant A2780 cells (Table 1). In view of the accumulation of nanostructures of 1 in A2780adr cells over time which suggests the possibility to overcome the efflux pump-mediated drug-resistance (FIG. 3B), cellular uptake experiments of DOX by A2780adr cells from the administration of NC1 and DOX alone have been carried out. The uptakes of DOX in the form of NC1 by A2780adr cells were found to be 60.2 and 82.7 μg per g of proteins after incubation for 14 and 24 h respectively, based on the analysis of cell lysates using UPLC-QTOF-MS (FIG. 14B). On the other hand, 33.9 and 27.8 μg of DOX per g of proteins were found in the cell lysates of A2780adr cells after incubation with DOX for 14 and 24 h respectively, and these values were 1.8- and 3.0-fold smaller than those found after incubation of NC1 for the same time intervals (FIG. 14B). This indicates that a significant increase in DOX content in A2780adr cells can be achieved by the administration of NC1, demonstrating the ability of NC1 to function as a nanocarrier of DOX for overcoming drug-resistance.

The in vitro cytotoxicity of NC1 and mixtures of nanostructures of 1 and DOX was also investigated by MTT assay (Table 6; FIGS. 13A and 13B). From the calculated CI values at $IC_{50}$ of the drug combinations, co-incubation of A2780adr cells with 1 and DOX (CI=0.75) resulted in moderate synergism, while NC1 showed synergism with significant reduction of effective dosage for killing A2780adr cells (CI=0.47). The much higher potency found in NC1 than mixtures of 1 and DOX should not only be attributed to the synchronized delivery of the two chemotherapeutics as observed in the study of HeLa cells (Table 6). In view of the overcoming of efflux pump-mediated drug-resistance by the nanostructures of NC1 (FIG. 3B), the higher accumulation of DOX in A2780adr cells from the incubation with NC1 (FIG. 14A) would favor killing of A2780adr cells Together with the synergistic effect brought by the drug combination, superior anti-cancer properties toward drug-resistant cancer cells can be achieved by the encapsulation of DOX using the nanostructures of 1.

Example 13: Nanocomposites of Gold(III) Porphyrin-PEG Conjugates and Doxorubicin Shows Significant Reduction of Toxicity Toward Non-Tumorigenic MIHA Cells It is noteworthy that the $IC_{50}$ of DOX in NC1 toward non-tumorigenic MIHA cells was significantly higher than the $IC_{50}$ found from the administration of DOX alone (FIG. 14A; Table 1 and 6), even in the presence of nanostructures of 1 (1 is quite non-toxic toward MIHA cells with $IC_{50}$ of 14.5 μM). This suggests the lowering of toxicity of DOX toward non-tumorigenic cells by encapsulation using the nanostructures of 1. Together with the improvement in efficacy against cancer cells as described above (Table 1 and 6; FIGS. 13A and 13B), NC1 showed excellent selectivity on killing cancer cells over non-tumorigenic cells, compared to the administration of DOX alone (Table 7). Similar improvement in selectivity of killing some cancer cells over non-tumorigenic NCM460 cells was also observed in the study of NC1 compared to that of DOX alone (Table 8). On the other hand, the mixture of 1 and DOX displayed much higher toxicity toward MIHA cells, compared to NC1 (Table 6). Slight synergism on killing MIHA cells was found in the mixture of 1 and DOX (0.86), while NC1 showed "strong antagonism" for killing MIHA cells (CI=4.9) which was totally different from the studies of NC1 with HeLa and A2780adr cells.

TABLE 7

Relative toxicity of DOX toward cancer cells and MIHA cells
through administration of DOX alone and administration by NC1

| Compounds/ nanostructures | Toxicity toward cancer cells compared to that toward MIHA cells[a] | | | | | |
|---|---|---|---|---|---|---|
| | HeLa | NCI-H460 | HCT-116 | A2780 | A2780cis | A2780adr |
| DOX in NC1 | 7.6 | 17.1 | 37.2 | 28.4 | 22.7 | 9.1 |
| DOX alone | 0.2 | 2.8 | 0.7 | 2.2 | 1.9 | 0.1 |

[a]Determined by $IC_{50}$ of non-tumorigenic MIHA cells/$IC_{50}$ of cancer cells. The cytotoxicity of complex 1 in NC1 has not been taken into considerations.

TABLE 8

Relative toxicity of DOX toward cancer cells and NCM460 cells
through administration of DOX alone and administration by NC1

| Compounds/ nanostructures | Toxicity toward cancer cells compared to that toward NCM460 cells[a] | | | | | |
|---|---|---|---|---|---|---|
| | HeLa | NCI-H460 | HCT-116 | A2780 | A2780cis | A2780adr |
| DOX in NC1 | 6.4 | 11.0 | 50.0 | 22.5 | 9.6 | 8.5 |
| DOX alone | 1.8 | 27.8 | 7.1 | 22.2 | 18.5 | 1.5 |

[a]Determined by $IC_{50}$ of non-tumorigenic NCM460 cells/$IC_{50}$ of cancer cells. The cytotoxicity of complex 1 in NC1 has not been taken into considerations.

Figure 4:
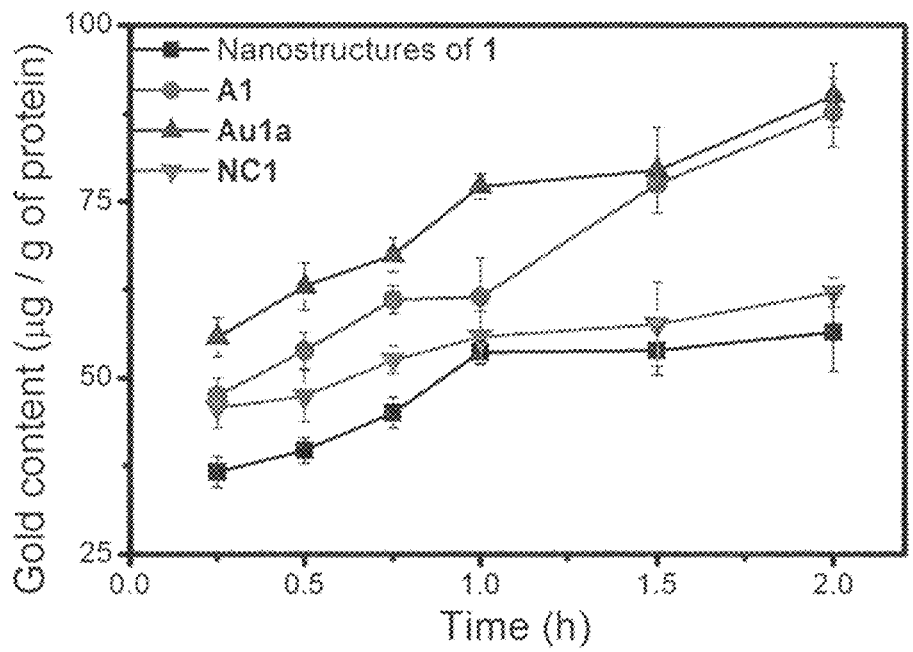
FIG. 4 shows the cellular uptake of the complexes by MIHA cells after incubation at 37° C. for indicated time intervals.

To rationalize the lower toxicity of NC1 toward MIHA cells, cellular uptake of NC1 by MIHA and cancer cells has been investigated by ICP-MS (FIGS. 3b and 4). The gold contents in A2780 and A2780adr cells were 2.6- and 2.0-fold higher than that in MIHA cells, respectively, after incubation with NC1 for 2 h. This suggests lower cellular uptake of NC1 into MIHA cells, and hence a lower DOX concentration in MIHA cells is anticipated compared to that in A2780 and A2780adr cells. On the other hand, co-incubation of MIHA cells with 1 and DOX should not lead to significant changes in cellular uptake rate of DOX. As a result, the mixture of 1 and DOX revealed slight synergism on killing MIHA cells due to different molecular targets and/or mechanism of action of DOX from that of 1, similar to the study of HeLa and A2780adr cells (Table 6). For NC1, it was less toxic toward MIHA cells as reflected by the apparent "strong antagonism" (Table 3), which should be owing to the decrease of DOX cellular uptake by the encapsulation from the nanostructures of 1, rather than real antagonism from DOX and 1.

Figure 15:
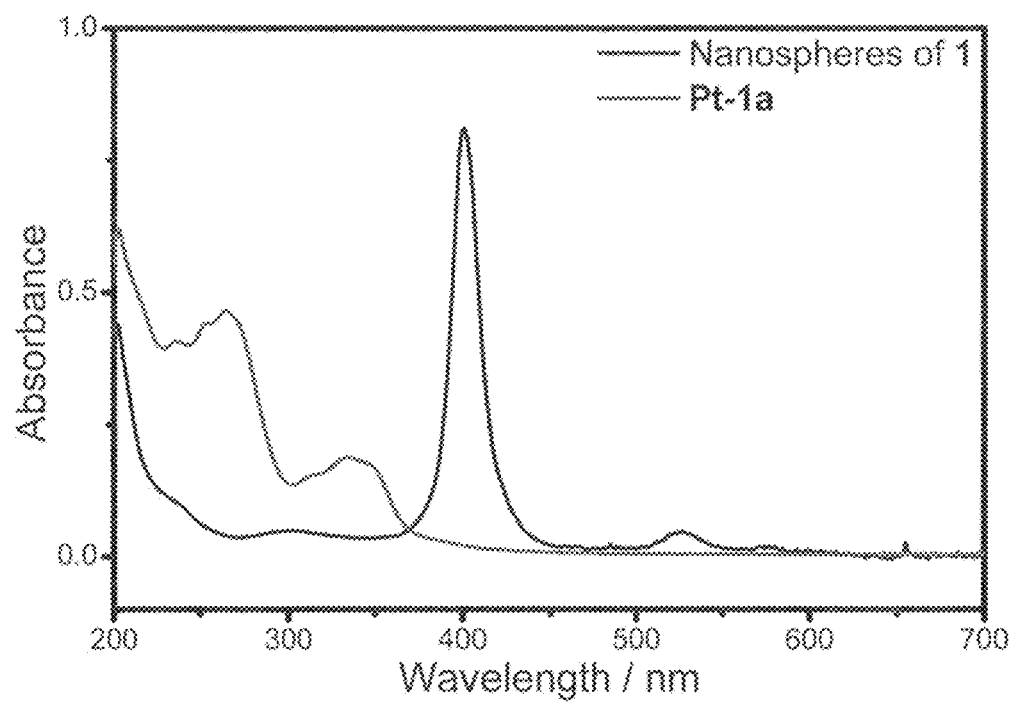
FIG. 15 shows the UV-vis absorption spectra of 1 (3.65 μM) in PBS solution and Pt-1a (13 μM) in PBS-DMSO solution mixture (99:1, v/v). 1 shows a peak at 400 nm while Pt-1a does not.

Example 14: Encapsulation of Platinum(II) NHC Complex by Nanostructures of Gold(III) Porphyrin-PEG Conjugates to Form Nanocomposites Encapsulation of anti-cancer metal complexes by nanostructures of gold(III) porphyrin-PEG conjugates was carried out. Pt-1a and nanostructures of 1 was found to show synergistic effect on killing HeLa cells, as supported by the CI values found in the co-incubation experiments (Table 9). Therefore, nanocomposites of 1 and Pt-1a were prepared. As Pt-1a shows strong UV-vis absorption at 270 nm while negligible absorption in this region was observed in the PBS solution of 1 (FIG. 15), the encapsulation efficiency of Pt-1a by 1 and the mole ratio of Pt-1a to 1 in the nanocomposites were determined by the UV-vis absorption experiments, and were found to be 11.7% and 1:9 respectively.

TABLE 9

In vitro cytotoxicity and Combination Index (CI) of
drug combinations of 1 and Pt-1a upon incubation of
HeLa cells for 72 h

| Drug combinations | Dose of complex 1 at $IC_{50}/\mu M$ | Dose of complex Pt-1a at $IC_{50}/\mu M$ | Total dose at $IC_{50}/\mu M$ | Combination Index (CI) |
|---|---|---|---|---|
| 1 alone | 1.32 | — | 1.32 | — |
| Pt-1a alone | — | 0.88 | 0.88 | — |
| 1:Pt-1a (1:1) | 0.32 | 0.32 | 0.64 | 0.60 |
| 1:Pt-1a (3:1) | 0.37 | 0.12 | 0.49 | 0.42 |
| 1:Pt-1a (4:1) | 0.50 | 0.13 | 0.63 | 0.52 |
| 1:Pt-1a (9:1) | 0.50 | 0.06 | 0.56 | 0.44 |

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about." The symbol "~" means about.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a conjugate" includes a plurality of such conjugates, reference to "the conjugate" is a reference to one or more conjugates and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different substituent groups does not indicate that the listed substituent groups are obvious one to the other, nor is it an admission of equivalence or obviousness.

Every compound, conjugate, complex, and composition disclosed herein is intended to be and should be considered to be specifically disclosed herein. Further, every subgroup that can be identified within this disclosure (including individual compounds, conjugates, complexes, and compositions) is intended to be and should be considered to be specifically disclosed herein. As a result, it is specifically contemplated that any compound, conjugate, complex, and composition, or subgroup of compounds, conjugates, complexes, and compositions can be either specifically included for or excluded from use or included in or excluded from a list of compounds, conjugates, complexes, and compositions. For example, as one option, groups of complexes are contemplated where each complex is as described herein but is not complex A3, A6 or A7. As another example, groups of conjugates are contemplated where each complex is as described herein but is not conjugate 3, 6 or 7. As another example, groups of complexes and compositions are contemplated where each complex and composition is as described herein and is able to induce apoptosis in cancer cells in the subject. As another example, groups of conjugates are contemplated where each conjugate is as described herein and is able to encapsulate one or more anti-cancer chemotherapeutic agents (thus forming nanocomposites for co-delivery). Complex Au1a, complex A1, complex A2, complex A3, complex A4, complex A5, complex A6, complex A7, complex A8, complex A9, complex A10, complex A11, conjugate 1, conjugate 2, conjugate 3, conjugate 4, conjugate 5, and conjugate 6 can be independently and specifically included or excluded from the compounds, conjugates, and compositions and methods disclosed herein. For example, complex Au1a, complex A1, and complex A2 can be specifically included or excluded from the compounds, conjugates, and compositions and methods disclosed herein. As another example, conjugate 1 and conjugate 2 can be specifically included or excluded from the compounds, conjugates, and compositions and methods disclosed herein. As another example, Complex Au1a, complex A1, complex A2, conjugate 1, and conjugate 2 can be specifically included or excluded from the compounds, conjugates, and compositions and methods disclosed herein.

Those skilled in the art will recognize, or be able to ascertain using no more than routine experimentation, many equivalents to the specific embodiments of the method and compositions described herein. Such equivalents are intended to be encompassed by the following claims.

We claim:

1. A composition for inducing cancer cell death in a subject in need thereof comprising an effective amount of one or more gold(III) porphyrin-poly(ethylene glycol) (PEG) conjugates having the structural formula of:

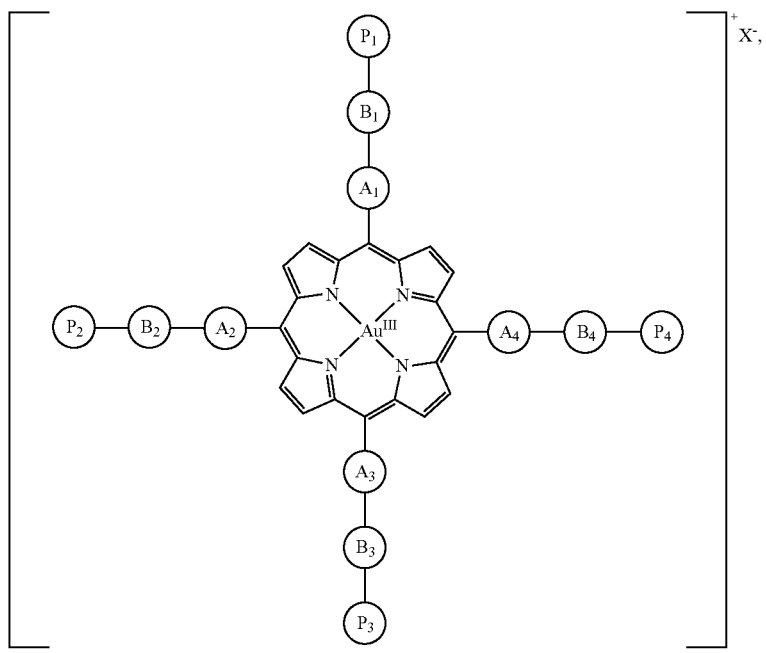

wherein:

X is independently a pharmaceutically acceptable counter-ion;

$A_1$, $A_2$, $A_3$ and $A_4$ are independently aryl or aryl substituted with a halogen, hydroxy, alkoxy, amino, amido, carboxyl, ester, carbonyl, formyl, thio, alkythio, sulfonyl, sulfonic acid, azidyl, nitro, isocyanate-yl, alkenyl, alkynyl, phosphoryl, or phosphonyl group, $B_1$, $B_2$, $B_3$, and $B_4$ are independently absent ($C_0$) or spacer molecules of $C_1$-$C_8$ alkyl groups with two end groups that form covalent linkages with $A_n$ and $P_n$; and $P_1$, $P_2$, $P_3$, and $P_4$ are independently hydrogen PEG, —O-PEG—$OCH_3$, or —NH-PEG—$OCH_3$, wherein, only one of $P_1$, $P_2$, $P_3$, and $P_4$ is PEG, —O-PEG—$OCH_3$, or —NH-PEG—$OCH_3$;

wherein said composition comprises self-assembled nanostructures of the one or more gold(III) porphyrin-PEG conjugates; and wherein, when administered to a subject in need of induction of cancer cell death, said composition induces apoptosis in cancer cells.

2. The composition of claim 1 further comprising one or more additional anti-cancer chemotherapeutic agents, wherein the gold(III) porphyrin-PEG nanostructures encapsulate the one or more anti-cancer chemotherapeutic agents, thereby forming nanocomposites for co-delivery.

3. The composition of claim 2, wherein one of the anti-cancer chemotherapeutic agents is doxorubicin or a $d^8$ metal complex with an N-heterocyclic carbene (NHC) ligand having the structural formula of:

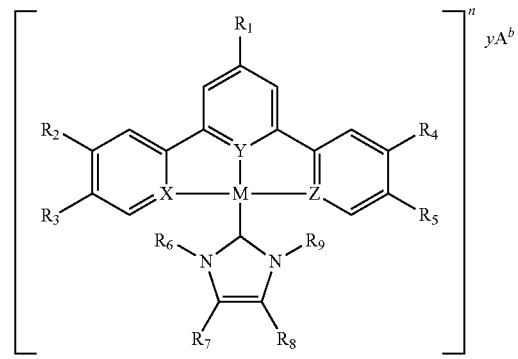

wherein:
M is Au, Pt, or Pd;
$R_1$ is hydrogen or phenyl;
$R_2$ and $R_3$ are each hydrogen or are linked together by —CH—CH—CH—CH—;
$R_4$, $R_5$, $R_7$, and $R_8$ are each hydrogen;
$R_6$ and $R_9$ are each independently selected from —$CH_3$, —$C_2H_5$, —$C_3H_7$, —$C_4H_9$, —$C_5H_{11}$, —$C_6H_{13}$, benzyl, (2-hydroxy) ethyl, phenyl, naphthalen-2-ylmethyl, and (2-phenyl) ethyl;
n is +1 or +2;
y is +1 or +2;
A is a counter-ion or a pharmaceutically acceptable anion;
b is −1 or −2; and
X, Y, Z in the NHC ligand are each independently carbon or nitrogen.

4. The composition of claim 3, wherein:
M is Pt;
$R_1$, $R_2$, $R_3$, $R_4$, $R_5$, $R_7$, and $R_8$ are each hydrogen;
$R_6$ and $R_9$ are —$C_4H_9$;
n is +1;
$yA^b$ is $CF_3SO_4^-$;

X in the NHC ligand is carbon; and

Y and Z in the NHC ligand are each nitrogen.

5. The composition of claim 2, wherein:

$A_1$ is $C_6H_4CO$- or —$C_6H_4O$-;

$B_1$ is $C_0$ or —$CO(CH_2)_8CO$—; and $P_1$ is —O-PEG—$OCH_3$ or —NH-PEG—$OCH_3$.

6. The composition of claim 5, wherein:

$P_1$ is —O-PEG$_{\sim 5000}$—$OCH_3$ or —NH-PEG$_{\sim 5000}$—$OCH_3$.

7. The composition of claim 2, wherein:

$A_2$, $A_3$ and $A_4$ are each aryl;

$B_2$, $B_3$ and $B_4$ are each $C_0$;

$P_2$, $P_3$ and $P_4$ are each hydrogen; and optionally, X is chloride.

8. A gold(III) porphyrin-PEG conjugate having the structural formula of:

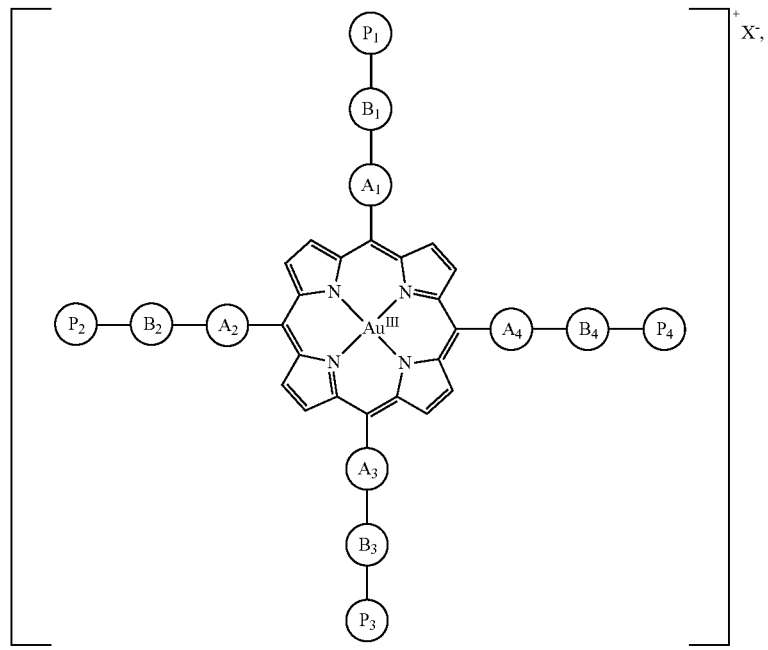

wherein:

X is independently a pharmaceutically acceptable counter-ion;

$A_1$, $A_2$, $A_3$ and $A_4$ are independently aryl or aryl substituted with a halogen, hydroxy, alkoxy, amino, amido, carboxyl, ester, carbonyl, formyl, thio, alkythio, sulfonyl, sulfonic acid, azidyl, nitro, isocyanate-yl, alkenyl, alkynyl, phosphoryl, or phosphonyl group, $B_1$, $B_2$, $B_3$ and $B_4$ are independently $C_0$ or spacer molecules of $C_1$-$C_8$ alkyl groups with two end groups; and $P_1$, $P_2$, $P_3$, and $P_4$ are independently hydrogen PEG, —O-PEG—$OCH_3$, or —NH-PEG—$OCH_3$, wherein, only one of $P_1$, $P_2$, $P_3$, and $P_4$ is PEG, —O-PEG—$OCH_3$, or —NH-PEG—$OCH_3$.

9. The composition of claim 1, wherein the one or more gold(III) porphyrin-PEG conjugates have a structure selected from the group consisting of:

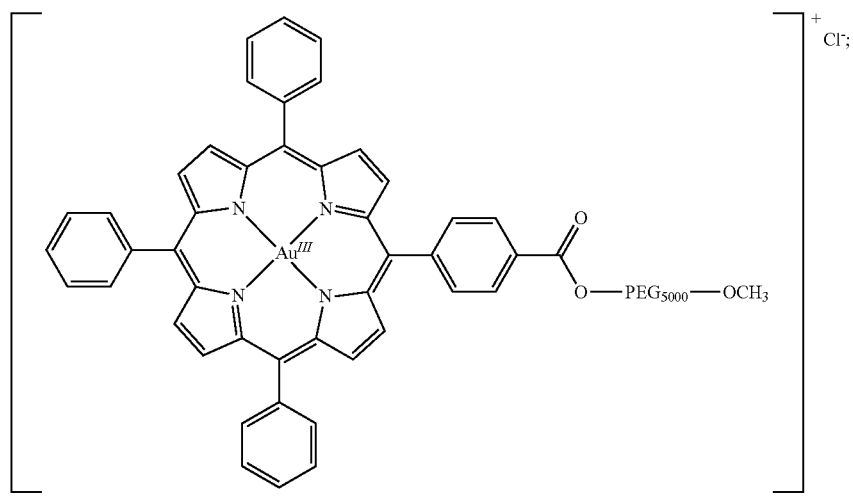
1
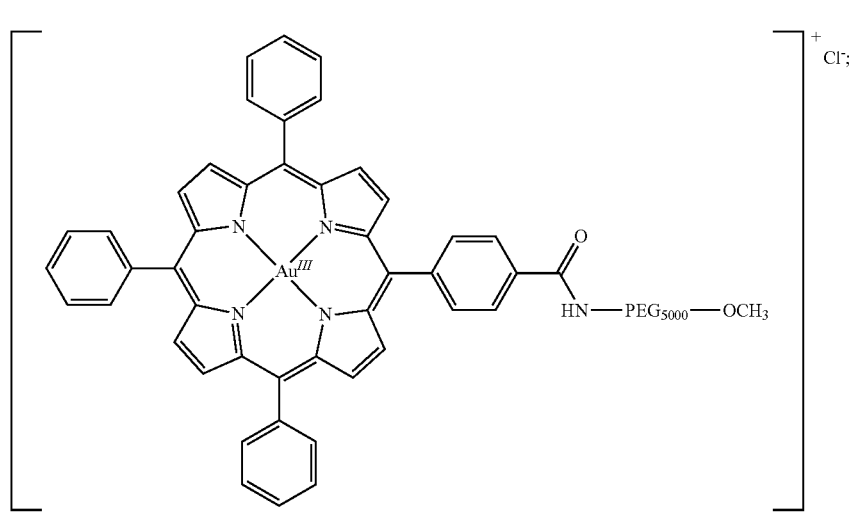
2
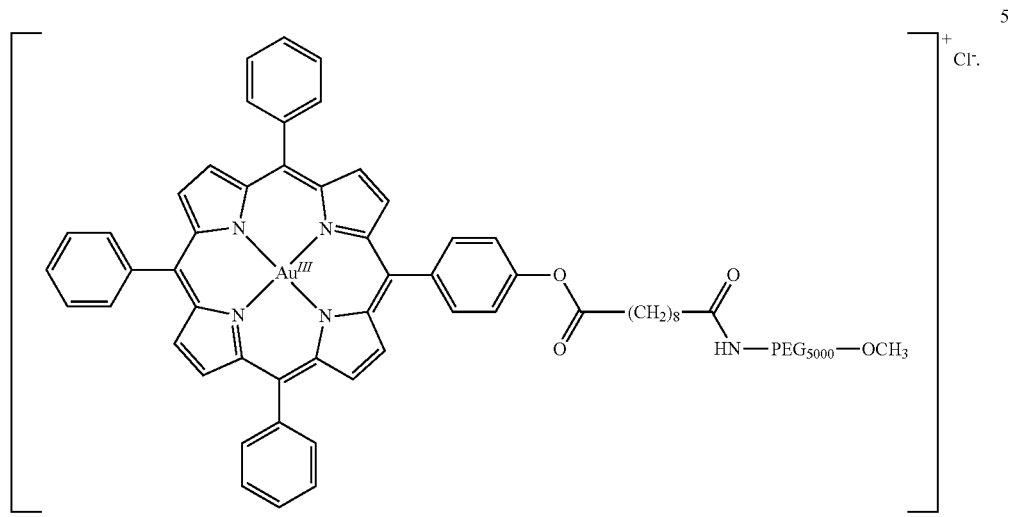
5

10. A composition for inducing cancer cell death in a subject in need thereof comprising an effective amount of one or more gold(III) porphyrin-PEG conjugates having a structure selected from the group consisting of,
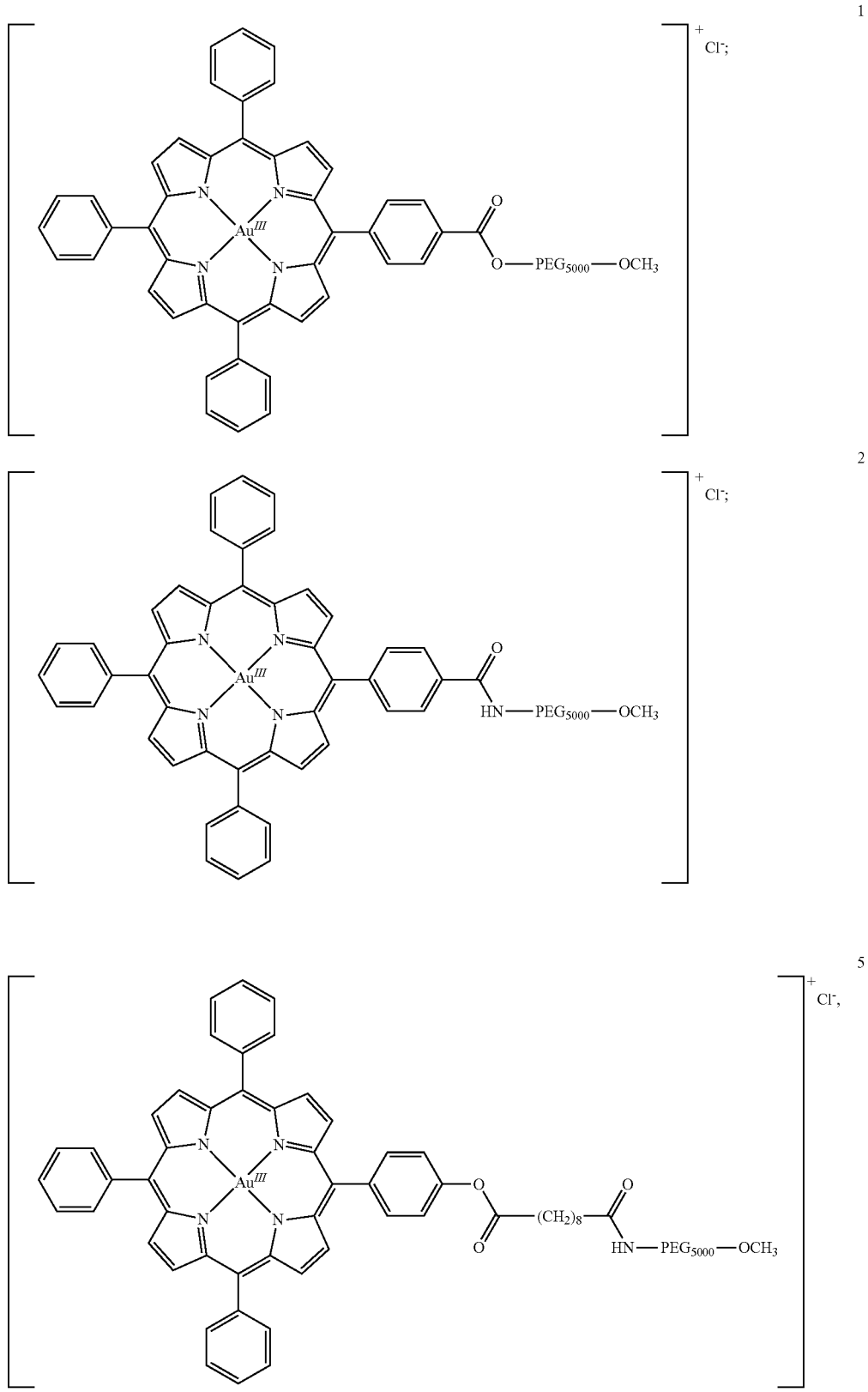

wherein, when administered to a subject in need of induction of cancer cell death, said composition induces apoptosis in cancer cells, and wherein said composition comprises self-assembled nanostructures of the one or more gold(III) porphyrin-PEG conjugates.

11. The composition of claim 1, comprising core-shell micelles formed by the gold(III)-porphyrin-PEG conjugates.

12. A method of inducing cancer cell death in a subject in need thereof comprising administering to the subject the composition of claim 1.

13. The method of claim 12, wherein the gold(III) porphyrin-PEG nanostructures encapsulate one or more anticancer chemotherapeutic agents, thereby forming nanocomposites for co-delivery.

14. The method of claim 12, wherein one of the anticancer chemotherapeutic agents is doxorubicin or is a $d^8$ metal complex with an N-heterocyclic carbene (NHC) ligand having the structural formula of:

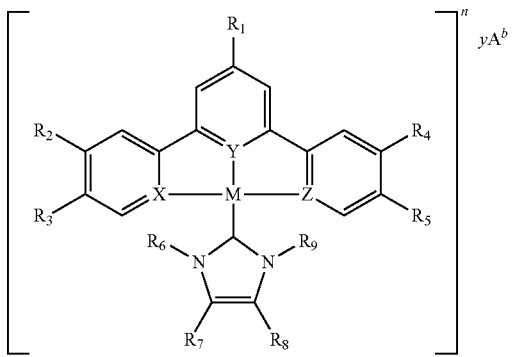

wherein:
M is Au, Pt, or Pd;
$R_1$ is hydrogen or phenyl;
$R_2$ and $R_3$ are each hydrogen or are linked together by —CH—CH—CH—CH—;
$R_4$, $R_5$, $R_7$, and $R_8$ are each hydrogen;
$R_6$ and $R_9$ are each independently selected from —CH$_3$, —C$_2$H$_5$, —C$_3$H$_7$, —C$_4$H$_9$, —C$_5$H$_{11}$, —C$_6$H$_{13}$, benzyl, (2-hydroxy) ethyl, phenyl, naphthalen-2-ylmethyl, and (2-phenyl) ethyl;
n is +1 or +2;
y is +1 or +2;
A is a counter-ion or a pharmaceutically acceptable anion;
b is −1 or −2; and
X, Y, and Z are each independently carbon or nitrogen.

15. The method of claim 14, wherein:
M is Pt;
$R_1$, $R_2$, $R_3$, $R_4$, $R_5$, $R_7$, and $R_8$ are each hydrogen;
$R_6$ and $R_9$ are —C$_4$H$_9$;
n is +1;
$yA^b$ is CF$_3$SO$_4$-;
X is carbon; and
Y and Z are each nitrogen.

16. The method of claim 12, wherein:
$A_1$ is —C$_6$H$_4$CO- or —C$_6$H$_4$O—;
$B_1$ is $C_0$ or —CO(CH$_2$)$_8$CO—; and
$P_1$ is —O-PEG—OCH$_3$ or —NH-PEG—OCH$_3$.

17. The method of claim 16, wherein:
$P_1$ is —O-PEG$_{\sim 5000}$—OCH$_3$ or —NH-PEG$_{\sim 5000}$—OCH$_3$.

18. The method of claim 16, wherein:
$A_2$, $A_3$ and $A_4$ are each aryl;
$B_2$, $B_3$ and $B_4$ are each $C_0$;
$P_2$, $P_3$ and $P_4$ are each hydrogen; and
optionally, X is chloride.

19. The method of claim 12, wherein the subject has a cancer selected from the group consisting of colorectal, colon ovarian, lung, breast carcinoma and multiple myeloma, cisplatin-resistant cancer, and adriamycin-resistant cancer.

20. A method of targeting delivery of an anticancer therapeutic agent to cancer cells in a subject, the method comprising administering to the subject by enteral, parenteral, topical or pulmonary route the composition of claim 2.

21. The method of claim 4, wherein one of the therapeutic agents is doxorubicin or a $d^8$ metal complex with an NHC ligand having the structural formula of:

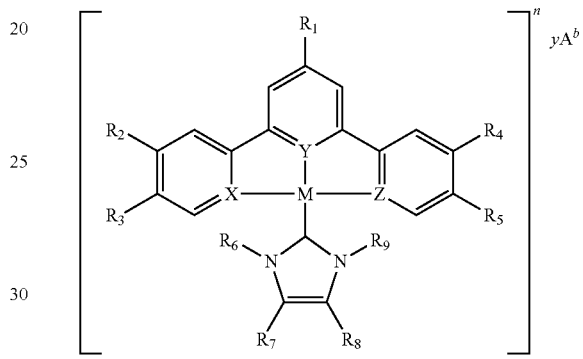

wherein:
M is Au, Pt, or Pd;
$R_1$ is hydrogen or phenyl;
$R_2$, $R_3$, $R_4$, $R_5$, $R_7$, and $R_8$ are each hydrogen;
$R_6$ and $R_9$ are each independently selected from —CH$_3$, —C$_2$H$_5$, —C$_3$H$_7$, —C$_4$H$_9$, —C$_5$H$_{11}$, —C$_6$H$_{13}$, benzyl, (2-hydroxy) ethyl, phenyl, naphthalen-2-ylmethyl, and (2-phenyl) ethyl;
n is +1 or +2;
y is +1 or +2;
A is a counter-ion or a pharmaceutically acceptable anion;
b is −1 or −2; and
X, Y, Z are each independently carbon or nitrogen.

22. The method of claim 21, wherein:
M is Pt;
$R_1$, $R_2$, $R_3$, $R_4$, $R_5$, $R_7$, and $R_8$ are each hydrogen;
$R_6$ and $R_9$ are —C$_4$H$_9$;
n is +1;
$yA^b$ is CF$_3$SO$_4$-;
X is carbon; and
Y and Z are each nitrogen.

23. The method of claim 4, wherein:
$A_1$ is —C$_6$H$_4$CO- or —C$_6$H$_4$O—;
$B_1$ is $C_0$ or —CO(CH$_2$)$_8$CO—; and
$P_1$ is —O-PEG—OCH$_3$ or —NH-PEG—OCH$_3$.

24. The method of claim 23, wherein:
$P_1$ is —O-PEG-$_{\sim 5000}$—OCH$_3$ or —NH-PEG$_{\sim 5000}$—OCH$_3$.

25. The method of claim 23, wherein:
$A_2$, $A_3$ and $A_4$ are each aryl;
$B_2$, $B_3$ and $B_4$ are each $C_0$;
$P_2$, $P_3$ and $P_4$ are each hydrogen; and
optionally, X is chloride.

* * * * *